United States Patent
Zhang et al.

(10) Patent No.: US 8,822,447 B2
(45) Date of Patent: Sep. 2, 2014

(54) INDAZOLE COMPOUNDS USEFUL AS KETOHEXOKINASE INHIBITORS

(75) Inventors: Xuqing Zhang, Spring House, PA (US); Marta C. Abad, Dowingtown, PA (US); Alan C. Gibbs, Wyndmoor, PA (US); Gee-Hong Kuo, Scotch Plains, NJ (US); Lawrence C. Kuo, Gwynedd Valley, PA (US); Fengbin Song, Princeton, NJ (US); Zhihua Sui, Spring House, PA (US)

(73) Assignee: Janssen Pharmaceutica NV (BE)

( * ) Notice: Subject to any disclaimer, the term of this patent is extended or adjusted under 35 U.S.C. 154(b) by 407 days.

(21) Appl. No.: 13/091,344

(22) Filed: Apr. 21, 2011

(65) Prior Publication Data

US 2011/0263559 A1 Oct. 27, 2011

Related U.S. Application Data

(60) Provisional application No. 61/326,749, filed on Apr. 22, 2010.

(51) Int. Cl.

| | | |
|---|---|---|
| A61K 31/416 | (2006.01) | |
| A61K 31/4439 | (2006.01) | |
| A61K 31/454 | (2006.01) | |
| A61K 31/4545 | (2006.01) | |
| A61K 31/496 | (2006.01) | |
| A61K 31/519 | (2006.01) | |
| A61K 31/551 | (2006.01) | |
| C07D 401/12 | (2006.01) | |
| C07D 401/14 | (2006.01) | |
| C07D 403/10 | (2006.01) | |
| C07D 403/12 | (2006.01) | |
| C07D 471/04 | (2006.01) | |
| C07D 487/04 | (2006.01) | |
| C07D 487/08 | (2006.01) | |
| A61P 3/04 | (2006.01) | |
| A61P 3/06 | (2006.01) | |
| A61P 3/10 | (2006.01) | |

(52) U.S. Cl.
USPC ............. 514/210.18; 514/210.21; 514/218; 514/252.16; 514/253.09; 514/254.06; 514/303; 514/322; 514/338; 514/407; 540/575; 544/262; 544/364; 544/371; 546/119; 546/199; 546/275.7; 548/361.5

(58) Field of Classification Search
None
See application file for complete search history.

(56) References Cited

FOREIGN PATENT DOCUMENTS

| JP | 6199855 | 7/1994 |
|---|---|---|
| WO | WO 98/09961 A1 | 3/1998 |
| WO | WO 00/21926 A2 | 4/2000 |
| WO | WO 2005/063765 A1 | 7/2005 |
| WO | WO 98/24902 A2 | 2/2008 |

OTHER PUBLICATIONS

Gibbs, et al., "Electron Density Guided Fragment-Based Lead Discovery of Ketohexokinase Inhibitors", J. Med. Chem., 2010, pp. 7979-7991, vol. 53.
International Search Report, PCT/US2011/033395, dated Jul. 18, 2007.
Ahluwalila, V., et al. "Reaction of 5-amino-4-formyl-3-methyl (or phenyl)-1-phenyl-1H-pyrazoles With Active Methylene Compounds: Synthesis of Fused Heterocyclic Rings", Accession No. 1472, Indian Journal of Chemistry, Section B; Organic Chemistry Including Medicinal Chemistry, pp. 88-90 (1997)(XP-002643906).
Ahluwalia, V., et al., "Reaction of 5-amino-4-formyl-3-methyl (or phenyl)-1-phenyl-1H-pyrazoles With Active Methylene Compounds: Synthesis of Fused Heterocyclic Rings", Indian Journal of Chemistry, vol. 36B, pp. 88-90 (1997).
Dennler, E., et al. "Synthesis of Indazoles Using Polyphosphoric Acid-I", Tetrahedron, vol. 22, pp. 3131-3141 (1966) (XP-002643903).
El-Enany, M., et al. "Synthesis and Antitumor Activity of Novel 6-Aryl and 6-Alkylpyrazolo[3,4-d] Pyrimidin-4-one Derivatives", European Journal of Medicinal Chemistry, vol. 45, pp. 5286-5291 (2010) (XP-002643908).
Heravi, M., et al. "A Catalytic Method for Synthesis of 6-Aryl-1H-Pyrazolo[3,4-d]pyrimidin-4[5H]-ones by Heteropolyacids: $H_{14}[NaP_5W_{29}MoO_{110}]$ and $H_3PMo_{12}O_{40}$", Catalysis Communications, vol. 8, pp. 1467-1471 (2007) (XP-002643901).
Lubbers, T., et al. "Design, Synthesis and Structure-Activity Relationship Studies of ATP Analogues as DNA Gyrase Inhibitors", Bioorganic & Medicinal Chemistry Letters, vol. 10, pp. 821-826 (2000) (XP-002643900).

(Continued)

*Primary Examiner* — Susanna Moore
(74) *Attorney, Agent, or Firm* — Mary A. Appollina

(57) ABSTRACT

The present invention is directed to substituted indazole compounds of formula (I)

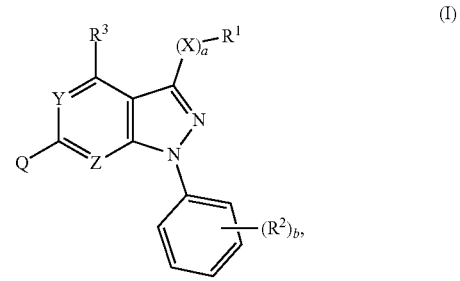

pharmaceutical compositions of these compounds and methods of use thereof. The compounds of the present invention are ketohexokinase (KHK) inhibitors, useful for treating or ameliorating a KHK mediated metabolic disorders and/or diseases such as obesity, Type II diabetes mellitus and Metabolic Syndrome X.

12 Claims, No Drawings

(56) References Cited

OTHER PUBLICATIONS

Strakova, I., et al. "Bromination of 4-oxo-4,5,6,7-Tetrahydroinadazoles", (Accession No. 1474) (XP-002643905), (1973).

Wang, H-Q., et al. "Versatile Synthesis and Fungicidal Activities of 6-amino-3-alkylthio-1,5-dihydro-1-phenyl-pyrazolo[3,4-d]pyrimididin-4-6-amino-3-alkylthio-1, 5-dihydro-1-phenyl—pyrazolo[3,4-d]pyrimidin-4-one Derivatives" Phosphorus, Sulfur and Silicon and the Related Elements, vol. 179(10), pp. 2039-2050 (2004) (XP-002643904).

Wang, H-Q., et al. Accession No. 1449 (XP-002643904), (2004).

Quiroga, J., et al. "Reaction of 5-Aminopyrazoles with β-Dimethylaminopropiophenones. Synthesis of New Pyrazolo[3,4-b]pyridines", J. Heterocyclic Chemistry, vol. 35, pp. 333 (1998) (XP-002643902).

INDAZOLE COMPOUNDS USEFUL AS KETOHEXOKINASE INHIBITORS

CROSS-REFERENCE TO RELATED APPLICATIONS

This application claims priority from U.S. Provisional Application Ser. No. 61/326,749 filed Apr. 22, 2010, the contents of each of which are hereby incorporated by reference in their entirety.

FIELD OF THE INVENTION

The present invention is directed toward substituted indazole compounds, pharmaceutical compositions of these compounds and methods of use thereof. More particularly, the compounds of the present invention are ketohexokinase (KHK) inhibitors are useful for treating or ameliorating a KHK mediated metabolic disorder syndrome or disease.

BACKGROUND OF THE INVENTION

While non-insulin dependent diabetes mellitus (NIDDM) is most commonly associated with hyperglycemia and insulin resistance, it is frequently accompanied by a cluster of pathologies, more commonly referred to as the Metabolic Syndrome. The hallmarks of this syndrome are obesity, hypertriglyceridemia, insulin resistance, and hypertension. The high prevalence of these disorders and associated co-morbidities, such as cardiovascular disease and stroke, has lead to increased desire for both preventive care and therapeutic interventions. Current pharmacotherapies for NIDDM range in strategy to include agents that increase insulin secretion, impact insulin action (thiazolidiones, biguanides), alter lipid metabolism (TZD's, fibrates), affect central-feeding behavior, and reduce nutrient absorption (lipase inhibitors). Targeting fructose metabolism offers a novel alternative to current treatment strategies. Recent ecological studies have demonstrated a significant positive correlation between increased energy intake, in the form of highly refined sugars, and the prevalence of both NIDDM and obesity in the U.S. Diets high in fructose have been shown to promote a variety of metabolic disturbances in animal models, including weight gain, hyperlipidemia, hypertension, and insulin resistance. In studies with overweight human subjects, long-term consumption of fructose increased energy intake, body weight, fat mass, blood pressure, and triglyceride (TG) levels. Ingestion of high-fructose diets stimulates de-novo lipogenesis (via up regulation of lipogenic gene expression and activity), shifts the balance between oxidation in favor of re-esterification of fatty acids (FA's), and increases the production of very low density lipoprotein (VLDL) particles. Chronic consumption of diets high in fructose induces elevated levels of free fatty acids (FFA's) and TG's that impair both glucose utilization in muscle tissue and increase the rate of lipolysis in adipose tissue. Fructose-induced TG production may impair insulin-signaling pathways, may be associated with chronic inflammation and may lead to glucolipidtoxicity and can ultimately lead to β-cell failure. Reduction of fructose in the systemic circulation offers the potential to ameliorate the metabolic abnormalities associated with increased fructose consumption and represents a novel therapeutic strategy to treat both NIDDM and Metabolic Syndrome.

Fructose is readily absorbed from the diet and is metabolized rapidly in the liver. Fructokinase, also known as ketohexokinase, is the hepatic enzyme that phosphorylates fructose to fructose-1-phosphate and serves as the entry point of this sugar into the metabolic pathway. In contrast to the highly regulated process of glucose metabolism, fructose metabolism lacks similar control mechanisms. For example, fructokinase has a high $K_M$ value, is not inhibited by product, and is not allosterically regulated. Consequently, high concentrations of fructose can rapidly flux into glycolytic pathways and provide both the glycerol and acyl components of triglycerides (TG). Thus, the metabolism of fructose provides a relatively unregulated source of carbon substrates that promotes TG synthesis and underlies a variety of metabolic disorders. Human genetic validation of this target is supported by the discovery of mutations that cause the autosomal recessive disorder essential fructosuria. Individuals with this benign condition have inactive isoforms of hepatic fructokinase. Upon ingestion of fructose, sucrose, or sorbitol, affected individuals exhibit a significant and persistent rise in blood fructose concentrations, and excrete part of the load in the urine. This supports the rationale that a fructokinase inhibitor would spill excess carbohydrate into the urine with a significant margin of safety. This approach represents a novel therapeutic strategy to reduce body weight, FFA's and TG levels, and serve the unmeet needs of both NIDDM and Metabolic Syndrome.

SUMMARY OF THE INVENTION

The present invention is directed to compounds of formula (I)

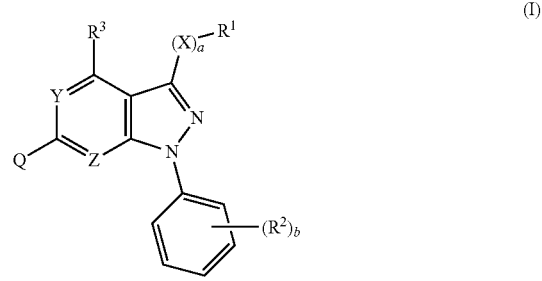

wherein a is an integer from 0 to 1;

X is selected from the group consisting of —O— and —S—;

$R^1$ is selected from the group consisting of $C_{1-4}$alkyl and halogenated $C_{1-4}$alkyl;

b is an integer from 0 to 2;

$R^2$ is selected from the group consisting of halogen, hydroxy, cyano, nitro, $NR^AR^B$, $C_{1-4}$alkyl, —O—$C_{1-4}$alkyl, —S—$C_{1-4}$alkyl and halogenated $C_{1-4}$alkyl; wherein $R^A$ and $R^B$ are each independently selected from the group consisting of hydrogen and $C_{1-4}$alkyl;

$R^3$ is selected from the group containing of hydrogen, halogen, hydroxy, —O—$C_{1-4}$alkyl and $NR^CR^D$; wherein $R^C$ and $R^D$ are each independently selected from the group consisting of hydrogen and $C_{1-4}$alkyl;

Y is CH and Z is CH; alternatively Y is CH and Z is N; alternatively Y is N and Z is N;

Q is selected from the group consisting of -$(L^1)_c$-(Ring A), -$(L^1)_c$-(Ring B)-(Ring C) and -(Ring B)-$L^1$-(Ring C);

c is an integer from 0 to 1;

$L^1$ is selected from the group consisting of —$CH_2$—, —CH(OH)—, —$CH_2CH_2$—, —$CH_2CH_2CH_2$—, —CH=CH—, —CH=CH—$CH_2$—, —O—, —O—$CH_2$—, —C(O)—, —C(O)—C(O)—, —C(O)—

—CH$_2$—, —C(O)—N(R$^4$)—, —N(R$^4$)—, —N(R$^4$)—CH$_2$—, —N(R$^4$)—CH$_2$CH$_2$—, —N(R$^4$)—(CO)—, —N(R$^4$)—C(O)—CH$_2$—, —N(R$^4$)—C(O)—CH$_2$—CH$_2$— and —N(R$^4$)—C(O)—N(R$^5$)—; wherein R$^4$ and R$^5$ are each independently selected from the group consisting of hydrogen and C$_{1-2}$alkyl;

(Ring A) is selected from the group consisting of phenyl and 4 to 10 membered, nitrogen containing ring structure; wherein (Ring A) is optionally substituted with a substituent selected from the group consisting of halogen, C$_{1-4}$alkyl, cyano, NR$^E$R$^F$, —C(=NH)—NR$^E$R$^F$, —C(O)—CH$_2$—NR$^E$R$^F$, —C(O)—CH$_2$CH$_2$—NR$^E$R$^F$ and phenyl; wherein R$^E$ and R$^F$ are each independently selected from the group consisting of hydrogen and C$_{1-4}$alkyl;

(Ring B) is selected from the group consisting of phenyl and 4 to 10 membered, nitrogen containing ring structure;

(Ring C) is selected from the group consisting of 4 to 10 membered, nitrogen containing ring structure; wherein (Ring C) is optionally substituted with one to two substituents independently selected from the group consisting C$_{1-4}$alkyl;

and pharmaceutically acceptable salts thereof.

The present invention is further directed to processes for the preparation of the compounds of formula (I). The present invention is further directed to a product prepared according to the process described herein.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by KHK (selected from the group consisting of obesity, elevated glucose levels, glucose intolerance, insulin resistance, Type I diabetes mellitus, Type II diabetes mellitus, Metabolic Syndrome X, elevated triglycerides, hyperlipidemia and hypertension) comprising administering to a subject in need thereof a therapeutically effective amount of any of the compounds or pharmaceutical compositions described above.

Exemplifying the invention are methods of treating a disorder selected from the group consisting of obesity, elevated glucose levels, glucose intolerance, insulin resistance, Type I diabetes mellitus, Type II diabetes mellitus, Metabolic Syndrome X, elevated triglycerides, hyperlipidemia and hypertension comprising administering to a subject in need thereof a therapeutically effective amount of any of the compounds or pharmaceutical compositions described above.

Another example of the present invention is the use of any of the compounds described herein in the preparation of a medicament for treating obesity, elevated glucose levels, glucose intolerance, insulin resistance, Type I diabetes mellitus, Type II diabetes mellitus, Metabolic Syndrome X, elevated triglycerides, hyperlipidemia or hypertension.

Another example of the present invention is the use of any of the compounds described herein in a method for treating a disorder selected from the group consisting of obesity, elevated glucose levels, glucose intolerance, insulin resistance, Type I diabetes mellitus, Type II diabetes mellitus, Metabolic Syndrome X, elevated triglycerides, hyperlipidemia and hypertension, in a subject in need thereof.

DETAILED DESCRIPTION OF THE INVENTION

The present invention is directed to compounds of formula (I)

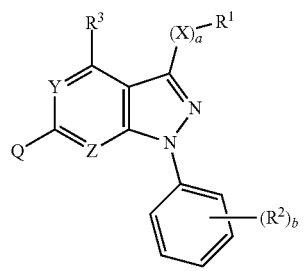

(I)

wherein a, X, R$^1$, b, R$^2$, R$^3$, Y, Z and Q are as herein defined, useful for the treatment of disorders mediated by a ketohexokinase. More particularly, the compounds of the present invention are useful in the treatment of obesity, elevated glucose levels, glucose intolerance, insulin resistance, Type I diabetes mellitus, Type II diabetes mellitus, Metabolic Syndrome X, elevated triglycerides, hyperlipidemia, hypertension, related metabolic syndromes and/or disorders.

In an embodiment of the present invention, a is 0. In another embodiment of the present invention, a is 1.

In an embodiment of the present invention X is —O—. In another embodiment of the present invention, X is —S—.

In an embodiment of the present invention, R$^1$ is selected from the group consisting of C$_{1-4}$alkyl and fluorinated C$_{1-4}$alkyl. In another embodiment of the present invention, R$^1$ is selected from the group consisting of C$_{1-2}$alkyl and fluorinated C$_{1-2}$alkyl. In another embodiment of the present invention, R$^1$ is C$_{1-4}$alkyl. In another embodiment of the present invention, R$^1$ is selected from the group consisting of methyl and ethyl. In another embodiment of the present invention, R$^1$ is methyl.

In an embodiment of the present invention, b is an integer from 1 to 2. In another embodiment of the present invention, b is an integer form 0 to 1.

In an embodiment of the present invention, R$^2$ is selected from the group consisting of bromo, fluoro, methyl, methoxy, nitro and amino. In another embodiment of the present invention, R$^2$ is selected from the group consisting of fluoro, methyl, methoxy, nitro and amino. In another embodiment of the present invention, R$^2$ is selected from the group consisting of fluoro, methyl, methoxy and amino. In another embodiment of the present invention, R$^2$ is selected from the group consisting of 4-bromo, 2-fluoro, 3-fluoro, 4-fluoro, 2-methyl, 3-methyl, 4-methyl, 4-methoxy, 4-nitro and 4-amino.

In an embodiment of the present invention, the R$^2$ group(s) are bound to the 2-, 3- and/or 4-position of the phenyl. In another embodiment of the present invention, the R$^2$ group(s) are bound to the 3- and/or 4-position of the phenyl. In another embodiment of the present invention, the R$^2$ group(s) are bound at the 2- and 4-positions of the phenyl.

In an embodiment of the present invention, R$^3$ is selected from the group consisting of hydrogen, hydroxy, —O-methyl and —O-ethyl. In another embodiment of the present invention, R$^3$ is selected from the group consisting of hydrogen and —O-methyl. In another embodiment of the present invention, R$^3$ is hydrogen.

In an embodiment of the present invention, Y is CH and Z is CH. In another embodiment of the present invention, Y is CH and Z is N. In another embodiment of the present invention, Y is N and Z is N. In another embodiment of the present invention Y is CH and Z is selected from the group consisting of CH and N (i.e. Y is CH and Z is CH; alternatively Y is CH and Z is N).

In an embodiment of the present invention, Q is -($L^1$)$_c$-(Ring A). In another embodiment of the present invention, Q is -($L^1$)$_c$-(Ring B)-(Ring C). In another embodiment of the present invention, Q is -(Ring B)-$L^1$-(Ring C). In another embodiment of the present invention, Q is selected from the group consisting of -($L^1$)$_c$-(Ring A) and -($L^1$)$_c$-(Ring B)-(Ring C).

In an embodiment of the present invention, c is 0. In another embodiment of the present invention, c is 1.

In an embodiment of the present invention, $L^1$ is selected from the group consisting of —$CH_2$—, —CH(OH)—, —$CH_2$—$CH_2$—, —CH=CH—, —O—, —O—$CH_2$—, —C(O)—, —C(O)—NH—, —C(O)—$CH_2$—, —C(O)—C(O)—, —NH—, —NH—C(O)—, —NH—$CH_2$—, —N(ethyl)-$CH_2$—, —NH—$CH_2$—$CH_2$—, —NH—C(O)—$CH_2$—, —NH—C(O)—$CH_2$—$CH_2$—, and —NH—C(O)—NH—. In another embodiment of the present invention, $L^1$ is selected from the group consisting of —$CH_2$—$CH_2$—, —CH=CH—, —O—, —O—$CH_2$—, —C(O)—, —NH—, —NH—C(O)—, —NH—$CH_2$—, —N(ethyl)-$CH_2$—, —NH—$CH_2$—$CH_2$—, —NH—C(O)—$CH_2$—, —NH—C(O)—$CH_2$—$CH_2$— and —NH—C(O)—NH—. In another embodiment of the present invention, $L^1$ is selected from the group consisting of —CH=CH—, —O—$CH_2$—, —NH—C(O)—, —NH—$CH_2$—, —NH—C(O)—$CH_2$—, —NH—C(O)—$CH_2$—$CH_2$— and —NH—C(O)—NH—. In another embodiment of the present invention, $L^1$ is selected from the group consisting of —CH=CH—, —O—$CH_2$—, —NH—C(O)—, —NH—$CH_2$—, —NH—C(O)—$CH_2$—$CH_2$— and —NH—C(O)—NH—. In another embodiment of the present invention, $L^1$ is selected from the group consisting of —CH=CH— and —NH—C(O). In another embodiment of the present invention, $L^1$ is —NH—C(O)—.

In an embodiment of the present invention, (Ring A) is selected from the group consisting of 3-cyano-phenyl, 3-benzimidamide, azetidin-3-yl, piperazin-1-yl, 4-methyl-piperazin-1-yl, 3-methyl-piperazin-1-yl, 4-ethyl-piperazin-1-yl, 4-isopropyl-piperazin-1-yl, piperazin-4-yl, piperidin-1-yl, piperidin-2-yl, piperidin-3-yl, piperidin-4-yl, 4-amino-piperidin-4-yl, 4-methyl-piperidin-4-yl, 4-fluoro-piperidin-4-yl, 4-phenyl-piperidin-4-yl, pyrrolidin-2-yl, pyrrolidin-3-yl, 3-amino-pyrrolidin-1-yl, pyrid-2-yl, pyrid-3-yl, pyrid-4-yl, 6-methyl-pyrid-3-yl, 1,2,3,6-tetrahydropyrid-4-yl, 1-(amino-methyl-carbonyl)-1,2,3,6-tetrahydropyrid-4-yl, 1-(amino-ethyl-carbonyl)-1,2,3,6-tetrahydropyrid-4-yl, 1,4-diazepan-1-yl, benzimidazol-5-yl, 1-methyl-benzimidazol-6-yl, 1-methyl-benzimidazol-5-yl, benzo[c][1,2,5]oxadiazol-5-yl, 2,5-diazabicyclo[2.2.1]hept-1-yl, 2,7-diazaspiro[4,4]nonan-2-yl and octahydropyrrolo[3,4-c]pyrrol-2-yl.

In another embodiment of the present invention, (Ring A) is selected from the group consisting of 3-benzimidamide, azetidin-3-yl, piperazin-1-yl, 3-methyl-piperazin-1-yl, piperidin-1-yl, piperidin-2-yl, piperidin-3-yl, piperidin-4-yl, 4-amino-piperidin-4-yl, 4-methyl-piperidin-4-yl, 4-fluoro-piperidin-4-yl, pyrrolidin-2-yl, pyrrolidin-3-yl, 3-amino-pyrrolidin-1-yl, pyrid-3-yl, 1,2,3,6-tetrahydropyrid-4-yl, 1-(amino-ethyl-carbonyl)-1,2,3,6-tetrahydropyrid-4-yl, 1,4-diazepan-1-yl, benzimidazol-5-yl, and 2,5-diazabicyclo[2.2.1]hept-1-yl. In another embodiment of the present invention, (Ring A) is selected from the group consisting of azetidin-3-yl, piperazin-1-yl, 3-methyl-piperazin-1-yl, piperidin-3-yl, piperidin-4-yl, 4-amino-piperidin-4-yl, pyrrolidin-2-yl, pyrrolidin-3-yl, pyrid-3-yl, 1,2,3,6-tetrahydropyrid-4-yl, 1-(amino-ethyl-carbonyl)-1,2,3,6-tetrahydropyrid-4-yl and benzimidazol-5-yl. In another embodiment of the present invention, (Ring A) is selected from the group consisting of azetidin-3-yl, piperazin-1-yl, 3-methyl-piperazin-1-yl, piperidin-3-yl, piperidin-4-yl, pyrrolidin-2-yl, pyrid-3-yl, 1,2,3,6-tetrahydropyrid-4-yl, 1-(amino-ethyl-carbonyl)-1,2,3,6-tetrahydropyrid-4-yl and benzimidazol-5-yl. In another embodiment of the present invention, (Ring A) is selected from the group consisting of azetidin-3-yl, piperidin-4-yl, pyrid-3-yl, 1,2,3,6-tetrahydropyrid-4-yl and benzimidazol-5-yl. In another embodiment of the present invention, (Ring A) is selected from the group consisting of piperidin-4-yl and 1,2,3,6-tetrahydropyrid-4-yl.

In an embodiment of the present invention, (Ring B) is selected form the group consisting of phenyl, azetidin-1-yl, azetidin-3-yl, piperidin-1-yl, piperidin-3-yl, piperidin-4-yl, piperazin-1-yl, pyrrolidin-1-yl and 1-imidazolidin-2-one. In another embodiment of the present invention, (Ring B) is selected form the group consisting of phenyl, azetidin-1-yl, piperidin-1-yl, piperazin-1-yl, pyrrolidin-1-yl and 1-imidazolidin-2-one. In another embodiment of the present invention, (Ring B) is selected form the group consisting of phenyl, azetidin-1-yl, piperazin-1-yl, and 1-imidazolidin-2-one. In another embodiment of the present invention, (Ring B) is selected form the group consisting of azetidin-1-yl, piperazin-1-yl, and 1-imidazolidin-2-one. In another embodiment of the present invention, (Ring B) is piperazin-1-yl.

In an embodiment of the present invention, (Ring C) is selected from the group consisting of azetidin-3-yl, piperidin-1-yl, piperidin-2-yl, piperidin-3-yl, piperidin-4-yl, piperazin-1-yl, piperazin-4-yl, 4-methyl-piperazin-1-yl, 3,5-dimethyl-piperazin-1-yl, pyrrolidin-2-yl, pyrrolidin-3-yl, pyrid-2-yl, pyrid-3-yl, pyrid-4-yl and imidazol-1-yl. In another embodiment of the present invention, (Ring C) is selected from the group consisting of piperidin-1-yl, piperidin-4-yl, piperazin-1-yl, 4-methyl-piperazin-1-yl, 3,5-dimethyl-piperazin-1-yl, pyrrolidin-3-yl and pyrid-4-yl. In another embodiment of the present invention, (Ring C) is selected from the group consisting of piperidin-1-yl, piperidin-4-yl, piperazin-1-yl, 3,5-dimethyl-piperazin-1-yl, pyrrolidin-3-yl and pyrid-4-yl. In another embodiment of the present invention, (Ring C) is selected from the group consisting of piperidin-1-yl, piperidin-4-yl, piperazin-1-yl, pyrrolidin-3-yl and pyrid-4-yl. In another embodiment of the present invention, (Ring C) is piperidin-4-yl.

In an embodiment of the present invention, when Q is -($L^1$)$_c$-(Ring B)-(Ring C), then (Ring C) is bound to the 1-, 3- or 4-position of (Ring B). Preferably, (Ring C) is bound to the 3- or 4-position of (Ring B). In another embodiment of the present invention, when Q is -($L^1$)$_c$-(Ring B)-(Ring C), then (Ring C) is bound to the meta- or para-position of (Ring B), relative to the position of binding of (Ring B) to the rest of the compound of formula (I).

In an embodiment of the present invention, when Q is -(Ring B)-$L^1$-(Ring C), then $L^1$ group is bound to the 1-, 3- or 4-position of (Ring B). In another embodiment of the present invention, when Q is -(Ring B)-$L^1$-(Ring C), then $L^1$ is bound to the meta- or para-position of (Ring B), relative to the position of binding of (Ring B) to the rest of the compound of formula (I).

Additional embodiments of the present invention, include compounds of formula (I) wherein the substituents selected for one or more of the variables defined herein (e.g., a, X, $R^1$, b, $R^2$, $R^3$, Y, Z, Q, c, $L^1$, (Ring A), (Ring B), (Ring C), etc.) are independently selected to be any individual substituent or any subset of substituents selected from the complete list as defined herein. Additional embodiments of the present invention further include compounds of formula (I) wherein the substituents selected for one or more of the variables defined herein (e.g., a, X, $R^1$, b, $R^2$, $R^3$, Y, Z, Q, c, $L^1$, (Ring A), (Ring B), (Ring C), etc.) are independently selected to be any individual substituent or any subset of substituents selected from those exemplified in the listings in Tables 1 to 8, below. In additional embodiments, the present invention is directed to any single compound or subset of compounds selected from the representative compounds listed in Tables 1 to 8, below.

Representative compounds of formula (I) of the present invention are as listed in Tables 1 to 8, below.

TABLE 1

Representative Compounds of Formula (I)

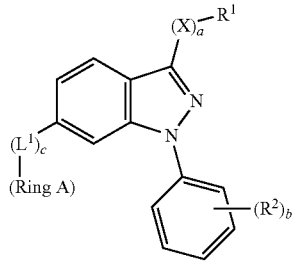

Y = CH, W = CH, R³ = H

| ID No. | —(X)ₐ—R¹ | (R²)ᵦ | (L¹)𝒸 | (Ring A) |
|---|---|---|---|---|
| 1 | —S-methyl | b = 0 | c = 0 | piperazin-1-yl |
| 2 | —S-methyl | b = 0 | —NH—C(O)— | azetidin-3-yl |
| 3 | —S-methyl | b = 0 | —NH—C(O)—CH₂— | piperidin-2-yl |
| 4 | —S-methyl | b = 0 | —NH—C(O)—NH— | pyrrolidin-3-yl |
| 5 | —S-methyl | b = 0 | —NH—C(O)— | pyrrolidin-3-yl |
| 6 | —S-methyl | b = 0 | —NH—C(O)— | piperidin-4-yl |
| 7 | —S-methyl | b = 0 | —NH—C(O)—NH— | piperidin-4-yl |
| 8 | —S-methyl | b = 0 | —NH—C(O)— | pyrid-4-yl |
| 9 | —S-methyl | b = 0 | —NH—C(O)—CH₂— | pyrid-4-yl |
| 10 | —S-methyl | b = 0 | c = 0 | 2,5-diazabicyclo[2.2.1]-hept-1-yl |
| 11 | —S-methyl | b = 0 | c = 0 | 1,4-diazepan-1-yl |
| 12 | —S-methyl | b = 0 | —NH—C(O)— | piperidin-3-yl |
| 13 | —S-methyl | b = 0 | —NH—C(O)— | pyrrolidin-2-yl |
| 14 | —S-methyl | b = 0 | —NH—C(O)— | pyrid-3-yl |
| 38 | ethyl | b = 0 | —NH—C(O)— | benzimidazol-5-yl |
| 39 | ethyl | b = 0 | —NH—C(O)— | 3-cyano-phenyl |
| 40 | ethyl | b = 0 | —NH—C(O)— | 3-(benzimidamide) |
| 42 | ethyl | b = 0 | c = 0 | piperazin-1-yl |
| 50 | ethyl | b = 0 | c = 0 | octahydropyrrolo[3,4-c]pyrrol-2-yl |
| 51 | ethyl | b = 0 | c = 0 | 2,7-diazaspiro[4.4]nonan-2-yl |
| 54 | ethyl | b = 0 | c = 0 | 4-methyl-piperazin-1-yl |
| 55 | ethyl | b = 0 | c = 0 | 4-ethyl-piperazin-1-yl |
| 56 | ethyl | b = 0 | c = 0 | 3-methyl-piperazin-1-yl |
| 59 | methyl | b = 0 | c = 0 | piperazin-1-yl |
| 66 | methyl | b = 0 | —NH—C(O)— | benzimidazol-5-yl |
| 68 | methyl | b = 0 | c = 0 | 4-methyl-piperazin-1-yl |
| 69 | methyl | b = 0 | c = 0 | 4-ethyl-piperazin-1-yl |
| 70 | methyl | b = 0 | c = 0 | 4-isopropyl-piperazin-1-yl |
| 71 | methyl | b = 0 | c = 0 | 3-methyl-piperazin-1-yl |
| 72 | methyl | b = 0 | c = 0 | 3-amino-pyrrolidin-1-yl |
| 80 | —O-methyl | b = 0 | —NH—C(O)— | benzimidazol-5-yl |
| 107 | —S-methyl | b = 0 | —O—CH₂— | piperidin-4-yl |
| 108 | —S-methyl | b = 0 | —N(ethyl)—CH₂— | piperidin-4-yl |
| 109 | —S-methyl | b = 0 | —NH— | piperidin-4-yl |
| 110 | —S-methyl | 4-nitro | —C(O)—NH— | piperidin-4-yl |
| 111 | —S-methyl | 4-amino | —C(O)—NH— | piperidin-4-yl |
| 112 | —S-methyl | b = 0 | —NH—CH₂— | piperidin-4-yl |
| 115 | —S-methyl | 4-amino | —CH₂— | piperazin-1-yl |
| 116 | —S-methyl | 4-amino | c = 0 | 1,2,3,6-tetrahydropyrid-4-yl |
| 118 | —S-methyl | 3-methyl | c = 0 | piperazin-4-yl |
| 121 | —S-methyl | b = 0 | —O— | piperidin-4-yl |
| 122 | —O-methyl | 4-methoxy | c = 0 | piperazin-1-yl |
| 124 | —S-methyl | 4-nitro | c = 0 | 1,2,3,6-tetrahydropyrid-4-yl |
| 127 | —S-methyl | 4-bromo | —O— | piperidin-4-yl |
| 128 | —S-methyl | 4-bromo | —O—CH₂— | piperidin-1-yl |
| 130 | —S-methyl | 4-nitro | —CH₂— | piperazin-1-yl |
| 131 | —S-methyl | b = 0 | —NH—C(O)—CH₂— | piperazin-1-yl |
| 132 | —S-methyl | b = 0 | —NH—C(O)—CH₂—CH₂— | piperazin-1-yl |
| 133 | —S-methyl | 4-nitro | —C(O)— | piperazin-1-yl |
| 136 | —S-methyl | b = 0 | —CH(OH)— | piperidin-4-yl |
| 137 | —S-methyl | b = 0 | —CH(OH)— | pyrid-4-yl |
| 139 | —S-methyl | 4-fluoro | c = 0 | 1,2,3,6-tetrahydropyrid-4-yl |
| 140 | —O-methyl | 4-methoxy | c = 0 | 1,2,3,6-tetrahydropyrid-4-yl |
| 141 | —S-methyl | b = 0 | —CH═CH— | piperidin-4-yl |
| 142 | —S-methyl | b = 0 | —C(O)— | piperidin-4-yl |

TABLE 1-continued

Representative Compounds of Formula (I)

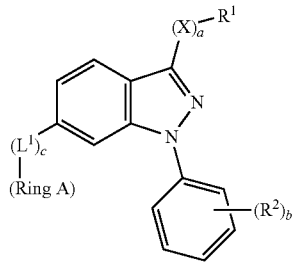

Y = CH, W = CH, R³ = H

| ID No. | —(X)ₐ—R¹ | (R²)ᵦ | (L¹)ᵧ | (Ring A) |
|---|---|---|---|---|
| 143 | —S-methyl | b = 0 | c = 0 | 1,2,3,6-tetrahydropyrid-4-yl |
| 144 | —S-methyl | 4-nitro | c = 0 | 1-(amino-methyl-carbonyl)-1,2,3,6-tetrahydropyrid-4-yl |
| 147 | —S-methyl | 3-methyl | c = 0 | 1,2,3,6-tetrahydropyrid-4-yl |
| 149 | —S-methyl | b = 0 | c = 0 | 1-(amino-ethyl-carbonyl)-1,2,3,6-tetrahydropyrid-4-yl |
| 152 | —S-methyl | b = 0 | —CH=CH— | 1,2,4-triazol-1-yl |
| 153 | —S-methyl | b = 0 | —CH=CH— | piperidin-4-yl |
| 154 | —S-methyl | b = 0 | —CH=CH— | pyrid-4-yl |
| 155 | —S-methyl | b = 0 | —CH=CH— | pyrid-2-yl |
| 157 | —S-methyl | b = 0 | —NH—C(O)— | 4-amino-piperidin-4-yl |
| 158 | —S-methyl | b = 0 | —NH—C(O)— | 4-methyl-piperidin-4-yl |
| 160 | —S-methyl | b = 0 | —C(O)—CH₂— | piperidin-4-yl |
| 161 | —S-methyl | b = 0 | —C(O)—CH₂— | piperidin-3-yl |
| 163 | —S-methyl | b = 0 | —C(O)—CH₂— | pyrrolidin-2-yl |
| 164 | —S-methyl | b = 0 | c = 0 | pyrid-4-yl |
| 165 | —S-methyl | b = 0 | —NH—CH₂CH₂— | piperazin-1-yl |
| 166 | —S-methyl | b = 0 | —NH—CH₂CH₂— | piperidin-4-yl |
| 167 | —S-methyl | b = 0 | —NH—C(O)— | 4-fluoro-piperidin-4-yl |
| 168 | —S-methyl | b = 0 | —C(O)—C(O)— | piperazin-1-yl |
| 171 | —S-methyl | b = 0 | —C(O)— | 1-methyl-benzimidazol-6-yl |
| 172 | —S-methyl | b = 0 | —NH—C(O)— | 4-(phenyl)-piperidin-4-yl |
| 173 | —S-methyl | 4-methoxy | —NH—C(O)— | 1-methyl-benzimidazol-5-yl |
| 174 | —S-methyl | b = 0 | —C(O)— | benzo[c][1,2,5]oxadiazol-5-yl |
| 175 | —S-methyl | b = 0 | —CH=CH— | pyrroldin-2-yl |
| 176 | —S-methyl | b = 0 | —CH=CH— | piperidin-3-yl |
| 178 | —S-methyl | b = 0 | —CH=CH— | 6-methyl-pyrid-3-yl |
| 179 | —S-methyl | 3-fluoro | c = 0 | 1,2,3,6-tetrahydropyrid-4-yl |
| 180 | —S-methyl | 2-methyl | c = 0 | 1,2,3,6-tetrahydropyrid-4-yl |
| 184 | —S-methyl | 4-methyl | c = 0 | 1,2,3,6-tetrahydropyrid-4-yl |
| 185 | —S-methyl | b = 0 | —CH₂CH₂— | piperidin-4-yl |

TABLE 2

Representative Compounds of Formula (I)

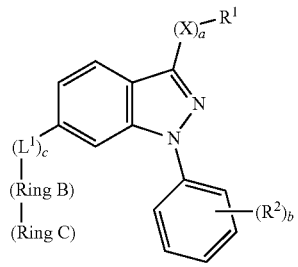

Y = CH, W = CH, R³ = H

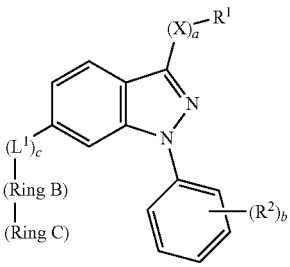

Y = CH, W = CH, R³ = H

| ID No. | —(X)ₐ—R¹ | (R²)ᵦ | (L¹)ᵧ | (Ring B) | (Ring C) |
|---|---|---|---|---|---|
| 15 | —S-methyl | b = 0 | c = 0 | azetidin-1-yl | 3-(piperazin-1-yl) |
| 19 | —S-methyl | b = 0 | c = 0 | pyrrolidin-1-yl | 3-(piperazin-1-yl) |
| 20 | —S-methyl | b = 0 | c = 0 | piperidin-1-yl | 4-(piperazin-1-yl) |
| 21 | —S-methyl | b = 0 | c = 0 | piperazin-1-yl | 4-(azetidin-3-yl) |
| 22 | —S-methyl | b = 0 | c = 0 | piperazin-1-yl | 4-(pyrrolidin-3-yl) |
| 23 | —S-methyl | b = 0 | c = 0 | piperazin-1-yl | 4-(piperidin-4-yl) |

TABLE 2-continued

Representative Compounds of Formula (I)

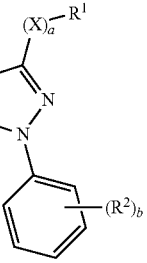

Y = CH, W = CH, R³ = H

| ID No. | —(X)ₐ—R¹ | (R²)ᵦ | (L¹)꜀ | (Ring B) | (Ring C) |
|---|---|---|---|---|---|
| 24 | —S-methyl | b = 0 | c = 0 | piperazin-1-yl | 4-(pyrid-2-yl) |
| 25 | —S-methyl | b = 0 | c = 0 | 1-imidazolidin-2-one | 3-(pyrrolidin-3-yl) |
| 26 | —S-methyl | b = 0 | c = 0 | 1-imidazolidin-2-one | 3-(piperidin-4-yl) |
| 29 | —S-methyl | b = 0 | c = 0 | piperazin-1-yl | 4-(pyrid-4-yl) |
| 36 | ethyl | b = 0 | c = 0 | piperidin-1-yl | 4-(piperazin-1-yl) |
| 41 | ethyl | b = 0 | —O— | azetidin-3-yl | 1-(piperidin-4-yl) |
| 43 | ethyl | b = 0 | c = 0 | pyrrolidin-1-yl | 3-(piperazin-1-yl) |
| 44 | ethyl | b = 0 | c = 0 | piperazin-1-yl | 4-(azetidin-3-yl) |
| 45 | ethyl | b = 0 | c = 0 | piperazin-1-yl | 4-(pyrrolidin-3-yl) |
| 46 | ethyl | b = 0 | c = 0 | piperazin-1-yl | 4-(piperidin-4-yl) |
| 47 | ethyl | b = 0 | c = 0 | piperazin-1-yl | 4-(pyrid-4-yl) |
| 48 | ethyl | b = 0 | c = 0 | 1-imidazolidin-2-one | 3-(pyrrolidin-3-yl) |
| 49 | ethyl | b = 0 | c = 0 | 1-imidazolidin-2-one | 3-(piperidin-4-yl) |
| 52 | ethyl | b = 0 | c = 0 | phenyl | 4-(piperazin-1-yl) |
| 53 | ethyl | b = 0 | c = 0 | phenyl | 4-(pyrrolidin-3-yl) |
| 57 | methyl | b = 0 | c = 0 | piperidin-1-yl | 4-(piperazin-1-yl) |
| 58 | methyl | b = 0 | c = 0 | phenyl | 4-(piperidin-4-yl) |
| 60 | methyl | b = 0 | c = 0 | azetidin-1-yl | 3-(piperazin-1-yl) |
| 61 | methyl | b = 0 | c = 0 | pyrrolidin-1-yl | 3-(piperazin-1-yl) |
| 62 | methyl | b = 0 | c = 0 | piperazin-1-yl | 4-(azetidin-3-yl) |
| 63 | methyl | b = 0 | c = 0 | piperazin-1-yl | 4-(pyrrolidin-3-yl) |
| 64 | methyl | b = 0 | c = 0 | piperazin-1-yl | 4-(piperidin-4-yl) |
| 65 | methyl | b = 0 | c = 0 | piperazin-1-yl | 4-(pyrid-4-yl) |
| 67 | methyl | b = 0 | c = 0 | 1-imidazolidin-2-one | 3-(piperidin-4-yl) |
| 73 | —O-methyl | b = 0 | c = 0 | azetidin-1-yl | 3-(piperazin-1-yl) |
| 74 | —O-methyl | b = 0 | c = 0 | piperazin-1-yl | 4-(azetidin-3-yl) |

TABLE 2-continued

Representative Compounds of Formula (I)

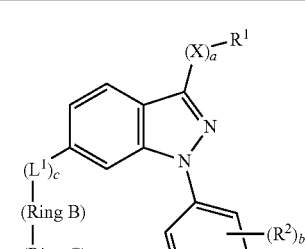

Y = CH, W = CH, R³ = H

| ID No. | —(X)ₐ—R¹ | (R²)ᵦ | (L¹)꜀ | (Ring B) | (Ring C) |
|---|---|---|---|---|---|
| 75 | —O-methyl | b = 0 | c = 0 | piperazin-1-yl | 4-(pyrrolidin-3-yl) |
| 76 | —O-methyl | b = 0 | c = 0 | piperazin-1-yl | 4-(piperidin-4-yl) |
| 77 | —O-methyl | b = 0 | c = 0 | piperazin-1-yl | 4-(pyrid-4-yl) |
| 78 | —O-methyl | b = 0 | c = 0 | phenyl | 4-(piperazin-1-yl) |
| 79 | —O-methyl | b = 0 | c = 0 | phenyl | 4-(imidazolyl-1-yl) |
| 81 | —O-methyl | b = 0 | c = 0 | 1-imidazolidin-2-one | 3-(piperidin-4-yl) |
| 106 | —S-methyl | 4-methoxy | c = 0 | piperazin-1-yl | 4-(piperidin-1-yl) |
| 119 | —S-methyl | 3-methyl | c = 0 | piperazin-1-yl | 4-(piperidin-4-yl) |
| 126 | —S-ethyl | 2,4-difluoro | c = 0 | piperazin-1-yl | 4-(piperidin-4-yl) |
| 135 | —S-methyl | 4-fluoro | c = 0 | piperazin-1-yl | 4-(piperidin-4-yl) |

TABLE 3

Representative Compounds of Formula (I)

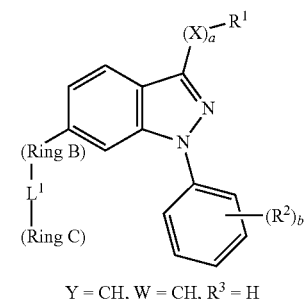

Y = CH, W = CH, R³ = H

| ID No. | —(X)ₐ—R¹ | (R²)ᵦ | (Ring B) | (L¹)꜀ | (Ring C) |
|---|---|---|---|---|---|
| 16 | —S-methyl | b = 0 | piperazin-1-yl | -4-C(O)— | piperidin-3-yl |
| 17 | —S-methyl | b = 0 | piperazin-1-yl | -4-C(O)— | pyrid-4-yl |

TABLE 3-continued

Representative Compounds of Formula (I)

Y = CH, W = CH, R³ = H

| ID No. | —(X)ₐ—R¹ | (R²)ᵦ | (Ring B) | (L¹)ᶜ | (Ring C) |
|---|---|---|---|---|---|
| 18 | —S-methyl | b = 0 | piperazin-1-yl | -4-CH₂— | pyrid-4-yl |
| 27 | —S-methyl | b = 0 | 1-imidazolidin-2-one | -3-CH₂— | pyrrolidin-3-yl |
| 28 | —S-methyl | b = 0 | 1-imidazolidin-2-one | -3-CH₂— | piperidin-3-yl |
| 30 | —S-methyl | b = 0 | piperazin-1-yl | -4-C(O)— | pyrid-2-yl |
| 31 | —S-methyl | b = 0 | piperazin-1-yl | -4-C(O)— | pyrid-3-yl |
| 32 | —S-methyl | b = 0 | piperazin-1-yl | -4-CH₂— | pyrid-3-yl |
| 33 | —S-methyl | b = 0 | piperazin-1-yl | -4-C(O)— | pyrrolidin-2-yl |
| 34 | —S-methyl | b = 0 | piperazin-1-yl | -4-C(O)— | piperidin-4-yl |
| 35 | —S-methyl | b = 0 | piperazin-1-yl | -4-C(O)— | piperidin-2-yl |
| 37 | ethyl | b = 0 | phenyl | -4-O— | piperidin-4-yl |

TABLE 4

Representative Compounds of Formula (I)

Y = N, Z = N, R² = H

| ID No. | —(X)ₐ—R¹ | R³ | (L¹)ᶜ | (Ring A) |
|---|---|---|---|---|
| 86 | methyl | OH | c = 0 | piperidin-4-yl |
| 91 | ethyl | OH | c = 0 | piperidin-4-yl |

TABLE 5

Representative Compounds of Formula (I)

Y = N, Z = N, R² = H

| ID No. | —(X)ₐ—R¹ | R³ | (L¹)ᶜ | (Ring B) | (Ring C) |
|---|---|---|---|---|---|
| 82 | ethyl | H | c = 0 | piperazin-1-yl | 4-(azetidin-3-yl) |
| 83 | ethyl | H | c = 0 | piperazin-1-yl | 4-(pyrid-3-yl) |
| 84 | methyl | OH | c = 0 | piperidin-4-yl | 1-(pyrid-3-yl) |
| 85 | methyl | OH | c = 0 | piperidin-3-yl | 1-(azetidin-3-yl) |
| 88 | methyl | OH | c = 0 | piperidin-4-yl | 1-(pyrrolidin-3-yl) |
| 89 | methyl | OH | c = 0 | piperidin-4-yl | 1-(piperidin-4-yl) |
| 90 | methyl | OH | —CH₂— | piperidin-4-yl | 1-(azetidin-3-yl) |
| 92 | ethyl | OH | c = 0 | piperidin-4-yl | 1-(pyrid-4-yl) |
| 93 | ethyl | OH | c = 0 | piperidin-4-yl | 1-(pyrid-3-yl) |
| 94 | ethyl | OH | c = 0 | piperidin-4-yl | 1-(pyrrolidin-3-yl) |
| 95 | ethyl | OH | c = 0 | piperidin-4-yl | 1-(piperidin-4-yl) |

TABLE 6

Representative Compounds of Formula (I)

Y = N, Z = N, R² = H

| ID No. | —(X)ₐ—R¹ | R³ | (Ring B) | (L¹)ᶜ | (Ring C) |
|---|---|---|---|---|---|
| 87 | methyl | OH | piperidin-4-yl | -1-C(O)— | piperidin-4-yl |
| 96 | ethyl | OH | piperidin-4-yl | -1-C(O)— | piperidin-4-yl |

TABLE 7

Representative Compounds of Formula (I)

Y = CH, Z = N, R² = H

| ID No. | —(X)ᵃ—R¹ | R³ | (L¹)c | (Ring B) | (Ring C) |
|---|---|---|---|---|---|
| 97 | methyl | OH | c = 0 | phenyl | 4-(piperazin-1-yl) |
| 98 | ethyl | —O-methyl | c = 0 | phenyl | 4-(3,5-dimethyl-piperazin-1-yl) |
| 99 | methyl | —O-methyl | c = 0 | phenyl | 4-(piperiazin-1-yl) |
| 102 | ethyl | —O-ethyl | c = 0 | phenyl | 4-(piperazin-1-yl) |
| 103 | ethyl | —O-ethyl | c = 0 | phenyl | 4-(4-methyl-piperazin-1-yl) |
| 104 | ethyl | —O-ethyl | c = 0 | phenyl | 4-(3,5-dimethyl-piperazin-1-yl) |

TABLE 8

Representative Compounds of Formula (I)

Y = CH, Z = N, R² = H

| ID No. | —(X)ᵃ—R¹ | R³ | (Ring B) | L¹ | (Ring C) |
|---|---|---|---|---|---|
| 100 | ethyl | OH | phenyl | -4-NH— | piperidin-4-yl |
| 101 | methyl | OH | phenyl | -4-NH— | piperidin-4-yl |

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, the prefix "$C_{X-Y}$" when used with alkyl shall mean a carbon chain composition of between X and Y carbon atoms, inclusively. For example, the term "$C_{1-4}$alkyl" shall mean a carbon chain composition of between 1-4 carbon atoms. One skilled in the art will recognize that the term "—($C_{1-4}$alkyl)-" shall denote any $C_{1-4}$alkyl carbon chain as herein defined, wherein said $C_{1-4}$alkyl chain is divalent and is further bound through two points of attachment, preferably through two terminal carbon atoms.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —$CF_3$, —$CH_2$—$CF_3$, —$CF_2$—$CF_2$—$CF_3$, —$CCl_3$, —$CH_2CCl_3$, and the like. Similarly, unless otherwise noted, the term "fluorinated $C_{1-4}$alkyl" shall mean any $C_{1-4}$alkyl group as defined above substituted with at least one fluoro atom. Suitable examples include but are not limited to —$CF_3$, —$CH_2$—$CF_3$, —$CF_2$—$CF_2$—$CF_3$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, the prefix "$C_{X-Y}$" when used with alkoxy shall mean an oxygen ether radical composition of between X and Y carbon atoms, inclusively. For example, the term "$C_{1-4}$alkoxy" shall mean an oxygen ether radical composition of between 1-4 carbon atoms.

As used herein, unless otherwise noted, the term "4 to 10 membered, nitrogen containing ring structure" shall mean any 4 to 10 membered ring structure, wherein the ring structure contains at least one nitrogen atom preferably, one to three nitrogen atoms, more preferably one to two nitrogen atoms; and wherein the 4 to 10 membered nitrogen containing ring structure further, optionally, contains one to two, preferably one, additional heteroatom independently selected from the group consisting of O and S. Additionally, said 4 to 10 membered nitrogen containing rings structure may be monocyclic, bicyclic, bridged or spiro-fused; and further, may be saturated, partially unsaturated or aromatic. The 4 to 10 membered nitrogen containing ring structure may be attached at any heteroatom or carbon atom of the ring such that the result is a stable structure. Wherein the 4 to 10 membered nitrogen containing ring structure is bound through a carbon atom, the ring nitrogen atom may be optionally substituted with an oxo group. Suitably examples of 4 to 10 membered nitrogen containing ring structures include, but are not limited to piperidinyl, piperazinyl, morpholinyl, pyrrolidinyl, azetidinyl, diazepanyl, tetrahydropyridyl, pyrazolyl, pyridyl, triazolyl, benzimidazolyl, benzo[c][1,2,5]oxadiazlyl, 2,5-diazabicyclo[2.2.1]-heptyl, octahydropyrrolo[3,4-c]pyrrolyl, 2,7-diazaspiro[4.4]nonayl, 1-imidazolidin-2-one, isoindolyl-1,3-dione, and the like.

When a particular group is "substituted" (e.g., alkyl, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

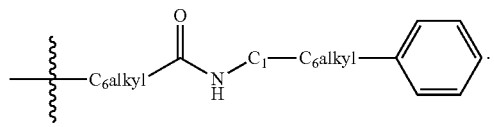

Abbreviations used in the specification, particularly the Schemes and Examples, are as follows:

| | |
|---|---|
| Ac = | Acetyl group (—C(O)—CH$_3$) |
| AcOH = | Acetic Acid |
| ATP = | Adenosine Tri-Phosphate |
| BINAP = | 2,2'-Bis(diphenylphosphino)-1,1'-binaphthalene |
| Boc = | tert-Butoxycarbonyl (i.e. —C(O)O—C(CH$_3$)$_3$) |
| BOP = | Benzotriazol-1-yloxy)tris(dimethylamino)phosphonium hexafluorophosphate |
| B(OEt)$_3$ = | Triethyl Borate |
| B(OPr)$_3$ = | Tripropyl Borate |
| BuOH = | Butanol |
| t-BuOK = | Potassium tert-Butoxide |
| t-BuONa = | Sodium tert-Butoxide |
| n-BuLi = | n-Butyl Lithium |
| Bu$_3$P = | Tri-n-butylphosphine |
| CSA = | Camphor sulfonic acid |
| Cu(OAc)$_2$ = | Copper Acetate |
| DCM = | Dichloromethane |
| DEAD = | Diethylazodicarboxylate |
| DIAD = | Diisopropylazodicarboxylate |
| DIC = | N,N-Diisopropylcarbodiimide |
| DIPEA or DIEA = | Diisopropylethylamine |
| DME = | 1,2-Dimethoxyethane |
| DMF = | Dimethyl formamide |
| DMSO = | Dimethylsulfoxide |
| dppf = | 1,1'-Bis(diphenylphosphino)ferrocene |
| EDCl or EDC•HCl = | 1-(3-Dimethylaminopropyl)-3-ethylcarbodiimide hydrochloride |
| Et = | Ethyl (i.e. —CH$_2$CH$_3$) |
| Et$_2$O = | Diethyl ether |
| EtOAc = | Ethyl acetate |
| EtOH = | Ethanol |
| EtONa = | Sodium Ethoxide |
| FA = | Fatty acid |
| FFA = | Free fatty acid |
| HATU = | O-(7-Azabenzotriazol-1-yl)-N,N,N',N'-tetramethyluronium hexafluorophosphate |
| HPLC = | High pressure liquid chromatography |
| IPA = | Isopropyl alcohol |
| Josiphos Ligand = | (R)-1-[(S)-(2-diphenylphosphino)ferrocenyl]ethyldicyclohexylphosphine |
| KHK = | Ketohexokinase |
| LDA = | Lithium Diisopropylamide |
| LHMDS or LiHMDS or (TMS)$_2$NLi or LiN(TMS)$_2$ = | Lithium Hexamethyldisilazinamide |
| Lindar's Reagent = | Palladium 5% on calcium carbonate, partially poisoned with lead |
| mCPBA = | m-Chloroperbenzoic acid |
| MeOH = | Methanol |
| MOM = | Methoxymethyl ether |
| Ms = | Methanesulfonyl |
| MsCl = | Mesyl Chloride |
| MTBE = | Methyl tert-Butyl Ether |
| NBu$_3$ = | Tributylamine |
| NH$_4$OAc = | Ammonium Acetate |
| NIDDM = | Non-insulin dependent Diabete |
| NMP = | N-methylpyrrolidinone |
| OMs = | Methanesulfonyl ester |
| OTs = | Toluene-4-sulfonyl ester |
| PBu$_3$ = | Tributyl Phosphine |
| PdCl$_2$(dppf) = | [1,1'-Bis(diphenylphosphino)ferrocene]dichloropalladium(II) |
| Pd$_2$(dba)$_3$ = | Dipalladium tris[μ-[(1,2-η: 4,5-η)-(1E,4E)-1,5-diphenyl-1,4-pentadien-3-one]] |
| Pd(OAc)$_2$ = | Palladium Acetate |
| Pd(PPh$_3$)$_4$ or Pd(Ph$_3$P)$_4$ = | Palladium Tetrakis(triphenylphosphine) |
| Ph = | Phenyl |
| P(Ph)$_3$ = | Triphenylphosphine |
| PPA = | Polyphosphoric acid |
| pTSA = | p-Toluene sulfonic acid |
| Raney Nickel = | Aluminium-nickel alloy |
| TEA or Et$_3$N = | Triethylamine |
| TFA = | Trifluoroacetic acid |
| TG = | Triglyceride |
| THF = | Tetrahydrofuran |
| THP = | Tetrahydropyran |
| TMS = | Trimethylsilyl |
| Ts = | Toluene-4-sulfonyl |
| TSA•H$_2$O = | p-Toluenesulfonic acid monohydrate |
| TZD = | Thiazolidinedione |
| VLDL = | Very low density lipoprotein |
| Xantphos = | 4,5-Bis(diphenylphosphino)-9,9-dimethylxanthene |

Ketohexokinase mediated disaease and/or disorders include, but are not limited to, obesity, elevated glucose levels, glucose intolerance, insulin resistance, Type I diabetes mellitus, Type II diabetes mellitus, Metabolic Syndrome X, elevated triglycerides, hyperlipidemia and hypertension. Preferably, the ketohexokinase mediated disorder is selected from the group consisting of obesity, Type II diabetes mellitus and Metabolic Syndrome X.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

As used herein, the term "co-therapy" shall mean treatment of a subject in need thereof by administering one or more compounds of formula I with other pharmaceutical active agents, wherein the compound(s) of formula I and other pharmaceutically active agents are administered by any suitable means, simultaneously, sequentially, separately or in a single pharmaceutical formulation. Where the compound(s) of formula I and other pharmaceutically active agents are administered in separate dosage forms, the number of dosages administered per day for each compound may be the same or different. The compound(s) of formula I and other pharmaceutically active agents may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The compound(s) of formula I and other pharmaceutically active agents may be administered according to simultaneous or alternating regimens, at the same or different times during the course of the therapy, concurrently in divided or single forms.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

In the Schemes which follow herein, the variable $A^X$, wherein X is an integer, are used to denote leaving or activating groups. The selection of a particular $A^X$ group on a given compound or intermediate is not intended to limit the selection of said $A^X$ group on any other compound or intermediate.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivative—groups of the formula —SO$_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha\text{-}obs]/[\alpha\text{-max}]) \times 100.$$

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

General Synthetic Schemes

Compounds of formula (I) may be prepared according to the process as described in the Scheme 1, below.

Scheme 1

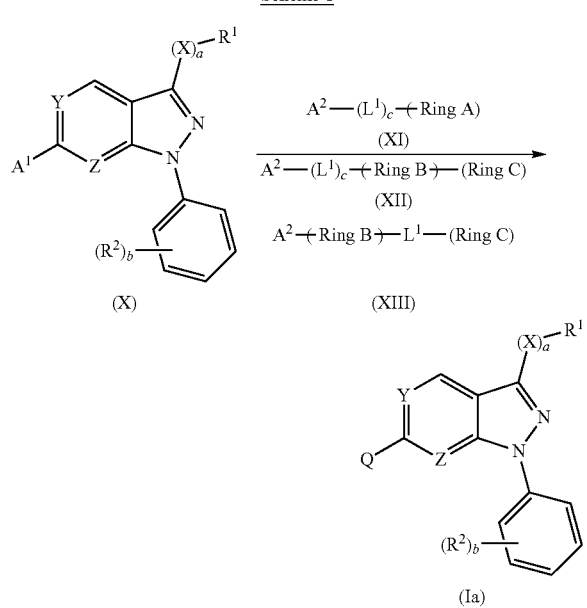

Accordingly, a suitably substituted compound of formula (X), wherein $A^1$ a suitably selected leaving group such as a halogen such as Cl, Br, I, and the like, a known compound or compound prepared by known methods, is reacted with a suitably substituted compound of formula (XI) or a suitably substituted compound of formula (XII) or a suitably substituted compound of formula (XIII), wherein $A^2$ is hydrogen and wherein (Ring A) or (Ring B) contains a secondary amine, a known compound or compound prepared by known methods;

in an inorganic base such as t-BuOK, t-BuONa, $Cs_2CO_3$, and the like, in the presence of a suitably selected Pd containing reagent such $Pd(OAc)_2$, $Pd(Ph_3P)_4$, $PdCl_2$, and the like, in the presence of a suitably selected ligand such as $Ph_3P$, BINAP, dppf, and the like, in a mixture of a suitably selected organic solvent such as THF, 1,4-dioxane, and the like, and water, to yield the corresponding compound of formula (Ia).

Alternatively, a suitably substituted compound of formula (X) wherein $A^1$ is a suitably selected leaving group such as a halogen such as Cl, Br, I, and the like, a known compound or compound prepared by known methods, is reacted with a suitably substituted compound of formula (XI) or a suitably substituted compound of formula (XII) or a suitably substituted compound of formula (XIII), wherein $A^2$ is boronic acid (i.e. $-B(OH)_2$) or a boronic ester (for example,

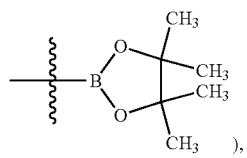

a known compound or compound prepared by known methods, in the presence of an inorganic base such as $Na_2CO_3$, $K_2CO_3$, $K_3PO_4$, and the like, in the presence of a suitably selected an Pd containing reagent such $Pd(OAc)_2$, $Pd(Ph_3P)_4$, $PdCl_2$, and the like, in the presence of a suitably selected ligand such as $Ph_3P$, BINAP, dppf, and the like, in a mixture of a suitably selected organic solvent such as toluene, 1,4-dioxane, and the like, and water, to yield the corresponding compound of formula (Ia).

Alternatively, a suitably substituted compound of formula (X), wherein $A^1$ is OH, is reacted with a suitably substituted compound of formula (XI) or a suitably substituted compound of formula (XII), wherein $A^2$ is a suitably selected leaving group such as $-OTs$, $-OMs$, Br, and the like; in the presence of an inorganic base such as NaH, $Cs_2CO_3$, $K_2CO_3$, and the like, in an organic solvent such as DMSO, THF, DMF, 1,4-dioxane, and the like, at a temperature in the range of from about 25° C. to about 100° C., to yield the corresponding compound of formula (Ia), wherein Q is selected from the group consisting of $-L^1$-(Ring A) and $-L^1$-(Ring B)-(Ring C) and wherein $L^1$ is selected from the group consisting of $-O-$ and $-O-CH_2-$.

Alternatively, a suitably substituted compound of formula (X), wherein $A^1$ is $NH_2$, is reacted with a suitably substituted compound of formula (XI) or a suitably substituted compound of formula (XII), w wherein $A^2$ is a suitably selected carboxy containing group such as carboxylic chloride, isocyanate, and the like; in the presence of an organic base such as TEA, DIPEA, pyridine, and the like, in an organic solvent such as DCM, THF, DMF, 1,4-dioxane, and the like, at a temperature in the range of from about 0° C. to about 70° C., to yield the corresponding compound of formula (Ia), wherein Q is selected from the group consisting of $L^1$-(Ring A) and $L^1$-(Ring B)-(Ring C) and wherein $L^1$ is selected from the group consisting of carboxamide or urea.

One skilled in the art will recognize that compounds of formula (I) wherein Q contains other $L^1$ groups may be similarly prepared, according to known methods.

Compounds of formula (I) may alternatively be prepared according to the process outlined in Scheme 2, below.

Scheme 2

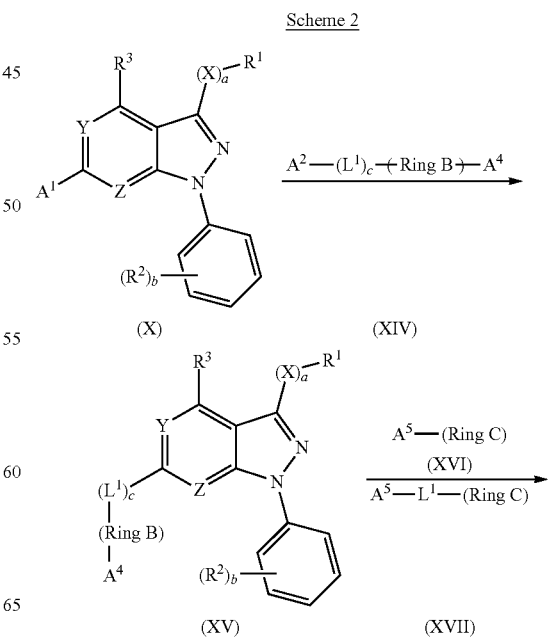

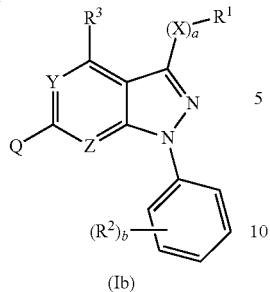

(Ib)

Accordingly, a suitably substituted compound of formula (X), wherein $A^1$ is a suitably selected leaving group such as a halogen such as Cl, Br, I, and the like, a known compound or compound prepared by known methods is reacted with a suitably substituted compound of formula (XIV) or a suitably substituted compound (XV), wherein $A^3$ is hydrogen, when c=0 and (Ring B) contains a secondary amine group, or wherein $A^3$ is a boronic acid (i.e. —B(OH)$_2$) or a boronic ester (for example,

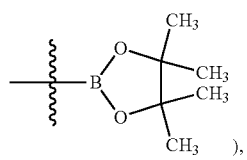), and the like; a known compound or compound prepared by known methods, according to the process as described in Scheme 1 above (more particularly under the conditions as described for the reaction for a suitably substituted compound of formula (X) with a suitably substituted compound of formula (XI), (XII) or (XIII)); to yield the corresponding compound of formula (XV).

The compound of formula (XV) is reacted with a suitably substituted compound of formula (XVI) or when in the compound of formula (XV) c=0, with a suitably substituted compound of formula (XVII), wherein $A^5$ is a suitably selected leaving group such as Br, Cl, OMs, and the like, a known compound or compound prepared by known methods, according to the process as described in Scheme 1 above (more particularly under the conditions as described for the reaction for a suitably substituted compound of formula (X) with a suitably substituted compound of formula (XI), (XII) or (XIII)); to yield the corresponding compound of formula (Ia), wherein Q is selected from the group consisting of -($L^1$)$_c$-(Ring B)-(Ring C) and -(Ring B)-$L^1$-(Ring C).

Compounds of formula (I) wherein Y is CH and Z is CH; and compounds of formula (I) wherein Y is CH and Z is N; may alternatively be prepared according to the process outlined in Scheme 3, below.

Scheme 3

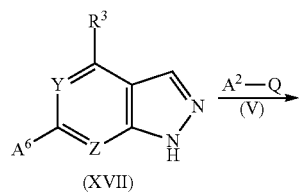

(XVII)

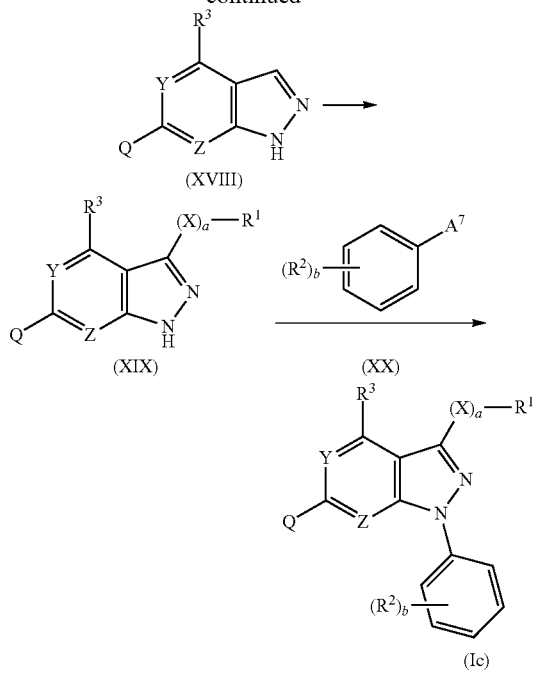

Accordingly, a suitably substituted compound of formula (XVII), wherein $A^6$ is a suitably selected leaving group such as a halogen such as Cl, Br, I, and the like, a known compound or compound prepared by known methods, is reacted with a suitably substituted compound of formula (V), wherein $A^2$ is a suitably selected group such as hydrogen (wherein c=0 and the (Ring A) or (Ring B) contains a secondary amine), or $A^2$ is a suitably selected leaving group such as boronic acid, a boronic acid ester, hydroxy, amino, and the like, a known compound or compound prepared by known methods, according to the processes as described in Scheme 1, above; to yield the corresponding compound of formula (XVIII).

The compound of formula (XVIII) is reacted to yield the corresponding compound (XIX). For example, the compound of formula (XVIII) may be reacted with I$_2$, in the presence of a suitably selected base such as KOH, NaOH, t-BuOK, and the like, in a suitably selected organic solvent such as DMF, DMSO, NMP, and the like, to yield the corresponding intermediate wherein an iodo group is attached at the desired $R^3$ position; followed by reacting the iodo-substituted intermediate with a suitably selected nuclophile such as Na—S—$R^1$, Na—O—$R^1$, K—S—$R^1$, Li—S—$R^1$, and the like; in the presence of a suitably selected Pd agent such as Pd(OAc)$_2$, PdCl$_2$(dppf), Pd(Ph$_3$P)$_4$, and the like; in the presence of a suitably selected ligand such as Josiphos, BINAP, Xantphos, and the like; in a suitably selected organic solvent such as DME, DMF, 1,4-dioxane, and the like; to yield the corresponding compound of formula (XIX).

The compound of formula (XIX) is reacted with a suitably substituted compound of formula (XX), wherein $A^7$ is a suitably selected leaving group such as boronic acid or a suitably selected boronic ester, a known compound or compound prepared by known methods, in the presence of a catalyst such as Cu(OAc)$_2$, CuCl$_2$, CuBr$_2$, and the like; in the presence of a suitably selected organic base such as TEA, DIPEA, pyridine, and the like; in a suitably selected organic solvent such as DCM, THF, dichloroethane, and the like; to yield the corresponding compound of formula (Ic).

One skilled in the art will recognize that wherein Q is selected from the group consisting of -(L¹)$_c$-(Ring B)-(Ring C) and -(Ring B)-L¹-(Ring C), said Q group may alternatively be attached to the indazole core via a two-step process, for example, applying the procedures as described in Scheme 2, above.

Compounds of formula (X) wherein Y is CH, Z is CH, a=1 and X is O or S may be prepared according to the process as outlined in Scheme 4, below.

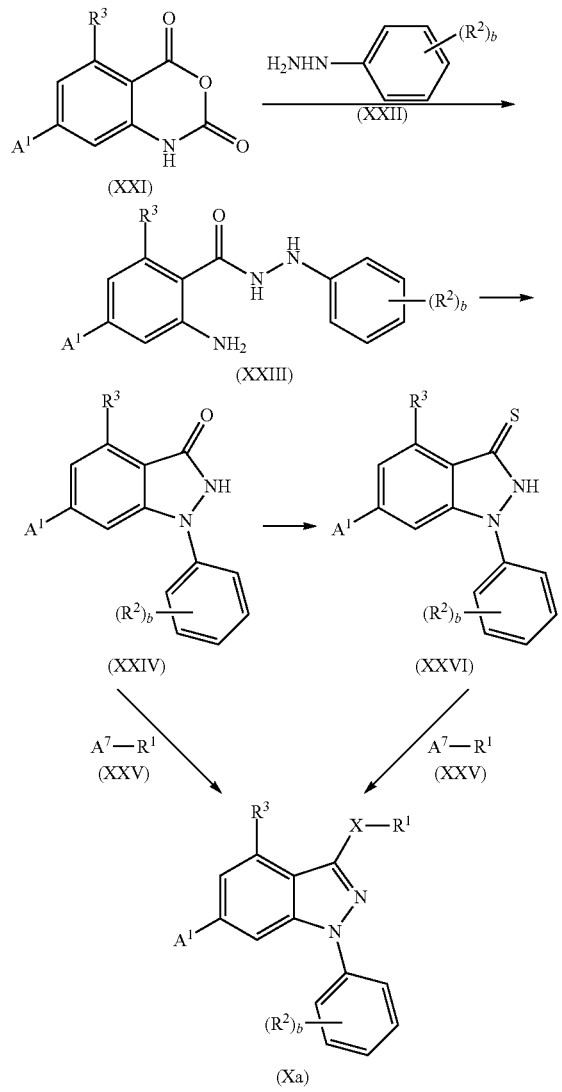

Accordingly, a suitably substituted compound of formula (XXI) wherein A¹ is a suitably selected group such as Cl, Br, I, NO$_2$, NH$_2$, and the like, a known compound or compound prepared by known methods, is reacted with a suitably substituted compound of formula (XXII), a known compound or compound prepared by known methods, in the presence of an organic base such as TEA, pyridine, DIPEA, N-ethyl-N-isopropylpropan-2-amine, and the like, in an organic solvent such as THF, 1,4-dioxane, DMF, and the like, at a temperature in the range of from about 0 to about 80° C., to yield the corresponding compound of formula (XXIII).

The compound of formula (XXIII) is reacted with inorganic reagent such as NaNO$_2$, KNO$_2$, NH$_4$NO$_2$ and the like, in the presence of an inorganic acid such as concentrated HCl, sulfuric acid and the like, in a mixture of a suitably selected organic solvent such as MeOH, EtOH, IPA, and the like and water, at a temperature in the range of from about 0° C. to about 80° C., to yield the corresponding compound of formula (XXIV).

The compound of formula (XXIV) is reacted with a suitably selected compound of formula (XXV), wherein A⁷ is a suitable leaving group such as I, Br, OMs, and the like, a known compound of compound prepared by known methods, for example the compound of formula (VI) is a suitably selected alkylating agent such as CH$_3$I, CH$_3$CH$_2$I, (CH$_3$)$_2$SO$_4$, and the like, in the presence of an inorganic base such as Na$_2$CO$_3$, K$_2$CO$_3$, Cs$_2$CO$_3$, and the like, in a solvent such as acetonitrile, THF, 1,4-dioxane, and the like, at a temperature in the range of from about 0° C. to about 80° C., to yield the corresponding compound of formula (Xa), wherein X is O.

Alternatively, the compound of formula (XXIV) is reacted with a sulfur containing reagent such as P$_2$S$_5$, Lawesson's agent, and the like in an organic solvent such as toluene, xylene chlorobenzene and the like, at an elevated temperature in the range of about 100 to about 180° C., to yield the corresponding compound of formula (XXVI).

The compound of formula (XXVI) is reacted with a suitably selected compound of formula (XXV), wherein A⁷ is a suitable leaving group such as 1, Br, OMs, and the like, a known compound of compound prepared by known methods, for example, the compound of formula (VI) is a suitably selected alkylating agent such as CH$_3$I, CH$_3$CH$_2$I, (CH$_3$)$_2$SO$_4$, and the like, in the presence of an inorganic base such as Na$_2$CO$_3$, K$_2$CO$_3$, Cs$_2$CO$_3$, and the like, in a solvent such as acetonitrile, THF, 1,4-dioxane, and the like, at a temperature in the range of from about 0° C. to about 80° C., to yield the corresponding compound of formula (Xa) wherein X is S.

Compounds of formula (X) wherein Y is CH, Z is CH, and a=0 (i.e. X is absent) may be prepared according to the process outlined in Scheme 5, below.

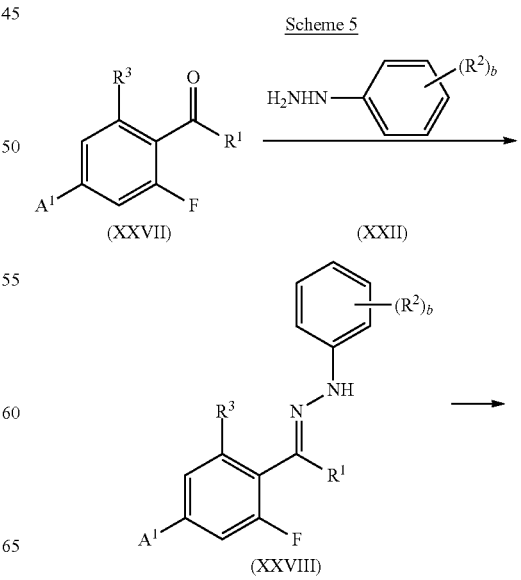

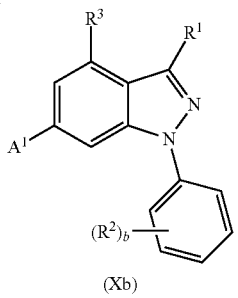

(Xb)

Accordingly, a suitably substituted compound of formula (XXVII), wherein $A^1$ is a suitable leaving group such as I, Br, OMs, and the like, a known compound or compound prepared by known methods, is reacted with a suitably substituted compound of formula (XXII), a known compound or compound prepared by known methods, in the presence of an organic acid such as pTSA, CSA, and the like, in an organic solvent such as MeOH, EtOH, IPA, and the like, at a temperature in the range of from about 25° C. to about 80° C., to yield the corresponding compound of formula (XXVIII).

The compound of formula (XXVIII) is reacted with a suitably selected inorganic base such as $K_2CO_3$, $Cs_2CO_3$, NaH, and the like, in an organic solvent such as DMF, DMSO or NMP, and the like at a temperature in the range of from about 25° C. to about 80° C., to yield the corresponding compound of formula (Xb).

One skilled in the art will recognize that compounds of formula (Xb), wherein $A^1$ is $NH_2$, may be prepared from the corresponding compound of formula (Xb) wherein $A^1$ is a halogen, by reacting with benzhydrylideneamine, in the presence of an inorganic base such as $K_2CO_3$, $Cs_2CO_3$, $Na_2CO_3$, and the like, in the presence of a suitably selected Pd containing reagent such as $Pd(OAc)_2$, $Pd(Ph_3P)_4$, $PdCl_2$, and the like, in the presence of a suitably selected ligand such as Xantphos, BINAP, dppf, and the like in an organic solvent such as DMF, 1,4-dioxane, toluene, and the like, at a temperature in the range of from about 80° C. to about 120° C., to yield the corresponding intermediate, which is then hydrolyzed according to known methods, for example by treatment with an inorganic acid such 3 N HCl, 1N $H_2SO_4$, and the like, to yield the corresponding compound of formula (Xb) wherein $A^1$ is $NH_2$.

Alternatively, compounds of formula (Xb), wherein $A^1$ is $NH_2$ may be prepared from the corresponding compound of formula (Xb) wherein $A^1$ is a halogen by reacting with a suitably selected inorganic base such as n-BuLi, LDA, LiHMDS, and the like, in an organic solvent such as THF, 1,4-dioxane, $Et_2O$, and the like, at a reduced temperature in the range of from about −80° C. to about 0° C., to yield the corresponding intermediate which is then reacted with a suitably selected boronic ester such as $B(OEt)_3$, $B(OPr)_3$, 4,4,5,5,4',4',5',5'-octamethyl-[2,2']bi[[1,3,2]dioxaborolanyl], and the like, to yield the corresponding boronic acid intermediate, which is then reacted with a suitably selected oxidizing agent such as $H_2O_2$, mCPBA, and the like, in an organic solvent such as THF, EtOAc, and the like, at a temperature in the range of from about 0° C. to about 25° C., to yield the compound of formula (Xb) wherein $A^1$ is $NH_2$.

Compounds of formula (I) wherein Y is N, Z is N, and a=0 (i.e. X is absent) may be prepared according to the process outlined in Scheme 6, below.

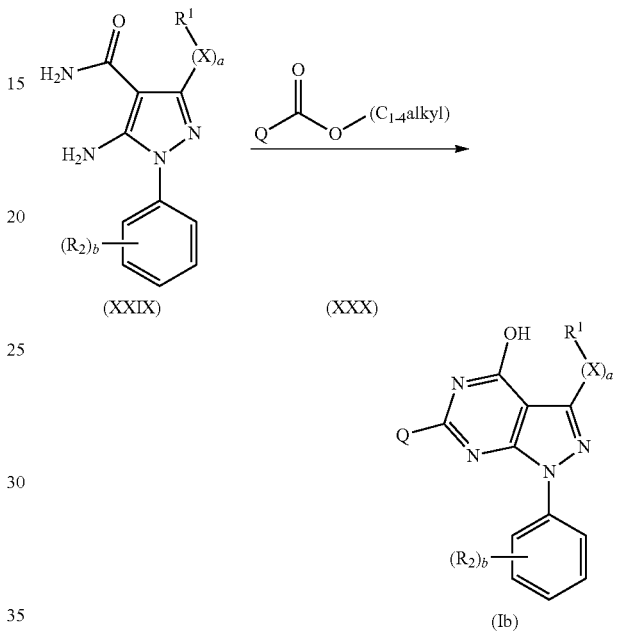

Scheme 6

Accordingly, a suitably substituted compound of formula (XXIX), a known compound or compound prepared by known methods, is reacted with a suitably substituted compound of formula (XXX), a known compound or compound prepared by known methods, in the presence of an organic base such as EtONa, t-BuONa, NaH, and the like, in an organic solvent such as n-BuOH, IPA, EtOH, and the like, at a temperature in the range of from about 80° C. to about 120° C., to yield the corresponding compound of formula (Ib).

Compounds of formula (I) wherein Y is N and Z is N may be prepared according to the process outlined in Scheme 7, below.

Scheme 7

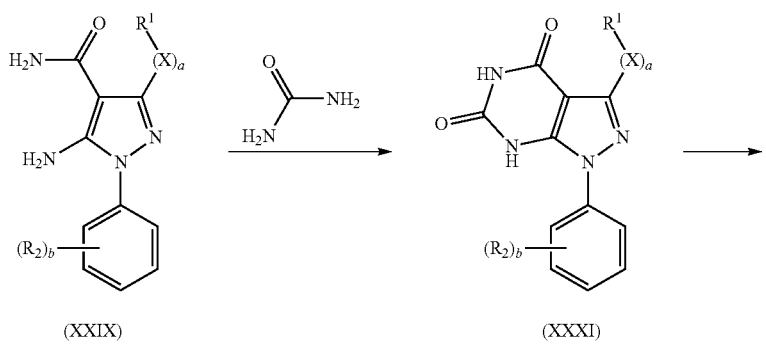

-continued

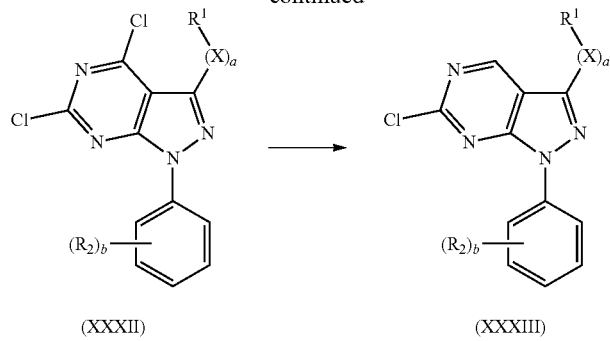

(XXXII)        (XXXIII)

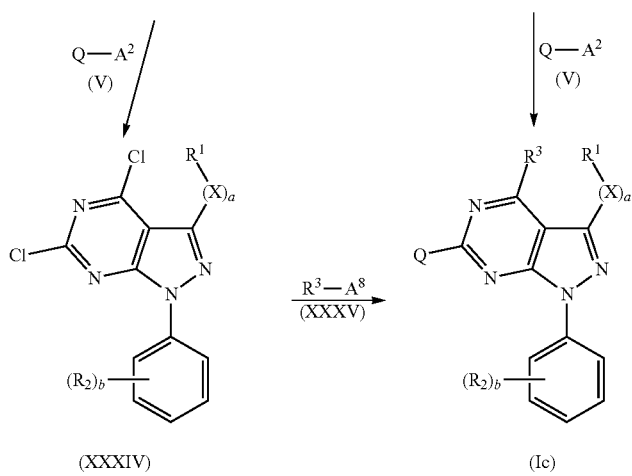

(XXXIV)        (Ic)

Accordingly, a suitably substituted compound of formula (XXIX), a known compound or compound prepared by known methods, is reacted with urea, a known compound, at a temperature in the range of from about 150° C. to about 220° C., to yield the corresponding compound of formula (XXXI).

The compound of formula (XXXI) is reacted with a suitably selected chlorinating agent such as as $PCl_5$, $POCl_3$, $SOCl_2$, and the like, in an organic solvent such as toluene, xylene, 1,4-dioxane, and the like at a temperature in the range of from about 80° C. to about 120° C.; to yield the corresponding compound of formula (XXXII).

The compound of formula (XXXII) is reacted with a suitably selected reducing agent such as Zn, Sn, and the like, in a solvent such as ammonia with NaCl, and the like, at a temperature in the range of from about 80° C. to about 120° C., to yield the compound of formula (XXXIII).

The compound of formula (XXXIII) is reacted with a suitably substituted compound of formula (V), according to the methods as described in Scheme 1 above, to yield the corresponding compound of formula (Ic), wherein $R^3$ is hydrogen.

Alternatively, the compound of formula (XXXII) is reacted with a suitably substituted compound of formula (V), according to the methods, as described in Scheme 1 above, to yield the corresponding compound of formula (XXXIV).

The compound of formula (XXXIV) is reacted with a suitably substituted compound of formula (XXXV), wherein $A^8$ is H and $R^3$ is nitrogen or oxygen containing group such as $N(C_{0-4}alkyl)_2$, $-O-C_{0-4}alkyl$, and the like, according to the processes as described in Scheme 1 above, to yield the corresponding compound of formula (Ic), wherein $R^3$ is other than hydrogen.

Compounds of formula (I) wherein Y is CH, Z is N, may be prepared according to the process as outlined in Scheme 8 below.

Scheme 8

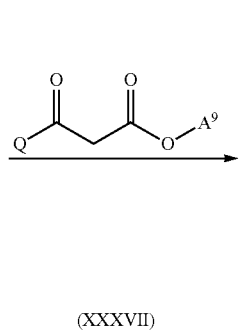

(XXXVI)        (XXXVII)

(Id)

Accordingly, a suitably substituted compound of formula (XXXVI), a known compound or compound prepared by known methods, is reacted with a suitably substituted compound of formula (XXXVII), wherein $A^9$ is $C_{1-4}$alkyl, a known compound or compound prepared by known methods, in the presence of an organic acid such as pTSA, CSA, PPA and the like, in an organic solvent such as toluene, xylene, benzene, and the like, at a temperature in the range of about 80° C. to about 120° C., to yield the corresponding compound of formula (Id).

The compound of formula (Id) may be further optionally reacted according to known methods, to yield the corresponding compound of formula (Id) wherein the hydroxy group is converted to other $R^3$ groups. For example, the compound of formula (Id) wherein $R^3$ is hydroxy may be reacted with a suitably selected $C_{1-4}$alkylating agent such as methanol, ethanol, and the like, in the presence of a suitably selected coupling reagent such as DEAD, DIAD, and the like, in the presence of a suitably selected ligand such as $Ph_3P$, $Bu_3P$, and the like, in an organic solvent such as THF, DCM, 1,4-dioxane, and the like, at a temperature in the range of from about 0° C. to about 50° C., to yield the corresponding compound of formula (Id) wherein the OH group is converted to the corresponding —O—($C_{1-4}$alkyl) group.

One skilled in the art will further recognize that wherein Q is selected from the group consisting of -($L^1$)$_c$-(Ring B)-(Ring C) and -(Ring B)-(Ring C), said Q group may be attached to the compound of formula (XXXVI) via a two-step process. For example, the compound of formula (XXXVI) may be reacted with a compound of the formula $A^{10}$-C(O)—$CH_2$—C(O)-($L^1$)$_c$-(Ring B)-$A^{11}$, wherein $A^{10}$ is $C_{1-4}$alkyl and $A^{11}$ is a suitably selected leaving group such as Cl, Br, and the like, according to known methods, for example as described in Scheme 2 above, to yield the corresponding intermediate, a compound of formula (XXXVIII)

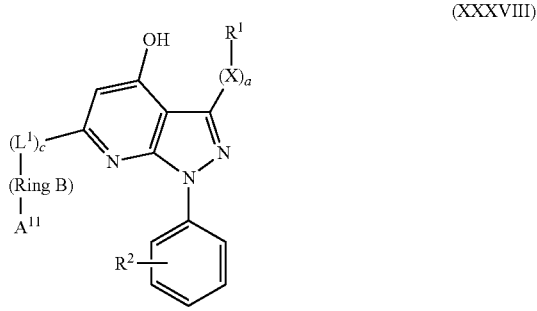

(XXXVIII)

which compound of formula (XXXVIII) is then reacted with a suitably substituted compound of formula $A^{12}$-($L^1$)$_c$-(Ring C), wherein $A^{12}$ is a suitably selected leaving group such as Cl, OTs, OMs, and the like, according to known methods, for example, as described in Schemes 2 above, to yield the corresponding compound of formula (Id), wherein $R^3$ is hydroxy (which compound may be further reacted as herein described to yield the corresponding compound of formula (Id), wherein $R^3$ is other than hydroxy).

One skilled in the art will recognize that in the preparation of the compounds of formula (I) of the present invention, the coupling of the Q group onto the indazole core may be achieved via a one step or two step process, as described in the Schemes above and in the Examples which follow herein. Wherein Q is selected from the group consisting of -($L^1$)$_c$-(Ring B)-(Ring C) and -(Ring B)-$L^1$-(Ring C), the two step preparation may include application of coupling reactions known to those skilled in the art, including but not limited to, metal mediated coupling (e.g. Suzuki coupling), peptide coupling, reductive amination, nucleopillic displacement, acylation, and other known processes. The Examples which follow herein provide additional specific examples of coupling processes for attaching a desired Q group to the indazole core, in the synthesis of the compounds of formula (I) of the present invention. One skilled in the art will recognize that the processes exemplified herein may be adapted to couple different Q groups onto the indazole core, and will further recognize the modifications necessary to achieve the desired Q group to indazole core coupling.

Pharmaceutical Compositions

The compounds of formula (I) of the present invention are useful in the treatment of disorders mediated by ketohexokinase, as may be determined, for example, according to the procedures described in the Biological Example, which follows herein. The present invention therefore provides a method of treating disorders mediated by ketohexokinase comprising administering to a subject in need thereof a therapeutically effective amount of any of the compounds of formula (I) as herein defined. In an example, a compound of formula (I) is administered in a therapeutically effective amount in the range of from about 0.01 mg/kg body weight to about 20 mg/kg body weight, or any amount or range therein.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 to about 1500 mg or any amount or range therein, and may be given at a dosage of from about 0.01 to about 100 mg/kg/day, or any amount or range therein, preferably from about 0.01 to about 20 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 to about 1000 mg of the active ingredient of the present invention, or any amount r range therein. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating KHK disorders described in the present invention may also be carried out using a pharmaceutical composition comprising any of the compounds as defined herein and a pharmaceutically acceptable carrier. The pharmaceutical composition may contain between about 0.01 mg and 1000 mg of the compound, or any amount or range therein; preferably about 0.5 to 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by KHK is required.

The daily dosage of the products may be varied over a wide range from about 0.01 to about 1,500 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day, or any amount or range therein. Preferably, the range is from about 0.01 to about 50.0 mg/kg of body weight per day, or any amount or range therein. More preferably, from about 0.01 to about 20.0 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trails including first-in-human, dose ranging and efficacy trials, in healthy patients and/or those suffering from a given disorder, may be completed according to methods well known in the clinical and medical arts.

EXAMPLES

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

3-(Methylsulfanyl)-1-phenyl-6-piperazin-1-yl-1H-indazole HCl salt

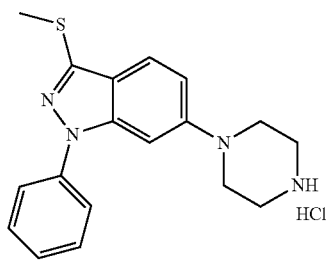 [SMILES: CSc1nn(-c2ccccc2)c2cc(N3CCNCC3)ccc12 ; Cl]

Step A: 2-Amino-4-bromo-benzoic acid N'-phenyl-hydrazide

Into a 500-mL 3-necked round-bottom flask purged and maintained with an inert atmosphere of nitrogen, was placed a solution of 2-amino-4-bromobenzoic acid (10 g, 46.30 mmol, 1.00 equiv) in tetrahydrofuran (300 mL). To the resulting mixture was then added di(1H-imidazol-1-yl)methanone (9 g, 55.56 mmol, 1.20 equiv) dropwise, with stirring at 0-5° C. The resulting mixture was warmed and stirred at 20° C. for 2 hours. To the resulting mixture was then added N-ethyl-N-isopropylpropan-2-amine (7.2 g, 55.81 mmol, 1.20 equiv) dropwise with stirring at room temperature. To the mixture was then added 1-phenylhydrazine (5 g, 46.30 mmol, 1.00 equiv) in several batches at room temperature. The resulting solution was stirred overnight at room temperature. The reaction was then quenched by the addition of 1N hydrogen chloride/$H_2O$. The pH value of the solution was adjusted to about pH1 with 1N HCl. The resulting mixture was then neutralized to pH=7 with 50% NaOH. The resulting solution was extracted with ethyl acetate (2×250 mL) and the organic layers combined. The resulting mixture was washed with water (2×500 mL), sodium bicarbonate (2×500 mL) and saturated brine (2×500 mL). The resulting solution was concentrated under reduced pressure to yield 2-amino-4-bromo-N'-phenylbenzohydrazide as a red solid. MS: 306 ($MH^+$)

Step B: 6-Bromo-1-phenyl-1,2-dihydro-indazol-3-one

Into a 100-mL 3-necked round-bottom flask, was placed a solution of 2-amino-4-bromo-N'-phenylbenzohydrazide (4 g, 13.07 mmol, 1.00 equiv) in 1N HCl:Ethanol=1:1 (40 mL). The resulting solution was heated to 76° C. The solid dissolved to yield red solution. To the resulting mixture was then added a solution of $NaNO_2$ (2.7 g, 39.13 mmol, 3.00 equiv) in water (5 mL) dropwise with stirring at 76° C. The resulting solution was stirred for 1 h at 76° C. in an oil bath. The resulting mixture was cooled to 20° C. with a water bath. The solids were collected by filtration, washed with water (2×40 mL), then dried in an oven under reduced pressure to yield 6-bromo-1-phenyl-1,2-dihydroindazol-3-one as a red solid. MS: 288 ($MH^+$).

Step C: 6-Bromo-1-phenyl-1H-indazole-3-thiol

Into a 100-mL 3-necked round-bottom flask, was placed a solution of 6-bromo-1-phenyl-1,2-dihydroindazol-3-one (7 g, 24.22 mmol, 1.00 equiv) in xylene (50 mL) and $P_2S_5$ (21.5 g, 96.85 mmol, 4.00 equiv). The resulting solution was stirred for 1 h at 130° C. in an oil bath. The solids were collected by filtration, washed with ethyl acetate (2×50 mL). The organic layer was washed with water (2×50 mL). The resulting mixture was dried over anhydrous sodium sulfate and concentrated under vacuum to yield 6-bromo-1-phenyl-1H-indazole-3-thiol as a brown solid. MS: 304 ($MH^+$).

Step D: 6-Bromo-3-methylsulfanyl-1-phenyl-1H-indazole

Into a 500-mL 3-necked round-bottom flask, was placed a solution of 6-bromo-1-phenyl-1H-indazole-3-thiol (24 g, 78.69 mmol, 1.00 equiv) in $CH_3CN$ (200 mL), $Cs_2CO_3$ (28.8 g, 88.34 mmol, 1.12 equiv). To the resulting mixture as then added iodomethane (12.6 g, 88.73 mmol, 1.13 equiv) dropwise with stirring at room temperature. The resulting solution was stirred for 60 min at room temperature. The solids were filtered out. The resulting mixture was concentrated under vacuum. The residue was applied onto a silica gel column with ethyl acetate/petroleum ether (1:100) to yield 6-bromo-3-(methylthio)-1-phenyl-1H-indazole as a yellow solid. MS: 328 (MH+).

Step E: 4-(3-Methylsulfanyl-1-phenyl-1H-indazol-6-yl)-piperazine-1-carboxylic acid tert-butyl ester Into a 50-mL 3-necked round-bottom flask purged and maintained with an inert atmosphere of nitrogen, was placed a solution of 6-bromo-3-(methylthio)-1-phenyl-1H-indazole (300 mg, 0.94 mmol, 1.00 equiv) in toluene (20 mL), tert-butyl piperazine-1-carboxylate (210 mg, 1.13 mmol, 1.20 equiv), $Cs_2CO_3$ (430 mg, 1.32 mmol, 1.40 equiv), Pd(OAc)$_2$ (a catalytic amount), BINAP (a catalytic amount). The resulting mixture was heated to reflux overnight in an oil bath. The solids were filtered out. The filtrate was concentrated under vacuum. The residue was applied onto a silica gel column with ethyl acetate/petroleum ether (1:1) to yield tert-butyl 4-(1-(3-(methylthio)-1-phenyl-1H-indazol-6-yl)piperidin-4-yl)piperazine-1-carboxylate as yellow oil. MS: 425 (MH+).

Step F: 3-Methylsulfanyl-1-phenyl-6-piperazin-1-yl-1H-indazole HCl salt

Into a 50-mL 3-necked round-bottom flask, was placed a solution of tert-butyl 4-(3-(methylthio)-1-phenyl-1H-indazol-6-yl)piperazine-1-carboxylate (100 mg, 0.24 mmol, 1.00 equiv) in dichloromethane (20 mL). Hydrogen chloride (g) was then introduced at 0-5° C. The resulting solution was stirred for 1 h at room temperature. The solids were collected by filtration to yield 3-(methylthio)-1-phenyl-6-(piperazin-1-yl)-1H-indazole hydrochloride as a yellow solid.

MS (m/z): 325 [M−HCl+H]+; $^1$HNMR (400 MHz, MeOD, ppm): δ 7.412-7.395 (2H, d), 7.311-7.232 (4H, m), 6.699-6.677 (1H, d), 6.570 (1H, s), 3.183 (8H, s), 2.382 (3H, s).

Example 2

N-(3-(Methylthio)-1-phenyl-1H-indazol-6-yl)azetidine-3-carboxamide hydrochloride

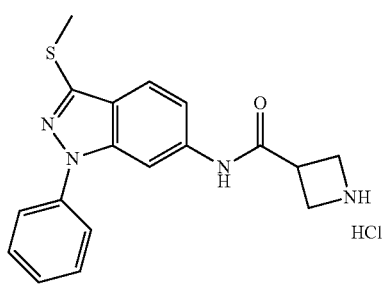 [SMILES: CSc1nn(-c2ccccc2)c2cc(NC(=O)C3CNC3)ccc12 ; Cl]

Step A: 7-Nitro-1H-benzo[d][1,3]oxazine-2,4-dione

Into a 1000-mL 4-necked round-bottom flask purged and maintained with an inert atmosphere of nitrogen, was placed a solution of 2-amino-4-nitrobenzoic acid (54.6 g, 300.00 mmol, 1.00 equiv) in tetrahydrofuran (500 mL), di(1H-imidazol-1-yl)methanone (58.32 g, 360.00 mmol). The resulting solution was stirred for 2 h at 10° C. The solids were collected by filtration to yield 7-nitro-1H-benzo[d][1,3]oxazine-2,4-dione as a yellow solid.

Step B: 2-Amino-4-nitro-benzoic acid N'-phenyl-hydrazide

Into a 1000-mL 3-necked round-bottom flask, was placed a solution of 7-nitro-1H-benzo[d][1,3]oxazine-2,4-dione (56 g, 269.23 mmol, 1.00 equiv) in ethanol (500 mL), 1-phenyl-hydrazine (31.98 g, 296.11 mmol, 1.10 equiv). The resulting solution was heated to reflux for 5 min. The resulting mixture was then concentrated under vacuum. The residue was applied onto a silica gel column with dichloromethane/petroleum ether (1:2~1:0) and ethyl acetate/petroleum ether (1:1) to yield 2-amino-4-nitro-N'-phenylbenzohydrazide as a yellow solid. MS: 273 (MH+).

Step C: 6-Nitro-1-phenyl-1,2-dihydro-indazol-3-one

Into a 1000-mL 4-necked round-bottom flask, was placed a solution of 2-amino-4-nitro-N-phenylbenzohydrazide (23 g, 84.56 mmol, 1.00 equiv) in ethanol (250 mL), 1N hydrogen chloride (250 mL), tetrahydrofuran (100 mL). To the resulting mixture was then added a solution of $NaNO_2$ (17.5 g, 253.62 mmol, 3.00 equiv) in water (45 mL) dropwise with stirring at 72° C. in 40 min. The resulting solution was heated to reflux for 1 hr. The resulting mixture was then cooled to 25° C. The solids were collected by filtration to yield 6-nitro-1-phenyl-1,2-dihydroindazol-3-one as a brown solid. MS: 256 (MH+).

Step D: 6-Nitro-1-phenyl-1,2-dihydro-indazole-3-thione

Into a 250-mL 3-necked round-bottom flask, was placed 6-nitro-1-phenyl-1,2-dihydroindazol-3-one (15 g, 58.82 mmol, 1.00 equiv), xylene (150 mL), $P_2S_5$ (52.2 g, 235.14 mmol). The resulting solution was heated to reflux for 40 min in an oil bath. The resulting mixture was then cooled to 25° C. The resulting solution was diluted with ethyl acetate (50 mL). The solids were filtered out to yield 6-nitro-1-phenyl-1,2-dihydroindazole-3-thione as a yellow solid. MS: 272 (MH+).

Step E: 3-Methylsulfanyl-6-nitro-1-phenyl-1H-indazole

Into a 100-mL 3-necked round-bottom flask, was placed a solution of 6-nitro-1-phenyl-1,2-dihydroindazole-3-thione (3.1 g, 11.44 mmol, 1.00 equiv) in $CH_3CN$ (20 mL), $Cs_2CO_3$ (21 g, 64.42 mmol, 5.63 equiv). To the resulting mixture was then added a solution of iodomethane (11.3 g, 79.58 mmol, 6.96 equiv) in $CH_3CN$ (15 mL) dropwise with stirring at 10° C. in 30 min. The resulting solution was stirred for 30 min at 10° C. The solids were filtered out. The resulting mixture was concentrated under vacuum. The residue was applied onto a silica gel column with ethyl acetate/petroleum ether (1:100) to yield 3-(methylthio)-6-nitro-1-phenyl-1H-indazole as a yellow solid. MS: 285 (MH+).

Step F: 3-Methylsulfanyl-1-phenyl-1H-indazol-6-ylamine

A 100-mL round-bottom flask was purged, flushed and maintained with a hydrogen atmosphere, then, was added a solution of 3-(methylthio)-6-nitro-1-phenyl-1H-indazole (3.5 g, 12.28 mmol, 1.00 equiv) in ethyl acetate (30 mL), Palladium carbon (2.2 g), bubbled with H₂ (gas). The resulting solution was stirred for 48 min at room temperature. The solids were filtered out. The resulting mixture was concentrated under vacuum to yield 3-(methylthio)-1-phenyl-1H-indazol-6-amine as brown oil. MS: 256 (MH⁺)

Step G: 3-(3-Methylsulfanyl-1-phenyl-1H-indazol-6-ylcarbamoyl)-azetidine-1-carboxylic acid tert-butyl ester Into a 50-mL 3-necked round-bottom flask purged and maintained with an inert atmosphere of nitrogen, was placed a solution of 3-(methylthio)-1-phenyl-1H-indazol-6-amine (500 mg, 1.96 mmol, 1.00 equiv) in N,N-dimethylformamide (5 mL), triethylamine (0.5 mL), 1-(tert-butoxycarbonyl)azetidine-3-carboxylic acid (470 mg, 2.34 mmol, 1.19 equiv), HATU (2.235 g, 5.88 mmol, 3.00 equiv). The resulting solution was stirred for 2 h at 15° C. The solids were filtered out. The resulting mixture was concentrated under vacuum. The residue was applied onto a silica gel column with ethyl acetate/petroleum ether (1:5~1:3) to yield tert-butyl 3-((3-(methylthio)-1-phenyl-1H-indazol-6-yl)carbamoyl)azetidine-1-carboxylate as a white solid. MS: 439 (MH⁺).

Step H: N-(3-(methylthio)-1-phenyl-1H-indazol-6-yl)azetidine-3-carboxamide hydrochloride Into a 50-mL 3-necked round-bottom flask, was placed a solution of tert-butyl 3-((3-(methylthio)-1-phenyl-1H-indazol-6-yl)carbamoyl)azetidine-1-carboxylate (105 mg, 0.24 mmol, 1.00 equiv) in dichloromethane (4 mL). The resulting solution was bubbled with HCl (gas) and stirred for 30 min at 0° C. The resulting solids were collected by filtration to yield N-(3-(methylthio)-1-phenyl-1H-indazol-6-yl)azetidine-3-carboxamide hydrochloride as a yellow solid.

MS (m/z): 339 [M−HCl+H]⁺; ¹HNMR (400 MHz, MeOD, ppm): δ 8.453 (1H, s), 7.734-7.714 (2H, d), 7.683-7.661 (1H, d), 7.604-7.565 (2H, t), 7.426-7.407 (1H, t), 7.245-7.224 (1H, d), 4.338-4.238 (4H, m), 3.868-3.827 (1H, m), 2.700 (3H, s).

Example 3

N-(3-(Methylthio)-1-phenyl-1H-indazol-6-yl)-2-(piperidin-2-yl)acetamide hydrochloride

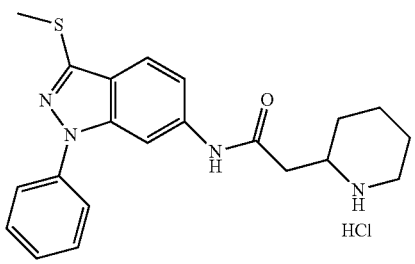 [SMILES: CSc1nn(-c2ccccc2)c2cc(NC(=O)CC3CCCCN3)ccc12 ; Cl]

Step A: 2-[(3-Methylsulfanyl-1-phenyl-1H-indazol-6-ylcarbamoyl)-methyl]-piperidine-1-carboxylic acid tert-butyl ester Into a 50-mL 3-necked round-bottom flask purged and maintained with an inert atmosphere of nitrogen, was placed 2-(1-(tert-butoxycarbonyl)piperidin-2-yl)acetic acid (0.47 mg), 1H-benzo[d][1,2,3]triazol-1-ol (300 mg, 1.96 mmol), EDC.HCl (370 mg, 1.94 mmol), 4-methylmorpholine (590 mg, 5.84 mmol, 2.98 equiv) in dichloromethane (3 mL). The resulting solution was stirred for 10 min at 15° C. A solution of 3-(methylthio)-1-phenyl-1H-indazol-6-amine (500 mg, 1.96 mmol, 1.00 equiv) in dichloromethane (3 mL) was added. The resulting solution was stirred for an additional 2 h at 15° C. The resulting mixture was washed with aq. sodium bicarbonate (1×8 mL) and brine (2×8 mL). The resulting mixture was dried over anhydrous sodium sulfate and concentrated under vacuum. The residue was applied onto a silica gel column with ethyl acetate/petroleum ether (1:10~1:3) to yield tert-butyl 2-(2-(3-(methylthio)-1-phenyl-1H-indazol-6-ylamino)-2-oxoethyl)piperidine-1-carboxylate as a white solid. MS: 481 (MH⁺).

Step B: N-(3-(methylthio)-1-phenyl-1H-indazol-6-yl)-2-(piperidin-2-yl)acetamide hydrochloride Into a 50-mL 3-necked round-bottom flask, was placed a solution of tert-butyl 2-(2-(3-(methylthio)-1-phenyl-1H-indazol-6-ylamino)-2-oxoethyl)piperidine-1-carboxylate (105 mg, 0.22 mmol, 1.00 equiv) in dichloromethane (5 mL). To the above mixture was introduce H₂ (g). The resulting solution was stirred for 30 min at 0° C. The solids were collected by filtration to yield N-(3-(methylthio)-1-phenyl-1H-indazol-6-yl)-2-(piperidin-2-yl)acetamide hydrochloride as a gray solid.

MS (m/z): 381 [M−HCl+H]⁺; ¹HNMR (300 MHz, D₂O, ppm): δ 7.690-7.229 (7H, m), 6.692 (1H, s), 3.395-3.351 (2H, d), 3.007-2.929 (1H, t), 2.661 (2H, s), 2.505-2.419 (3H, m), 1.816 (3H, s), 1.575 (3H, d).

Example 4

1-(3-(Methylthio)-1-phenyl-1H-indazol-6-yl)-3-(pyrrolidin-3-yl)urea hydrochloride

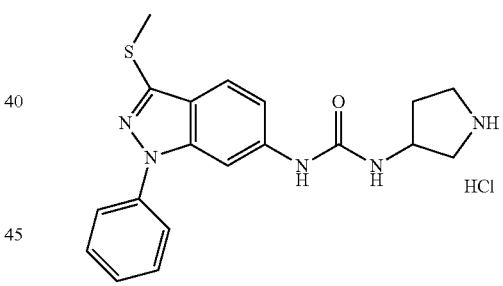

Step A: 3-[3-(3-Methylsulfanyl-1-phenyl-1H-indazol-6-yl)-ureido]-pyrrolidine-1-carboxylic acid tert-butyl ester Into a 50-mL 3-necked round-bottom flask, was placed a solution of bis(trichloromethyl)carbonate (200 mg, 0.67 mmol) in dichloromethane (3 mL). To the resulting mixture was then added a mixture of 3-(methylthio)-1-phenyl-1H-indazol-6-amine (500 mg, 1.96 mmol, 1.00 equiv) and DIEA (560 mg, 4.33 mmol, 2.21 equiv) in dichloromethane (2 mL) dropwise with stirring at 0° C. in 30 min. The resulting solution was stirred for 3 h at 15° C. The resulting mixture was added to a solution of tert-butyl 3-aminopyrrolidine-1-carboxylate (440 mg, 2.37 mmol, 1.21 equiv) in dichloromethane (3 mL) dropwise with stirring at 15° C. in 15 min. The resulting solution stirred for an additional 4 h at 15° C. The resulting mixture was concentrated under vacuum. The residue was applied onto a silica gel column with ethyl acetate:petroleum ether (1:4~1:3) to yield tert-butyl 3-(3-(3-

(methylthio)-1-phenyl-1H-indazol-6-yl)ureido)pyrrolidine-1-carboxylate as a white solid. MS: 468 (MH⁺).

Step B: 1-(3-Methylsulfanyl-1-phenyl-1H-indazol-6-yl)-3-pyrrolidin-3-yl-urea hydrochloride Into a 50-mL 3-necked round-bottom flask, was placed a solution of tert-butyl 3-(3-(3-(methylthio)-1-phenyl-1H-indazol-6-yl)ureido)pyrrolidine-1-carboxylate (120 mg, 0.26 mmol, 1.00 equiv) in dichloromethane (4 mL). The solution was bubbled with HCl (g) at 0° C. in 30 min. The resulting solution was stirred for 30 min at 0° C. The solids were collected by filtration. The solid was washed with ethyl acetate/methanol (2×3.8 mL) to yield 1-(3-(methylthio)-1-phenyl-1H-indazol-6-yl)-3-(pyrrolidin-3-yl)urea hydrochloride as a white solid.

MS (m/z): 368 [M−HCl+H]⁺; ¹HNMR (400 MHz, DMSO, ppm): δ 9.332 (1H, S), 9.174-9.074 (2H, d), 8.220 (1H, s), 7.690-7.670 (2H, d), 7.614-7.574 (3H, t), 7.404-7.368 (1H, t), 7.059-7.006 (2H, m), 4.293-4.248 (1H, m), 3.569-3.169 (4H, m), 3.059-3.032 (1H, t), 2.658 (3H, s), 2.212-2.126 (1H, m), 1.874-1.793 (1H, m).

Example 5

N-(3-(Methylthio)-1-phenyl-1H-indazol-6-yl)pyrrolidine-3-carboxamide hydrochloride

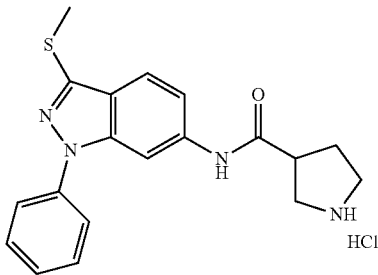 [SMILES: CSc1nn(-c2ccccc2)c2cc(NC(=O)C3CCNC3)ccc12 ; Cl]

The title compound was prepared according to the procedure as described in Example 2 reacting pyrrolidine-1,3-dicarboxylic acid 1-tert-butyl ester.

MS (m/z): 353 [M−HCl+H]⁺; ¹HNMR (400 MHz, MeOD, ppm): δ 8.447-8.407 (2H, d), 7.708-7.632 (3H, m), 7.576-7.537 (2H, t), 7.401-7.365 (1H, t), 7.245-7.224 (1H, d), 3.653-3.624 (1H, t), 3.512-3.403 (4H, m), 3.686 (3H, s), 2.449-2.397 (1H, m), 2.291-2.260 (1H, t).

Example 6

N-(3-(Methylthio)-1-phenyl-1H-indazol-6-yl)piperidine-4-carboxamide hydrochloride

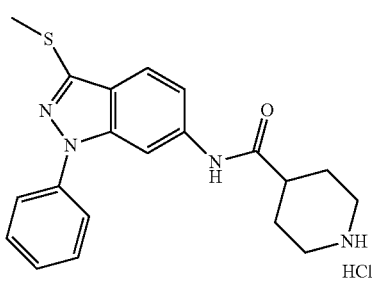 [SMILES: CSc1nn(-c2ccccc2)c2cc(NC(=O)C3CCNCC3)ccc12 ; Cl]

The title compound was prepared according to the procedure as described in Example 2 reacting piperidine-1,4-dicarboxylic acid 1-tert-butyl ester.

MS (m/z): 367 [M−HCl+H]⁺; ¹HNMR (400 MHz, MeOD, ppm): δ 10.082 (1H, s), 8.303 (1H, s), 7.628-7.609 (2H, d), 7.568-7.546 (1H, d), 7.498-7.461 (2H, t), 7.316-7.279 (1H, t), 7.151-7.130 (1H, d), 3.421-3.390 (2H, d), 3.044-3.983 (2H, t), 2.703-2.648 (1H, d), 2.597 (3H, s), 2.054-2.020 (2H, d), 1.947-1.857 (2H, m).

Example 7

1-(3-(Methylthio)-1-phenyl-1H-indazol-6-yl)-3-(piperidin-4-yl)urea hydrochloride

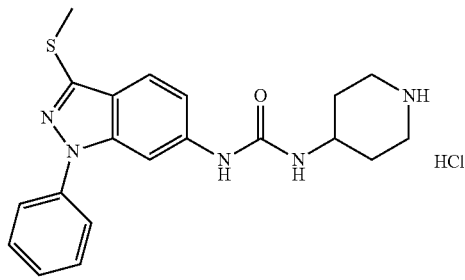 [SMILES: CSc1nn(-c2ccccc2)c2cc(NC(=O)NC3CCNCC3)ccc12 ; Cl]

The title compound s prepared according to the procedure as described in Example 4 using 4-isocyanato-piperidine-1-carboxylic acid tert-butyl ester.

MS (m/z): 382 [M−HCl+H]⁺; ¹HNMR (400 MHz, MeOD, ppm): δ 8.156 (1H, s), 7.707-7.687 (2H, d), 7.579-7.528 (3H, m), 7.382-7.345 (1H, t), 7.024-6.999 (1H, m), 3.895-3.844 (1H, m), 3.445-3.412 (2H, d), 3.357-3.318 (2H, d), 3.157-3.102 (2H, t), 2.184-2.149 (2H, t), 1.803-1.705 (2H, m).

Example 8

N-(3-Methylsulfanyl-1-phenyl-1H-indazol-6-yl)-isonicotinamide

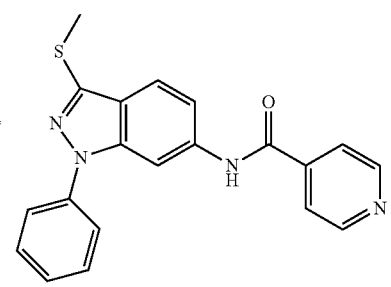

The title compound s prepared according to the procedure as described in Example 2 reacting isonicotinic acid.

MS (m/z): 361 [M+H]⁺; ¹HNMR (400 MHz, DMSO, ppm): δ 10.770 (1H, s), 8.815-8.806 (2H, d), 8.514 (1H, s), 7.894-7.886 (2H, d), 7.735 (3H, s), 7.645-7.607 (3H, t), 7.439-7.404 (1H, t), 2.698 (3H, s).

Example 9

N-(3-(Methylthio)-1-phenyl-1H-indazol-6-yl)-2-(pyridin-4-yl)acetamide

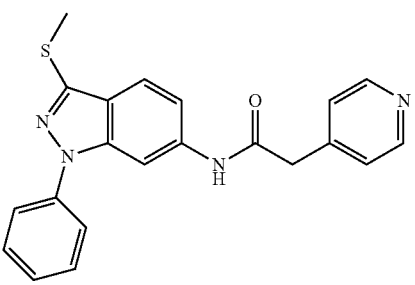 [SMILES: CSc1nn(-c2ccccc2)c2cc(NC(=O)Cc3ccncc3)ccc12]

The title compound s prepared according to the procedure as described in Example 2 reacting pyridin-4-yl-acetic acid.

MS (m/z): 375 [M+H]$^+$; $^1$HNMR (400 MHz, MeOD, ppm): δ 8.770-8.755 (2H, d), 8.384 (1H, s), 8.009-7.994 (2H, d), 7.702-7.659 (3H, t), 7.572-7.532 (2H, t), 7.396-7.359 (1H, t), 7.250-7.225 (1H, m), 4.114-4.095 (1H, d), 3.322-3.314 (2H, t), 2.693 (3H, s).

Example 10

2-(3-(methylthio)-1-phenyl-1H-indazol-6-yl)-2,5-diaza-bicyclo[2.2.1]heptane hydrochloride

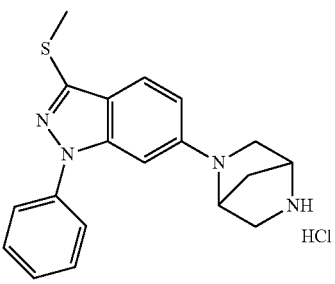 [SMILES: CSc1nn(-c2ccccc2)c2cc(N3CC4CC3CN4)ccc12 ; Cl]

The title compound was prepared according to the procedure as described in Example 1 reacting 2,5-diaza-bicyclo[2.2.1]heptane-2-carboxylic acid tert-butyl ester MS (m/z): 337 [M−HCl+H]$^+$; $^1$HNMR (400 MHz, D$_2$O, ppm): δ 7.462-7.423 (2H, t), 7.383-7.293 (4H, m), 6.507-6.485 (1H, d), 6.285 (1H, s), 4.454 (1H, s), 4.393 (1H, s), 3.549-3.526 (1H, d), 3.215-3.155 (3H, t), 2.431 (3H, s), 2.115-2.087 (1H, d), 1.938-1.908 (1H, d).

Example 11

6-(1,4-Diazepan-1-yl)-3-(methylthio)-1-phenyl-1H-indazole hydrochloride

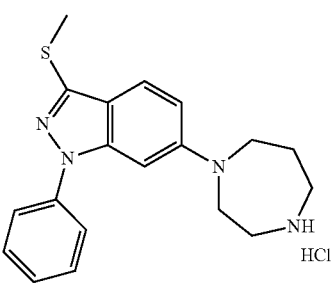 [SMILES: CSc1nn(-c2ccccc2)c2cc(N3CCCNCC3)ccc12 ; Cl]

The title compound was prepared according to the procedure as described in Example 1 reacting [1,4]diazepane-1-carboxylic acid tert-butyl ester.

MS (m/z): 339 [M−HCl+H]$^+$; $^1$HNMR (400 MHz, MeOD, ppm): δ 7.704-7.685 (2H, d), 7.597-7.544 (3H, m), 7.392-7.355 (1H, t), 6.949-6.921 (1H, t), 6.872-6.868 (1H, d), 3.889-3.863 (2H, t), 3.691-3.661 (2H, t), 3.457-3.430 (2H, t), 2.661 (3H, s), 2.244-2.215 (2H, t).

Example 12

N-(3-(Methylthio)-1-phenyl-1H-indazol-6-yl)piperidine-3-carboxamide hydrochloride

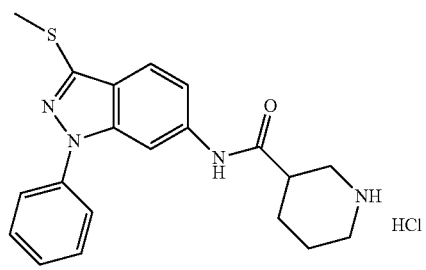 [SMILES: CSc1nn(-c2ccccc2)c2cc(NC(=O)C3CCCNC3)ccc12 ; Cl]

The title compound was prepared according to the procedure as described in Example 2 reacting piperidine-1,3-dicarboxylic acid 1-tert-butyl ester.

MS (m/z): 367 [M−HCl+H]$^+$; $^1$HNMR (400 MHz, D$_2$O, ppm): δ 7.566 (1H, s), 7.484-7.445 (2H, t), 7.368-7.349 (1H, d), 7.273-7.218 (3H, m), 3.349-3.296 (2H, m), 3.132-2.987 (2H, m), 2.821-2.772 (1H, m), 2.017-1.912 (2H, m), 1.771-1.684 (2H, m).

Example 13

N-(3-(Methylthio)-1-phenyl-1H-indazol-6-yl)pyrrolidine-2-carboxamide hydrochloride

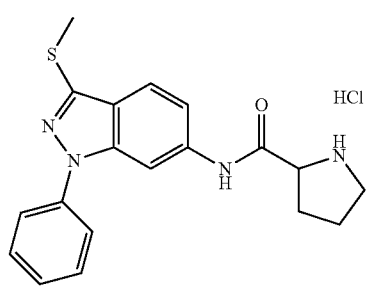 [SMILES: CSc1nn(-c2ccccc2)c2cc(NC(=O)C3CCCN3)ccc12 ; Cl]

The title compound was prepared according to the procedure as described in Example 2 using pyrrolidine-1,2-dicarboxylic acid 1-tert-butyl ester MS (m/z): 353 [M−HCl+H]$^+$; $^1$HNMR (400 MHz, D$_2$O, ppm): δ 7.681 (1H, s), 7.534-7.495 (2H, t), 7.446-7.375 (4H, m), 6.926-6.904 (1H, d), 4.446-4.410 (1H, m), 3.467-3.391 (2H, m), 2.508-2.448 (4H, m), 2.078-2.033 (3H, m).

Example 14

N-(3-(Methylthio)-1-phenyl-1H-indazol-6-yl)nicotinamide

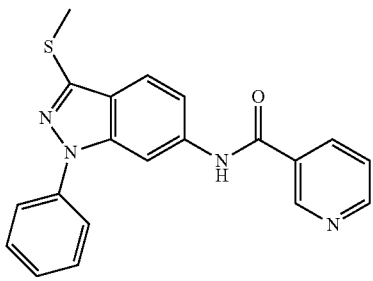 [SMILES: CSc1nn(-c2ccccc2)c2cc(NC(=O)c3cccnc3)ccc12]

The title compound was prepared according to the procedure as described in Example 2 reacting nicotinic acid.

MS (m/z): 361 [M+H]$^+$; $^1$HNMR (400 MHz, DMSO, ppm): δ 10.709 (1H, s), 9.141 (1H, s), 8.791-8.782 (1H, d), 8.520 (1H, s), 8.337-8.317 (1H, d), 7.761-7.739 (3H, d), 7.649-7.580 (4H, m), 7.444-7.426 (1H, d), 2.703 (3H, s).

Example 15

3-(Methylthio)-1-phenyl-6-(3-(piperazin-1-yl)azetidin-1-yl)-1H-indazole hydrochloride

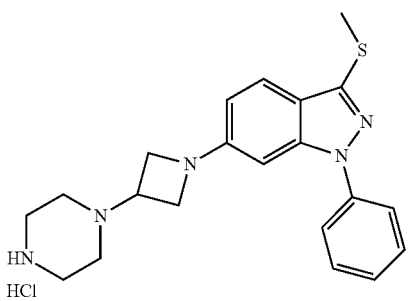 [SMILES: CSc1nn(-c2ccccc2)c2cc(N3CC(N4CCNCC4)C3)ccc12 ; Cl]

Step A: 4-[1-(3-Methylsulfanyl-1-phenyl-1H-indazol-6-yl)-azetidin-3-yl]-piperazine-1-carboxylic acid tert-butyl ester Into a 50-mL 3-necked round-bottom flask purged and maintained with an inert atmosphere of nitrogen, was placed a solution of 6-bromo-3-(methylthio)-1-phenyl-1H-indazole (300 mg, 0.94 mmol, 1.00 equiv) in toluene (20 mL), tert-butyl 4-(azetidin-3-yl)piperazine-1-carboxylate (270 mg, 1.12 mmol, 1.20 equiv), Cs$_2$CO$_3$ (430 mg, 1.32 mmol, 1.40 equiv), Pd(OAc)$_2$ (a catalytic amount), BINAP (a catalytic amount). The resulting solution was heated to reflux overnight in an oil bath. The solids were filtered out. The filtrate was concentrated under vacuum. The residue was applied onto a silica gel column with ethyl acetate/petroleum ether (1:1) to yield tert-butyl 4-(1-(3-(methylthio)-1-phenyl-1H-indazol-6-yl)azetidin-3-yl)piperazine-1-carboxylate as a yellow solid. MS: 480 (MH$^+$).

Step B: 3-(methylthio)-1-phenyl-6-(3-(piperazin-1-yl)azetidin-1-yl)-1H-indazole hydrochloride Into a 50-mL 3-necked round-bottom flask, was placed a solution of tert-butyl 4-(1-(3-(methylthio)-1-phenyl-1H-indazol-6-yl)azetidin-3-yl)piperazine-1-carboxylate (100 mg, 0.21 mmol, 1.00 equiv) in dichloromethane (20 mL). To the resulting mixture, HCl (g) was introduced at 0-5° C. The resulting solution was stirred for 1 h at room temperature. The solids were collected by filtration to yield 3-(methylthio)-1-phenyl-6-(3-(piperazin-1-yl)azetidin-1-yl)-1H-indazole hydrochloride as a white solid.

MS (m/z): 380 [M−HCl+H]$^+$; $^1$HNMR (400 MHz, D$_2$O, ppm): δ 7.491-7.367 (6H, m), 6.345-6.283 (2H, m), 3.793 (2H, d), 3.550 (2H, s), 3.317 (1H, s), 3.206 (4H, s), 2.622 (4H, s), 2.505 (3H, s).

Example 16

4-(3-Methylsulfanyl-1-phenyl-1H-indazol-6-yl)-piperazin-1-yl]-piperidin-3-yl-methanone hydrochloride

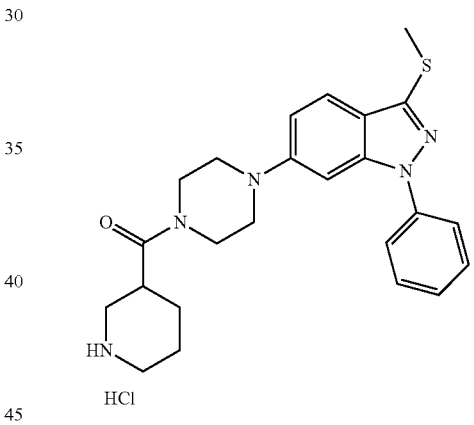

Step A: 3-[4-(3-Methylsulfanyl-1-phenyl-1H-indazol-6-yl)-piperazine-1-carbonyl]-piperidine-1-carboxylic acid tert-butyl ester Into a 50-mL 3-necked round-bottom flask purged and maintained with an inert atmosphere of nitrogen, was placed a solution of 3-(methylthio)-1-phenyl-6-(piperazin-1-yl)-1H-indazole hydrochloride (from Example 1, 80 mg, 0.22 mmol, 1.00 equiv) in N,N-dimethylformamide (10 mL), triethylamine (50 mg, 0.50 mmol, 2.10 equiv), 1-(tert-butoxycarbonyl)piperidine-3-carboxylic acid (60 mg, 0.26 mmol, 1.20 equiv), HATU (250 mg, 0.66 mmol, 3.00 equiv). The resulting solution was stirred overnight at room temperature. The resulting mixture was concentrated under vacuum. The residue was applied onto a silica gel column with ethyl acetate/petroleum ether (1:1) to yield tert-butyl 3-(1-(3-(methylthio)-1-phenyl-1H-indazol-6-yl)piperazine-4-carbonyl)piperidine-1-carboxylate as yellow oil. MS: 536 (MH$^+$)

Step B: 4-(3-Methylsulfanyl-1-phenyl-1H-indazol-6-yl)-piperazin-1-yl]-piperidin-3-yl-methanone hydrochloride Into a 50-mL 3-necked round-bottom flask, was placed a solution of tert-butyl 3-(1-(3-(methylthio)-1-phenyl-1H-indazol-6-yl)piperazine-4-carbonyl)piperidine-1-carboxylate (80 mg, 0.15 mmol, 1.00 equiv) in dichloromethane (10 mL). To the resulting mixture, HCl (g) was introduced at 0-5° C. The resulting solution was stirred for 1 h at room temperature. The solids were collected by filtration, then washed with diethyl ether (3×10 mL) to yield (4-(3-(methylthio)-1-phenyl-1H-indazol-6-yl)piperazin-1-yl)(piperidin-3-yl)methanone hydrochloride as a yellow solid.

MS (m/z): 436 [M−HCl+H]$^+$; $^1$HNMR (400 MHz, D$_2$O, ppm): δ 7.48 (2H, m), 7.37 (4H, m), 6.81-6.74 (1H, m) 3.58-3.47 (4H, m), 3.21-2.91 (9H, m), 2.48 (3H, s), 1.88 (1H, m), 1.77 (2H, m), 1.60 (1H, m).

Example 17

(4-(3-(Methylthio)-1-phenyl-1H-indazol-6-yl)piperazin-1-yl)(pyridin-4-yl)methanone

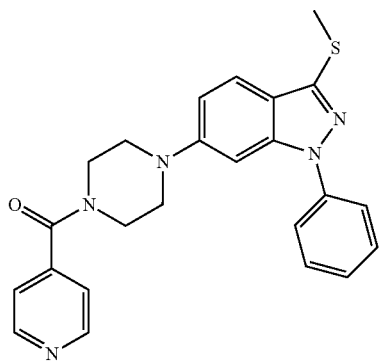 [SMILES: CSc1nn(-c2ccccc2)c2cc(N3CCN(C(=O)c4ccncc4)CC3)ccc12]

Into a 50-mL 3-necked round-bottom flask purged and maintained with an inert atmosphere of nitrogen, was placed a solution of 3-(methylthio)-1-phenyl-6-(piperazin-1-yl)-1H-indazole hydrochloride (200 mg, 0.55 mmol, 1.00 equiv) in N,N-dimethylformamide (5 mL), triethylamine (140.3 mg, 1.39 mmol, 2.51 equiv), isonicotinic acid (82 mg, 0.67 mmol, 1.20 equiv), and the resulting solution was stirred for 10 min at room temperature. HATU (631 mg, 1.66 mmol, 3.00 equiv) was added and resulting solution was stirred for an additional 2 h at room temperature. The resulting solution was diluted with ethyl acetate (20 mL). The resulting mixture was washed with brine (2×15 mL). The resulting mixture was dried over anhydrous sodium sulfate and concentrated under vacuum. The residue was applied onto a silica gel column with ethyl acetate:petroleum ether:THF (1:1:1) to yield (4-(3-(methylthio)-1-phenyl-1H-indazol-6-yl)piperazin-1-yl)(pyridin-4-yl)methanone as a light yellow solid.

MS (m/z): 430 [M+H]$^+$; $^1$HNMR (400 MHz, CDCl$_3$, ppm): δ 8.75 (2H, m), 7.69-7.51 (5H, m), 7.37-7.28 (3H, m), 7.03 (1H, s), 6.96 (1H, m), 3.99 (2H, m), 3.35 (2H, m), 3.20 (2H, m), 2.70 (3H, s).

Example 18

3-Methylsulfanyl-1-phenyl-6-(4-pyridin-4-ylmethyl-piperazin-1-yl)-1H-indazole Hydrochloride

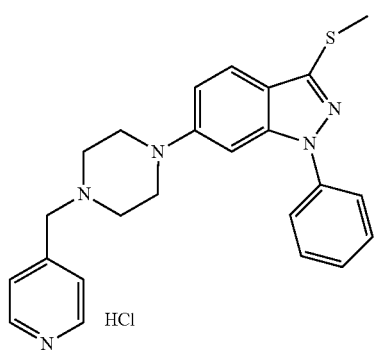 [SMILES: CSc1nn(-c2ccccc2)c2cc(N3CCN(Cc4ccncc4)CC3)ccc12 ; Cl]

Into a 50-mL 3-necked round-bottom flask purged and maintained with an inert atmosphere of nitrogen, was placed a solution of (4-(3-(methylthio)-1-phenyl-1H-indazol-6-yl)piperazin-1-yl)(pyridin-4-yl)methanone (130 mg, 0.30 mmol, 1.00 equiv) in tetrahydrofuran (8 mL). To the resulting mixture was then added Borane-THF (2.4 mL, 1M) dropwise with stirring at 0° C. in 15 min. The resulting solution was heated to reflux overnight. The resulting mixture was then concentrated under vacuum. To the residue was added HCl (5 mL, 12M). The resulting solution was stirred for an additional 15 min while the temperature was maintained at reflux. The resulting mixture was concentrated under vacuum. The residue (50 mg) was purified by Prep-HPLC with the following conditions (Waters-2): Column, Sunfire C18, 19*150 mm; mobile phase, water in 0.05% TFA and ACN (20% ACN up to 42% in 6.5 min, down to 20% in 9 min); Detector, UV254 to yield 3-(methylthio)-1-phenyl-6-(4-(pyridin-4-ylmethyl)piperazin-1-yl)-1H-indazole hydrochloride as a yellow solid.

MS (m/z): 416 [M−HCl+H]$^+$; $^1$HNMR (400 MHz, D$_2$O, ppm): δ 8.76 (2H, m), 7.75 (2H, m), 7.63-7.55 (5H, m), 7.39 (1H, m), 7.08 (2H, m), 4.4 (2H, m), 3.30 (8H, m), 2.65 (3H, s).

Example 19

3-(Methylthio)-1-phenyl-6-(3-(piperazin-1-yl)pyrrolidin-1-yl)-1H-indazole hydrochloride

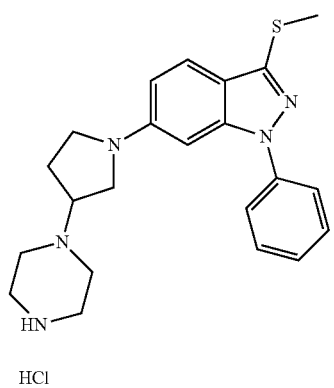 [SMILES: CSc1nn(-c2ccccc2)c2cc(N3CCC(N4CCNCC4)C3)ccc12 ; Cl]

The title compound was prepared according to the procedure as described in Example 15 reacting 4-pyrrolidin-3-yl-piperazine-1-carboxylic acid tert-butyl ester.

MS (m/z): 394 [M−HCl+H]$^+$; $^1$HNMR (400 MHz, D$_2$O, ppm): δ 7.532 (5H, m), 7.39 (1H, m), 6.66 (1H, m), 6.43 (1H, s), 3.550 (2H, s), 3.317 (1H, s), 3.206 (4H, s), 2.622 (4H, s), 2.505 (3H, s).

Example 20

3-(Methylthio)-1-phenyl-6-(4-(piperazin-1-yl)piperidin-1-yl)-1H-indazole hydrochloride

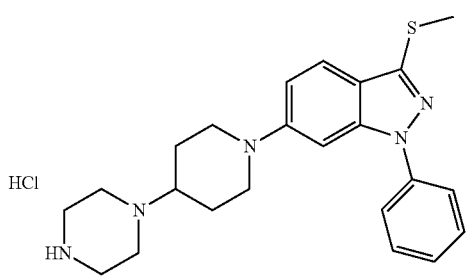 [SMILES: Cl ; CSc1nn(-c2ccccc2)c2cc(N3CCC(N4CCNCC4)CC3)ccc12]

The title compound was prepared according to the procedure as described in Example 15 reacting 4-piperidin-4-yl-piperazine-1-carboxylic acid tert-butyl ester.

MS (m/z): 408 [M−HCl+H]⁺; ¹HNMR (400 MHz, D$_2$O, ppm): δ 7.68 (1H, m), 7.51 (4H, m), 7.40 (1H, m), 7.10 (2H, m), 3.82 (2H, m), 3.45 (9H, m), 3.00 (2H, m), 2.52 (3H, s), 2.25 (2H, m), 1.85 (2H, m).

Example 21

6-(4-(Azetidin-3-yl)piperazin-1-yl)-3-(methylthio)-1-phenyl-1H-indazole hydrochloride

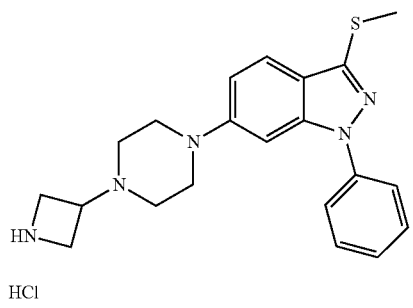 [SMILES: CSc1nn(-c2ccccc2)c2cc(N3CCN(C4CNC4)CC3)ccc12 ; Cl]

The title compound was prepared according to the procedure as described in Example 15 reacting 3-piperazin-1-yl-azetidine-1-carboxylic acid tert-butyl ester.

MS (m/z): 380 [M−HCl+H]⁺; ¹HNMR (400 MHz, D$_2$O, ppm): δ 7.56-7.38 (6H, m), 6.96-6.89 (2H, m), 4.36 (4H, m), 4.26 (1H, m), 3.40 (4H, m), 2.49 (3H, s).

Example 22

3-(Methylthio)-1-phenyl-6-(4-(pyrrolidin-3-yl)piperazin-1-yl)-1H-indazole hydrochloride

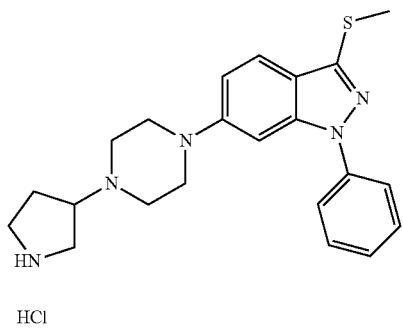 [SMILES: CSc1nn(-c2ccccc2)c2cc(N3CCN(C4CCNC4)CC3)ccc12 ; Cl]

The title compound was prepared according to the procedure as described in Example 15 reacting 3-pyrazin-1-yl-pyrrolidine-1-carboxylic acid tert-butyl ester.

MS (m/z): 394 [M−HCl+H]⁺; ¹HNMR (400 MHz, D$_2$O, ppm): δ 7.48-7.34 (6H, m), 6.85 (2H, m), 6.75 (1H, m), 3.83 (1H, m), 3.55-3.31 (12H, m), 2.59 (1H, m), 2.44 (3H, m), 2.22-2.13 (1H, m).

Example 23

3-(Methylthio)-1-phenyl-6-(4-(piperidin-4-yl)piperazin-1-yl)-1H-indazole hydrochloride

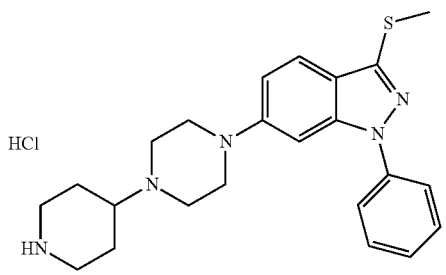 [SMILES: Cl ; CSc1nn(-c2ccccc2)c2cc(N3CCN(C4CCNCC4)CC3)ccc12]

The title compound was prepared according to the procedure as described in Example 15 reacting 4-piperazin-1-yl-piperidine-1-carboxylic acid tert-butyl ester.

MS (m/z): 408 [M−HCl+H]⁺; ¹HNMR (400 MHz, D$_2$O, ppm): δ 7.7 (2H, m), 7.48-7.33 (4H, m), 6.7 (1H, d), 6.64 (1H, s), 3.56 (7H, m), 3.26 (6H, m), 2.42 (3H, s), 1.81 (2H, m), 1.91-1.85 (2H, m).

Example 24

3-(Methylthio)-1-phenyl-6-(4-(pyridin-2-yl)piperazin-1-yl)-1H-indazole

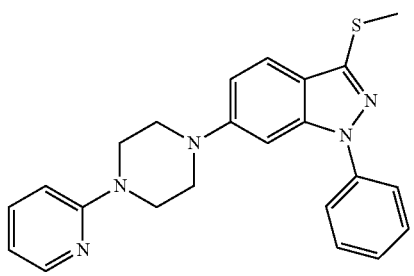 [SMILES: CSc1nn(-c2ccccc2)c2cc(N3CCN(c4ccccn4)CC3)ccc12]

The title compound was prepared according to the procedure as described in Example 15 reacting 1-pyridin-2-yl-piperazine.

MS (m/z): 402 [M+H]⁺; ¹HNMR (400 MHz, CDCl$_3$, ppm): δ 8.23 (1H, s), 7.70 (2H, m), 7.61 (1H, s), 7.53 (3H, m), 7.35 (1H, m), 7.047 (1H, s), 6.99 (1H, m), 6.69 (2H, m), 3.75 (3H, m), 3.38 (3H, m), 2.69 (3H, m).

Example 25

1-(3-(Methylthio)-1-phenyl-1H-indazol-6-yl)-3-(pyrrolidin-3-yl)imidazolidin-2-one hydrochloride

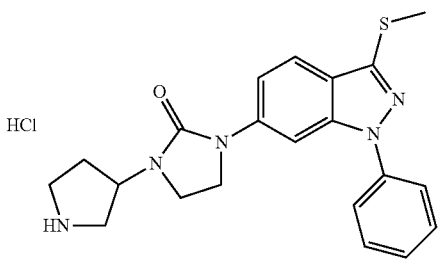 [SMILES: Cl ; CSc1nn(-c2ccccc2)c2cc(N3CCN(C4CCNC4)C3=O)ccc12]

The title compound was prepared according to the procedure as described in Example 15 reacting 3-(2-oxo-imidazolidin-1-yl)-pyrrolidine-1-carboxylic acid tert-butyl ester; followed by de-protection of N-Boc group by reacting with HCl.
MS (m/z): 394 [M−HCl+H]$^+$; $^1$HNMR (400 MHz, D$_2$O, ppm): δ 7.40-7.36 (2H, m), 7.28 (1H, m), 7.16 (2H, m), 6.95 (1H, m), 6.86 (1H, m), 6.65 (1H, m), 4.36 (1H, m), 3.47-3.10 (7H, m), 2.40 (3H, s), 2.19 (1H, m), 1.98 (1H, m).

Example 26

1-(3-(Methylthio)-1-phenyl-1H-indazol-6-yl)-3-(piperidin-4-yl)imidazolidin-2-one hydrochloride

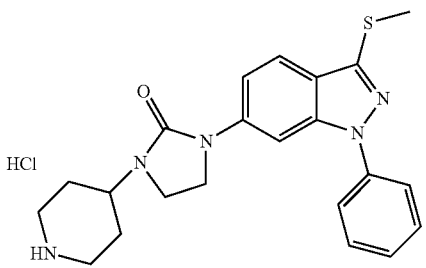 [SMILES: Cl ; CSc1nn(-c2ccccc2)c2cc(N3CCN(C4CCNCC4)C3=O)ccc12]

The title compound was prepared according to the procedure as described in Example 15 reacting 4-(2-oxo-imidazolidin-1-yl)-piperidine-1-carboxylic acid tert-butyl ester, followed by de-protection of N-Boc group by reacting with HCl.
MS (m/z): 408 [M−HCl+H]$^+$; $^1$HNMR (400 MHz, D$_2$O, ppm): δ 7.45 (2H, m), 7.32-7.18 (4H, m), 6.87 (1H, m), 3.82 (1H, m), 3.47-3.25 (6H, m), 3.07-3.00 (2H, m), 2.45 (3H, s), 1.81 (4H, m).

Example 27

1-(3-(Methylthio)-1-phenyl-1H-indazol-6-yl)-3-(pyrrolidin-3-ylmethyl)imidazolidin-2-one hydrochloride

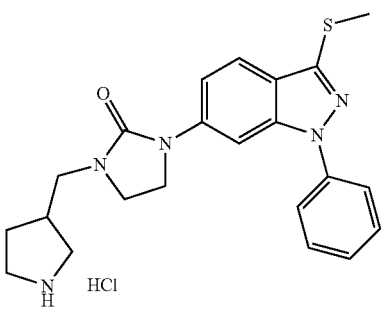 [SMILES: CSc1nn(-c2ccccc2)c2cc(N3CCN(CC4CCNC4)C3=O)ccc12 ; Cl]

The title compound was prepared according to the procedure as described in Example 15 reacting 3-(2-oxo-imidazolidin-1-ylmethyl)-pyrrolidine-1-carboxylic acid tert-butyl ester, by de-protection of N-Boc group by reacting with HCl.
MS (m/z): 408 [M−HCl+H]$^+$; $^1$HNMR (400 MHz, D$_2$O, ppm): δ 7.43-7.39 (2H, m), 7.30-7.16 (4H, m), 7.04 (1H, s), 6.87 (1H, m), 3.36-3.13 (9H, m), 2.89 (1H, m), 2.60 (1H, m), 2.43 (3H, s), 2.08 (1H, m), 1.65 (1H, m).

Example 28

1-(3-(Methylthio)-1-phenyl-1H-indazol-6-yl)-3-(piperidin-3-ylmethyl)imidazolidin-2-one hydrochloride

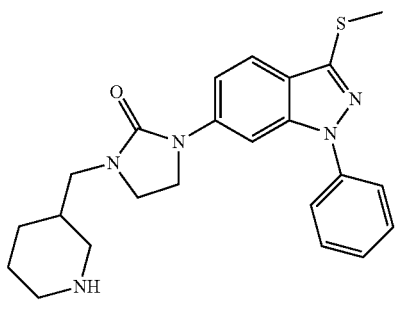

The title compound was prepared according to the procedure as described in Example 15 reacting 4-(2-oxo-imidazolidin-1-ylmethyl)-piperidine-1-carboxylic acid tert-butyl ester, followed by de-protection of N-Boc group by reacting with HCl.
MS (m/z): 422 [M−HCl+H]$^+$; $^1$HNMR (400 MHz, D$_2$O, ppm): δ 7.37-6.95 (8H, m), 6.75 (1H, m), 3.25 (6H, m),
3.18 (2H, m), 2.96 (1H, m), 2.78 (1H, m), 2.57 (1H, m), 2.39 (3H, s), 1.94-1.53 (4H, m), 1.13 (1H, m).

Example 29

3-(Methylthio)-1-phenyl-6-(4-(pyridin-4-yl)piperazin-1-yl)-1H-indazole

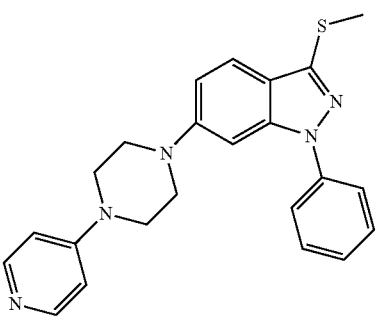 [SMILES: CSc1nn(-c2ccccc2)c2cc(N3CCN(c4ccncc4)CC3)ccc12]

The title compound was prepared according to the procedure as described in Example 15 reacting 1-pyridin-4-yl-piperazine.
MS (m/z): 402 [M+H]$^+$; $^1$HNMR (400 MHz, CDCl$_3$, ppm): δ 8.31 (2H, m), 7.79 (2H, m), 7.71 (1H, m), 7.64 (2H, m), 7.52 (1H, m), 7.04-6.96 (2H, m), 6.74 (2H, m), 3.66 (4H, m), 3.41 (4H, m), 2.08 (3H, s).

Example 30

4-(3-(Methylthio)-1-phenyl-1H-indazol-6-yl)piperazin-1-yl)(pyridin-2-yl)methanone

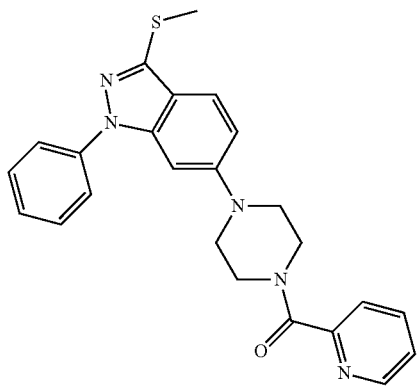 [SMILES: CSc1nn(-c2ccccc2)c2cc(N3CCN(C(=O)c4ccccn4)CC3)ccc12]

The title compound was prepared according to the procedure as described in Example 17 reacting pyridine-2-carboxylic acid.

MS (m/z): 430 [M+H]$^+$; $^1$HNMR (400 MHz, CDCl$_3$, ppm): δ 8.63 (1H, m), 7.87-7.54 (7H, m), 7.41-7.33 (2H, m), 7.07 (1H, m), 6.98 (1H, m), 4.04 (2H, m), 3.88 (2H, m), 3.41 (2H, m), 3.30 (2H, m), 2.71 (3H, s).

Example 31

(4-(3-(Methylthio)-1-phenyl-1H-indazol-6-yl)piperazin-1-yl)(pyridin-3-yl)methanone

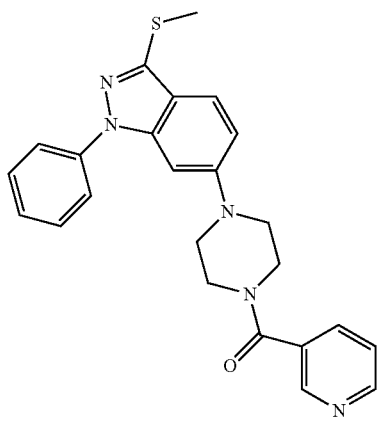 [SMILES: CSc1nn(-c2ccccc2)c2cc(N3CCN(C(=O)c4cccnc4)CC3)ccc12]

The title compound was prepared according to the procedure as described in Example 17 reacting nicontic acid.

MS (m/z): 430 [M+H]$^+$; $^1$HNMR (400 MHz, CDCl$_3$, ppm): δ 8.74 (2H, m), 7.85-7.52 (6H, m), 7.43 (1H, m), 7.33 (1H, m), 6.98 (1H, s), 6.95 (1H, m), 4.00 (2H, m), 3.67 (2H, m), 3.34 (4H, m), 2.72 (3H, s).

Example 32

3-(Methylthio)-1-phenyl-6-(4-(pyridin-3-ylmethyl) piperazin-1-yl)-1H-indazole hydrochloride

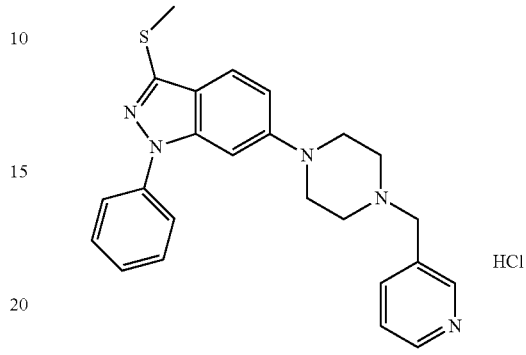

The title compound was prepared according to the procedure as described in Example 18, reacting the product in Example 31.

MS (m/z): 416 [M−HCl+H]$^+$; $^1$HNMR (400 MHz, D$_2$O, ppm): δ 8.93-8.86 (2H, m), 8.60 (1H, m), 7.57-7.44 (6H, m), 6.97-6.75 (2H, m), 4.59 (2H, m), 3.45 (8H, m), 2.59-2.50 (3H, m).

Example 33

(4-(3-(Methylthio)-1-phenyl-1H-indazol-6-yl)piperazin-1-yl)(pyrrolidin-2-yl)methanone hydrochloride

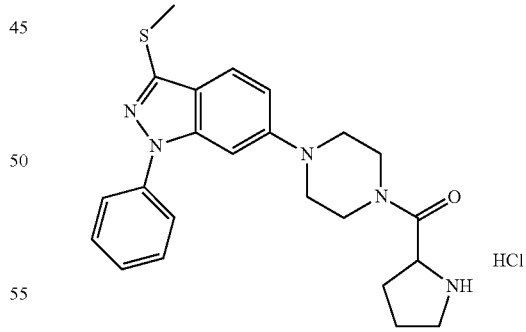

The title compound was prepared according to the procedure as described in Example 16 reacting N-Boc proline, followed by de-protection of the N-Boc group by reacting with HCl.

MS (m/z): 421 [M−HCl+H]$^+$; $^1$HNMR (400 MHz, D$_2$O, ppm): δ 7.50-7.36 (6H, m), 6.83 (1H, m), 4.65 (1H, m) 3.63-2.94 (10H, m), 2.49 (3H, s), 2.42 (1H, m), 2.05 (2H, m), 1.85 (1H, m).

Example 34

(4-(3-(Methylthio)-1-phenyl-1H-indazol-6-yl)piperazin-1-yl)(piperidin-4-yl)methanone hydrochloride

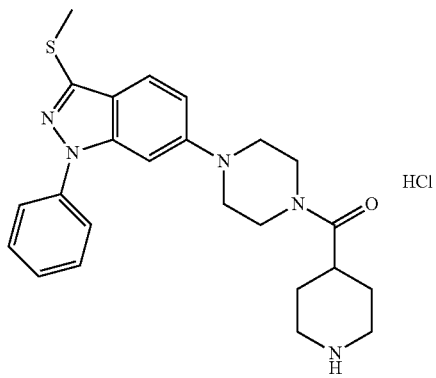 [SMILES: CSc1nn(-c2ccccc2)c2cc(N3CCN(C(=O)C4CCNCC4)CC3)ccc12 ; Cl]

The title compound was prepared according to the procedure as described in Example 16 reacting piperidine-1,4-dicarboxylic acid mono-tert-butyl ester, followed by de-protection of the N-Boc group by reacting with HCl MS (m/z): 435 [M−HCl+H]$^+$; $^1$HNMR (400 MHz, D$_2$O, ppm): δ 7.29 (4H, m), 7.14 (1H, m), 7.05 (1H, m) 6.49 (1H, m), 6.38 (1H, m), 3.51-3.46 (6H, m), 2.87-2.54 (7H, m), 2.34 (3H, s), 1.70 (4H, m).

Example 35

(4-(3-(Methylthio)-1-phenyl-1H-indazol-6-yl)piperazin-1-yl)(piperidin-2-yl)methanone

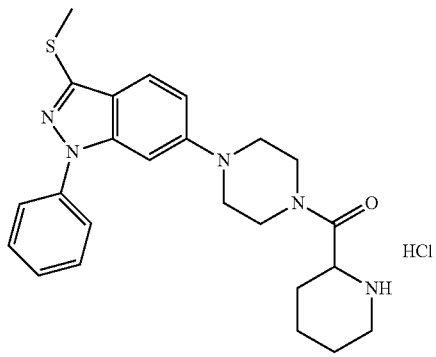 [SMILES: CSc1nn(-c2ccccc2)c2cc(N3CCN(C(=O)C4CCCCN4)CC3)ccc12 ; Cl]

The title compound was prepared according to the procedure as described in Example 16 reacting piperidine-1,2-dicarboxylic acid mono-tert-butyl ester, followed by de-protection by reacting with HCl.

MS (m/z): 436 [M−HCl+H]$^+$; $^1$HNMR (400 MHz, D$_2$O, ppm): δ 7.52-7.48 (2H, m), 7.43-7.38 (4H, m) 6.84-6.77 (2H, m), 4.28 (1H, m), 3.68-3.31 (5H, m), 3.20-2.94 (5H, m), 2.51 (3H, s), 2.04 (1H, m), 1.87 (2H, m), 1.58 (3H, m).

Example 36

3-Ethyl-1-phenyl-6-(4-piperazin-1-yl-piperidin-1-yl)-1H-indazole hydrochloride

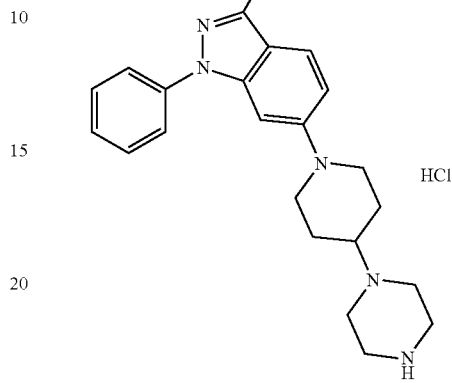

Step A:
4-Bromo-2-fluoro-N-methoxy-N-methyl-benzamide

Into a 1000-mL round-bottom flask, was placed a solution of 4-bromo-2-fluorobenzoic acid (50 g, 229.36 mmol, 1.00 equiv) in dichloromethane (600 mL), N-methoxymethanamine hydrochloride (25 g, 257.73 mmol, 1.10 equiv). To the resulting mixture was added DIC (32 g, 253.97 mmol, 1.10 equiv) at 0° C. The resulting solution was stirred for 4 h at room temperature. The reaction was then quenched by the addition of water (500 mL). The solids were filtered out. The resulting solution was extracted with DCM (2×300 mL) and the organic layers combined. The resulting mixture was washed with water (2×300 mL), and sodium carbonate (1×300 mL). The resulting mixture was washed with brine (1×300 mL), then dried over anhydrous sodium sulfate and concentrated under vacuum to yield 4-bromo-2-fluoro-N-methoxy-N-methylbenzamide as colorless oil.

Step B: 1-(4-Bromo-2-fluoro-phenyl)-propan-1-one

Into a 1000-mL 4-necked round-bottom flask purged and maintained with an inert atmosphere of nitrogen, was placed a solution of 4-bromo-2-fluoro-N-methoxy-N-methylbenzamide (60 g, 229.01 mmol, 1.00 equiv) in tetrahydrofuran (200 mL). To the resulting mixture was then added ethylmagnesium bromide (2M) (185 mL, 1.60 equiv) dropwise with stirring at −20° C. The resulting solution was stirred for 2 h at room temperature, then cooled to 0° C. with a water/ice bath. The reaction was then quenched by the addition of NH$_4$Cl/H$_2$O (500 mL). The resulting solution was extracted with ethyl acetate (3×300 mL) and the organic layers combined. The resulting mixture was washed with water (1×300 mL) and brine (1×300 mL), then dried over anhydrous sodium sulfate and concentrated under vacuum. The residue was applied onto a silica gel column with ethyl acetate/petroleum ether (1:20) to yield 1-(4-bromo-2-fluorophenyl)propan-1-one as a white solid.

Step C: N-[1-(4-Bromo-2-fluoro-phenyl)-propylidene]-N'-phenyl-hydrazine

Into a 1000-mL round-bottom flask, was placed a solution of 1-(4-bromo-2-fluorophenyl)propan-1-one (32 g, 138.53 mmol, 1.00 equiv) in ethanol (300 mL), 1-phenylhydrazine (15.0 g, 138.89 mmol, 1.00 equiv), TSA-H$_2$O (1.32 g, 6.95 mmol, 0.05 equiv). The resulting solution was heated to reflux for 1 h in an oil bath. The resulting mixture was concentrated under vacuum to yield (Z)-1-(1-(4-bromo-2-fluorophenyl)propylidene)-2-phenylhydrazine and (E)-1-(1-(4-bromo-2-fluorophenyl)propylidene)-2-phenylhydrazine as a yellow solid. MS: 322 (MH$^+$)

Step D: 6-Bromo-3-ethyl-1-phenyl-1H-indazole

Into a 1000-mL 3-necked round-bottom flask, was placed a solution of (Z)-1-(1-(4-bromo-2-fluorophenyl)propylidene)-2-phenylhydrazine and (E)-1-(1-(4-bromo-2-fluorophenyl)propylidene)-2-phenylhydrazine (44.3 g, 138.01 mmol, 1.00 equiv) in N,N-dimethylformamide (400 mL), potassium carbonate (83 g, 601.45 mmol, 4.40 equiv). The resulting solution was stirred for 2 days at 100° C. in an oil bath. The resulting mixture was concentrated under vacuum. The resulting solution was diluted with water (500 mL). The resulting solution was extracted with ethyl acetate (2×300 mL) and the organic layers combined. The resulting mixture was washed with water (2×300 mL) and brine (1×300 mL). The resulting mixture was dried over anhydrous sodium sulfate and concentrated under vacuum. The residue was applied onto a silica gel column with ethyl acetate/petroleum ether (1:50) to yield 6-bromo-3-ethyl-1-phenyl-1H-indazole as a yellow solid.

MS (m/z): 301 [M+H]$^+$; $^1$HNMR (400 MHz, CDCl$_3$, ppm): δ 1.42-1.46 (3H, t), 3.01-3.07 (2H, dd), 7.25-7.86 (8H, m).

Step E: 3-Ethyl-1-phenyl-6-(4-piperazin-1-yl-piperidin-1-yl)-1H-indazole hydrochloride Into a 100-mL 3-necked round-bottom flask purged and maintained with an inert atmosphere of nitrogen, was placed a solution of 6-bromo-3-ethyl-1-phenyl-1H-indazole (300 mg, 1.00 mmol, 1.00 equiv) in toluene (30 mL), tert-butyl 4-(piperidin-4-yl)piperazine-1-carboxylate (269 mg, 1.00 mmol, 1.00 equiv), Pd(OAc)$_2$ (2.24 mg, 0.01 mmol, 0.01 equiv), Cs$_2$CO$_3$ (482 mg, 2.50 mmol, 2.50 equiv), BINAP (18.7 mg, 0.03 mmol, 0.03 equiv). The resulting solution was heated to reflux overnight in an oil bath. The resulting mixture was concentrated under vacuum. The residue was applied onto a silica gel column with dichloromethane/methanol (100:1). The residue was dissolved in hydrogen chloride/MeOH (50 mL) and then stirred for 2 hours at room temperature. The resulting mixture was concentrated under vacuum and the residue by re-crystallization from diethyl ether (50 mL). The solids were collected by filtration, was dried in an oven under reduced pressure to yield 3-ethyl-1-phenyl-6-(4-(piperazin-1-yl)piperidin-1-yl)-1H-indazole hydrochloride as a white solid.

MS (m/z): 390 [M−HCl+H]$^+$; $^1$HNMR (400 MHz, DMSO, ppm): δ 1.32-1.35 (3H, t), 1.86-1.89 (2H, m), 2.20-2.22 (2H, m), 2.80-2.84 (2H, m), 2.91-2.96 (2H, dd), 3.33-3.98 (11H, m), 7.09-7.74 (8H, m).

Example 37

3-Ethyl-1-phenyl-6-(4-(piperidin-4-yloxy)phenyl)-1H-indazole hydrochloride

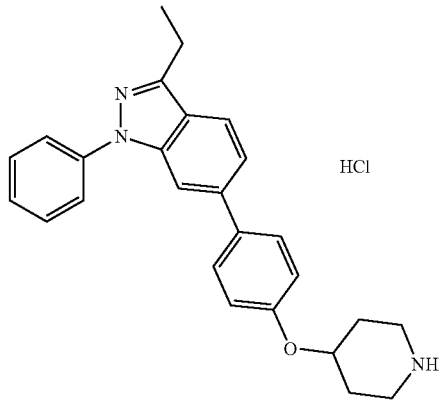 [SMILES: CCc1nn(-c2ccccc2)c2cc(-c3ccc(OC4CCNCC4)cc3)ccc12 ; Cl]

Into a 100-mL 3-necked round-bottom flask purged and maintained with an inert atmosphere of nitrogen, was placed a solution of 6-bromo-3-ethyl-1-phenyl-1H-indazole (225 mg, 0.75 mmol, 1.50 equiv) in toluene/ethanol at 5:1 (30 mL), tert-butyl 4-(4-(4,4,5,5-tetramethyl-1,3,2-dioxaborolan-2-yl)phenoxy)piperidine-1-carboxylate (200 mg, 0.50 mmol, 1.00 equiv), potassium carbonate (117 mg, 0.85 mmol, 1.70 equiv), Pd(PPh$_3$)$_4$ (11.5 mg, 0.01 mmol, 0.02 equiv). The resulting solution was heated to reflux overnight in an oil bath. The resulting mixture was concentrated under vacuum. The residue was applied onto a silica gel column with ethyl acetate/petroleum ether (1:20). The residue was dissolved in hydrogen chloride/EtOAc (30 mL). After stirring for 30 min, the resulting mixture was concentrated under vacuum. The residue was purified by re-crystallization from diethyl ether to yield 3-ethyl-1-phenyl-6-(4-(piperidin-4-yloxy)phenyl)-1H-indazole hydrochloride as a white solid.

MS (m/z): 398 [M−HCl+H]$^+$

Example 38

N-(3-Ethyl-1-phenyl-1H-indazol-6-yl)-1H-benzo[d]imidazole-5-carboxamide

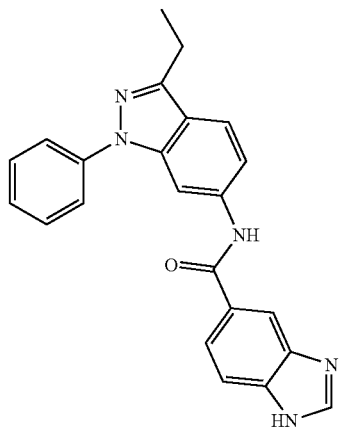 [SMILES: CCc1nn(-c2ccccc2)c2cc(NC(=O)c3ccc4[nH]cnc4c3)ccc12]

Step A: 3-Ethyl-1-phenyl-1H-indazol-6-ylamine

Into a 100-mL 3-necked round-bottom flask purged and maintained with an inert atmosphere of nitrogen, was placed a solution of 6-bromo-3-ethyl-1-phenyl-1H-indazole (300 mg, 1.00 mmol, 1.00 equiv) in tetrahydrofuran (30 mL), Xantphos (64 mg, 0.11 mmol, 0.11 equiv), Pd(OAc)$_2$ (33 mg, 0.15 mmol, 0.15 equiv), Cs$_2$CO$_3$ (214 mg, 1.11 mmol, 1.11 equiv), diphenylmethanimine (200 mg, 1.10 mmol, 1.10 equiv). The resulting solution was heated to reflux for 16 h in an oil bath. The resulting mixture was concentrated under vacuum. The residue was dissolved in tetrahydrofuran/3N hydrogen chloride (15 mL/5 mL). The resulting solution was stirred for an additional 2 h at room temperature, then concentrated under vacuum. The residue was applied onto a silica gel column with ethyl acetate:MeOH:NH$_4$OH (30:1:0.3) to yield 3-ethyl-1-phenyl-1H-indazol-6-amine as yellow oil.

MS (m/z): 238 [M+H]$^+$

Step B: 3-Ethyl-1-phenyl-1H-indazol-6-ylamine hydrochloride

Into a 100-mL round-bottom flask, was placed 3-ethyl-1-phenyl-1H-indazol-6-amine (190 mg, 0.80 mmol, 1.00 equiv), hydrogen chloride/EtOAc (30 mL). The resulting solution was stirred for 30 min at room temperature. The resulting mixture was concentrated under vacuum. The resulting mixture was washed with diethyl ether (1×50 mL). The solids were collected by filtration to yield 3-ethyl-1-phenyl-1H-indazol-6-amine hydrochloride as a white solid.

MS (m/z): 238 [M−HCl+H]$^+$; $^1$HNMR (400 MHz, DMSO, ppm): δ 1.37-1.39 (3H, t), 2.97-3.04 (2H, dd), 7.10-7.91 (8H, m).

Step C: N-(3-ethyl-1-phenyl-1H-indazol-6-yl)-1H-benzo[d]imidazole-5-carboxamide

Into a 100-mL 3-necked round-bottom flask, was placed a solution of 3-ethyl-1-phenyl-1H-indazol-6-amine hydrochloride (300 mg, 1.10 mmol, 1.00 equiv) in N,N-dimethylformamide (30 mL), tributylamine (492 mg, 2.66 mmol, 2.50 equiv), 1H-benzo[d]imidazole-5-carboxylic acid (180 mg, 1.11 mmol, 1.00 equiv), 2-chloro-1-methylpyridinium iodide (330 mg, 1.29 mmol, 1.20 equiv). The resulting solution was stirred for 2 days at 100° C. in an oil bath. The resulting mixture was concentrated under vacuum. The residue was applied onto a silica gel column with dichloromethane/methanol (50:1). The resulting mixture was diluted with methanol (10 mL) and the solids were washed with diethyl ether (1×50 mL) to yield N-(3-ethyl-1-phenyl-1H-indazol-6-yl)-1H-benzo[d]imidazole-5-carboxamide as a yellow solid.

MS (m/z): 382 [M+H]$^+$; $^1$HNMR (300 MHz, DMSO, ppm): δ 1.39 (3H, t), 3.03 (2H, q), 7.39-8.53 (11H, m), 9.36 (1H, s), 10.69 (1H, s).

Example 39

3-Cyano-N-(3-ethyl-1-phenyl-1H-indazol-6-yl)benzamide

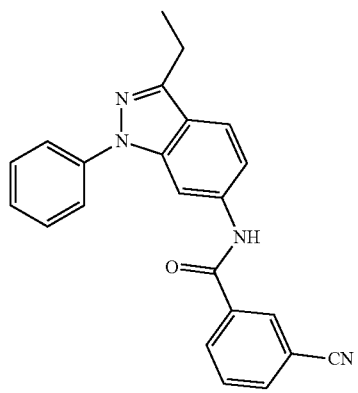 [SMILES: CCc1nn(-c2ccccc2)c2cc(NC(=O)c3cccc(C#N)c3)ccc12]

Into a 100-mL round-bottom flask, was placed a solution of 3-ethyl-1-phenyl-1H-indazol-6-amine hydrochloride (1 g, 3.60 mmol, 1.00 equiv, 98%) in dichloromethane (50 mL), 3-cyanobenzoic acid (646.8 mg, 4.31 mmol, 1.20 equiv), TEA (445 mg, 4.31 mmol, 1.20 equiv), EDCI (845 mg, 4.31 mmol, 1.20 equiv). The resulting solution was stirred for 5 h at room temperature. The resulting mixture was concentrated under vacuum. The residue was applied onto a silica gel column with ethyl acetate/petroleum ether (1:3). The collected fractions were combined and concentrated under vacuum to yield 3-cyano-N-(3-ethyl-1-phenyl-1H-indazol-6-yl)benzamide as a white solid.

MS (m/z): 367 [M+H]$^+$

Example 40

3-Carbamimidoyl-N-(3-ethyl-1-phenyl-1H-indazol-6-yl)benzamide acetate

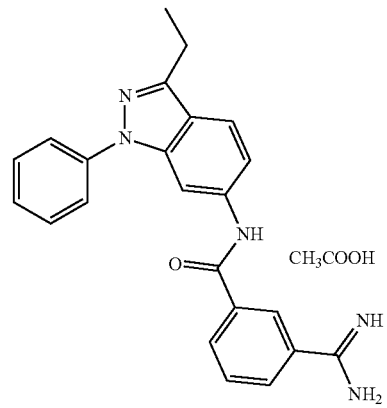

Into a 100-mL 3-necked round-bottom flask, was placed a solution of 3-cyano-N-(3-ethyl-1-phenyl-1H-indazol-6-yl)benzamide (600 mg, 1.64 mmol, 1.00 equiv) in methanol/CHCl$_3$ (50/20 mL). To the resulting mixture, HCl (g) was bubbled through at −20° C. in 20 min. The resulting solution was stirred for 3 days at 5° C. in a water/ice bath. The resulting solution was evaporated. To the resulting residue was then added a solution of NH$_4$OAc (1.26 g, 16.36 mmol, 10.00 equiv) in methanol (30 mL). The resulting solution was stirred for an additional 36 h at room temperature. The solids were collected by filtration, then dried in an oven under reduced pressure to yield 3-carbamimidoyl-N-(3-ethyl-1-phenyl-1H-indazol-6-yl)benzamide acetate as a white solid.

MS (m/z): 384 [M-CH$_3$COOH+H]$^+$; $^1$HNMR (300 MHz, DMSO, ppm): δ 1.39 (3H, t), 1.73 (3H, s), 3.02 (2H, dd), 7.37-8.53 (12H, m), 10.71 (1H, s).

Example 41

3-Ethyl-1-phenyl-6-(1-(piperidin-4-yl)azetidin-3-yloxy)-1H-indazole hydrochloride

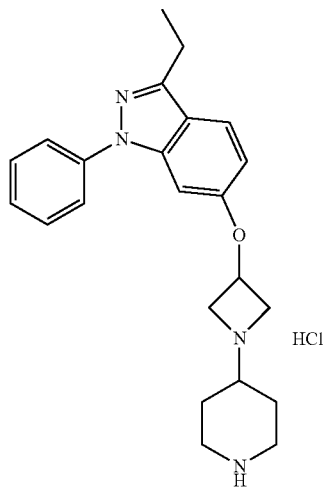 [SMILES: CCc1nn(-c2ccccc2)c2cc(OC3CN(C4CCNCC4)C3)ccc12 ; Cl]

Step A: tert-butyl 4-(3-(methylsulfonyloxy)azetidin-1-yl)piperidine-1-carboxylate Into a 100-mL 3-necked round-bottom flask, was placed a solution of tert-butyl 4-(3-hydroxyazetidin-1-yl)piperidine-1-carboxylate (300 mg, 1.15 mmol, 1.00 equiv, 98%) in dichloromethane (20 mL), TEA (240 mg, 2.33 mmol, 2.00 equiv, 98%). To the resulting mixture was added MsCl (0.6 mg, 0.01 mmol, 4.50 equiv, 98%) dropwise with stirring. The resulting solution was stirred for 2 h at room temperature in an ice/salt bath. The reaction was then quenched by the addition of water. The resulting solution was extracted with dichloromethane (2×50 mL) and the organic layers combined. The resulting mixture was washed with sodium chloride/$H_2O$ (1×100 mL). The resulting mixture was dried over anhydrous sodium sulfate and concentrated under vacuum to yield tert-butyl 4-(3-(methylsulfonyloxy)azetidin-1-yl)piperidine-1-carboxylate as a white solid. MS: 335 ($MH^+$).

Step B: 3-ethyl-1-phenyl-1H-indazol-6-ylboronic acid

Into a 250-mL 3-necked round-bottom flask purged and maintained with an inert atmosphere of nitrogen, was placed a solution of 6-bromo-3-ethyl-1-phenyl-1H-indazole (2 g, 6.64 mmol, 1.00 equiv) in tetrahydrofuran (20 mL). To the resulting mixture was then added a solution of n-BuLi (4 mL, 1.40 equiv) in tetrahydrofuran (5 mL) dropwise with stirring at −78° C. in 5 min. The resulting mixture was stirred for 30 min at the temperature. To the resulting mixture was then added a solution of tripropyl borate (1.49 g, 7.93 mmol, 1.20 equiv) in tetrahydrofuran (5 mL) dropwise with stirring at −78° C. in 5 min. The resulting solution was stirred for 1 h at −78° C. in a liquid nitrogen bath. The reaction was then quenched by the addition of water (30 mL). The resulting solution was extracted with ethyl acetate (2×50 mL), the organic layers combined and dried over anhydrous sodium sulfate, then concentrated under vacuum. The residue was applied onto a silica gel column with ethyl acetate/petroleum ether (1:5) to yield 3-ethyl-1-phenyl-1H-indazol-6-ylboronic acid as a white solid.

Step C: 3-ethyl-1-phenyl-1H-indazol-6-ol

Into a 50-mL round-bottom flask, was placed a solution of 3-ethyl-1-phenyl-1H-indazol-6-ylboronic acid (1.4 g, 5.26 mmol, 1.00 equiv) in ethyl acetate (10 mL). To the resulting mixture was then added $H_2O_2$ (2 mL) dropwise with stirring at 0° C. The resulting solution was stirred for 2 h at 0° C. in a water/ice bath. The resulting mixture was concentrated under vacuum. The residue was applied onto a silica gel column with ethyl acetate/petroleum ether (1:10) to yield 3-ethyl-1-phenyl-1H-indazol-6-ol as a white solid. MS: 239 ($MH^+$).

Step D: 3-ethyl-1-phenyl-6-(1-(piperidin-4-yl)azetidin-3-yloxy)-1H-indazole hydrochloride Into a 100-mL 3-necked round-bottom flask purged and maintained with an inert atmosphere of nitrogen, was placed a solution of 3-ethyl-1-phenyl-1H-indazol-6-ol (215 mg, 0.90 mmol, 1.00 equiv) in N,N-dimethylformamide (20 mL), $Cs_2CO_3$ (383 mg, 1.17 mmol, 1.30 equiv). To the resulting mixture was then added a solution of tert-butyl 4-(3-(methylsulfonyloxy)azetidin-1-yl)piperidine-1-carboxylate (300 mg, 0.90 mmol, 1.00 equiv) in N,N-dimethylformamide (5 mL) dropwise with stirring at 20° C. The resulting solution was stirred overnight at 100° C. in an oil bath. The resulting mixture was then concentrated under vacuum. The residue was applied onto a silica gel column with dichloromethane/methanol (200:1). The residue was dissolved in hydrogen chloride/EtOAc (2M, 50 mL). The resulting mixture was concentrated under vacuum. The residue was purified by re-crystallization from diethyl ether. The solids were collected by filtration to yield 3-ethyl-1-phenyl-6-(1-(piperidin-4-yl)azetidin-3-yloxy)-1H-indazole hydrochloride as a yellow solid.

MS (m/z): 377 $[M-HCl+H]^+$; $^1$HNMR (400 MHz, $D_2O$, ppm): δ 1.26 (3H, t), 1.62 (2H, m), 2.25 (2H, m), 2.91 (4H, m), 3.53 (3H, m), 4.28 (2H, d), 5.13 (1H, s), 6.81-7.82 (8H, m).

Example 42

3-Ethyl-1-phenyl-6-(piperazin-1-yl)-1H-indazole

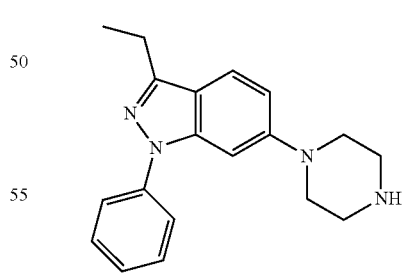

Into a 50-mL 3-necked round-bottom flask, was placed a solution of 6-bromo-3-ethyl-1-phenyl-1H-indazole (0.10 g, 0.33 mmol, 1.00 equiv) in toluene (20 mL), piperazine (0.14 g, 1.628 mmol, 2.00 equiv), $Cs_2CO_3$ (0.16 g, 5.00 mmol, 1.50 equiv), $Pd(OAc)_2$ (20 mg, 0.09 mmol, 0.03 equiv), BINAP (20 mg, 0.03 mmol, 0.03 equiv). The resulting solution was stirred for 20 h at 100° C. in an oil bath. The solids were filtered out. The residue was applied onto a silica gel column with dichloromethane/methanol (20:1). The resulting residue (50 mg) was purified by Prep-HPLC with the following conditions (AGILENT Pre-HPLC (UV-Directed)): Column, SunFire Prep C18, 5 um, 19*100 mm; mobile phase, water with 0.05% TFA and MeOH (10% MeOH up to 55% in 2.5 min, hold 55% in 2.5 min, up to 100% in 0.1 min, hold 100% in 0.3 min, down to 10% in 0.1 min); Detector, UV254 nm to yield 3-ethyl-1-phenyl-6-(piperazin-1-yl)-1H-indazole as a yellow solid.

MS (m/z): 307 [M+H]$^+$; $^1$HNMR (300 MHz, CD$_3$OD, ppm): δ 1.40-1.45 (3H, m), 2.98-3.06 (2H, m), 3.41-3.50 (8H, m), 7.06-7.07 (2H, m), 7.38-7.43 (1H, m), 7.55-7.76 (5H, m).

Example 43

3-Ethyl-1-phenyl-6-(3-(piperazin-1-yl)pyrrolidin-1-yl)-1H-indazole hydrochloride

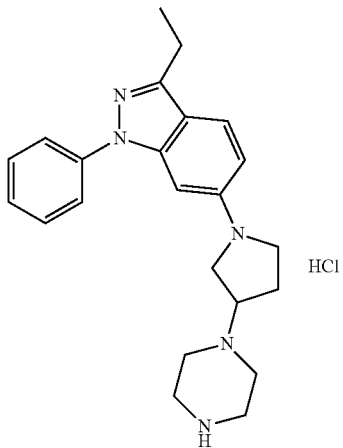 [SMILES: CCc1nn(-c2ccccc2)c2cc(N3CCC(N4CCNCC4)C3)ccc12 ; Cl]

The title compound was prepared according to the procedure as described in Example 36 reacting 4-pyrrolidin-3-yl-piperazine-1-carboxylic acid tert-butyl ester, followed by de-protection with HCl.

MS (m/z): 376 [M−HCl+H]$^+$; $^1$HNMR (400 MHz, D$_2$O, ppm): δ 1.19-1.23 (3H, t), 2.05-2.10 (1H, m), 2.40 (1H, s), 2.76-2.82 (2H, dd), 3.13-3.17 (1H, m), 3.37-3.55 (1H, m), 3.76-3.79 (1H, m), 6.52-6.55 (1H, d), 7.31-7.50 (6H, m).

Example 44

6-(4-(azetidin-3-yl)piperazin-1-yl)-3-ethyl-1-phenyl-1H-indazole hydrochloride

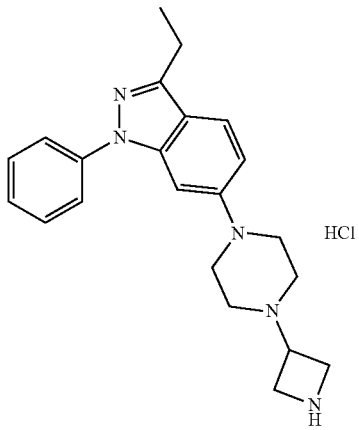 [SMILES: CCc1nn(-c2ccccc2)c2cc(N3CCN(C4CNC4)CC3)ccc12 ; Cl]

The title compound was prepared according to the procedure as described in Example 36 reacting 3-piperazin-1-yl-azetidine-1-carboxylic acid tert-butyl ester, followed by de-protection with HCl.

MS (m/z): 362 [M−HCl+H]$^+$; $^1$HNMR (400 MHz, CD$_3$OD, ppm): δ 1.42-1.47 (3H, t), 3.02-3.09 (2H, dd), 3.40 (4H, s), 3.70 (4H, s), 4.39-4.41 (3H, m), 4.65-4.70 (2H, m), 7.15-7.83 (8H, m).

Example 45

3-Ethyl-1-phenyl-6-(4-(pyrrolidin-3-yl)piperazin-1-yl)-1H-indazole hydrochloride

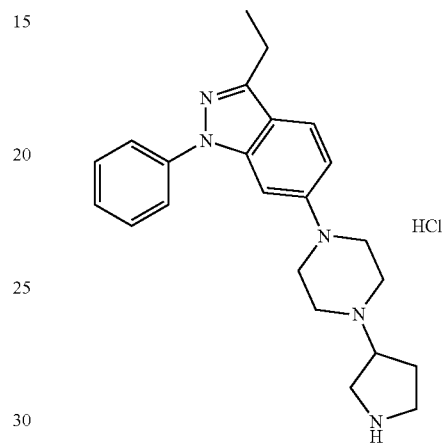

The title compound was prepared according to the procedure as described in Example 36 reacting 3-piperazin-1-yl-pyrrolidine-1-carboxylic acid tert-butyl ester, followed by de-protection with HCl.

MS (m/z): 376 [M−HCl+H]$^+$; $^1$HNMR (400 MHz, D$_2$O, ppm): δ 1.17-1.23 (3H, t), 2.17-2.22 (1H, m), 2.55-2.60 (1H, m), 2.81-2.84 (2H, m), 3.29-3.58 (11H, m), 3.81-3.86 (1H, m), 4.03-4.09 (1H, m), 6.84-6.92 (2H, m), 7.35-7.67 (6H, m).

Example 46

3-Ethyl-1-phenyl-6-(4-(piperidin-4-yl)piperazin-1-yl)-1H-indazole hydrochloride

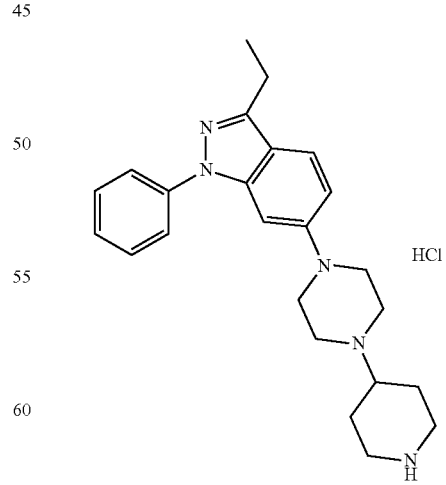

The title compound was prepared according to the procedure as described in Example 36 reacting 4-piperazin-1-yl-piperidine-1-carboxylic acid tert-butyl ester, followed by de-protection with HCl.

MS (m/z): 390 [M−HCl+H]⁺; ¹HNMR (400 MHz, D₂O, ppm): δ 1.22 (3H, s), 1.83-1.92 (2H, m), 2.35-2.38 (2H, m), 2.86-3.85 (15H, m), 6.89-6.95 (2H, m), 7.36-7.67 (6H, m).

Example 47

3-Ethyl-1-phenyl-6-(4-(pyridin-4-yl)piperazin-1-yl)-1H-indazole hydrochloride

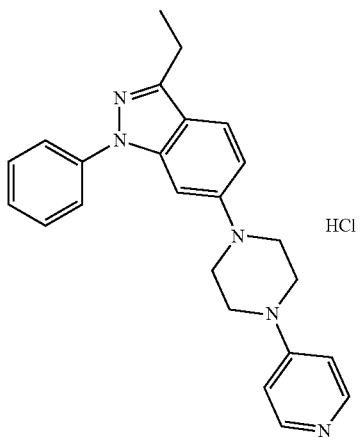 [SMILES: CCc1nn(-c2ccccc2)c2cc(N3CCN(c4ccncc4)CC3)ccc12 ; Cl]

The title compound was prepared according to the procedure as described in Example 36 reacting 1-pyridin-4-yl-piperazine.

MS (m/z): 384 [M−HCl+H]⁺; ¹HNMR (400 MHz, DMSO, ppm): δ 1.32-1.36 (3H, t), 2.91-2.95 (2H, dd), 3.44 (4H, s), 3.89 (4H, m), 7.05-7.75 (10H, m), 8.27 (2H, s).

Example 48

1-(3-Ethyl-1-phenyl-1H-indazol-6-yl)-3-(pyrrolidin-3-yl)imidazolidin-2-one hydrochloride

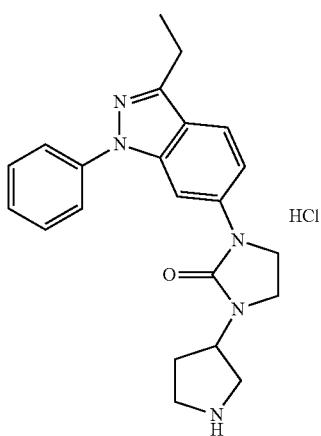 [SMILES: CCc1nn(-c2ccccc2)c2cc(N3CCN(C4CCNC4)C3=O)ccc12 ; Cl]

The title compound was prepared according to the procedure as described in Example 36 reacting 3-(2-oxo-imidazolidin-1-yl)-pyrrolidine-1-carboxylic acid tert-butyl ester, followed by de-protection with HCl.

MS (m/z): [M−HCl+H]⁺; ¹HNMR (400 MHz, D₂O, ppm): δ 1.13-1.16 (3H, t), 1.91-1.96 (1H, m), 2.08-2.13 (1H, m), 2.68-2.70 (2H, dd), 3.10-3.41 (8H, m), 4.30-4.34 (1H, m), 6.76-7.42 (8H, m).

Example 49

1-(3-Ethyl-1-phenyl-1H-indazol-6-yl)-3-(piperidin-4-yl)imidazolidin-2-one hydrochloride

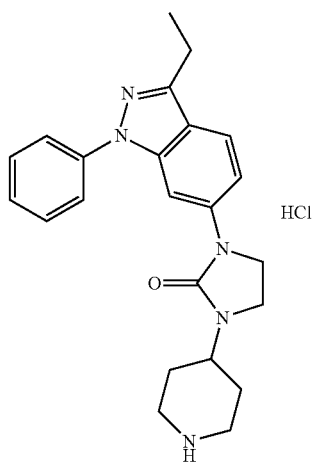 [SMILES: CCc1nn(-c2ccccc2)c2cc(N3CCN(C4CCNCC4)C3=O)ccc12 ; Cl]

The title compound was prepared according to the procedure as described in Example 36 reacting 4-(2-oxo-imidazolidin-1-yl)-piperidine-1-carboxylic acid tert-butyl ester, followed by de-protection with HCl.

MS (m/z): 390 [M−HCl+H]⁺; ¹HNMR (400 MHz, D₂O, ppm): δ 1.04-1.07 (3H, t), 1.64 (4H, m), 2.57 (2H, m), 2.77 (2H, s), 2.90 (4H, m), 3.38 (2H, d), 3.60 (1H, m), 6.5-7.34 (8H, m).

Example 50

3-Ethyl-6-(hexahydropyrrolo[3,4-c]pyrrol-2(1H)-yl)-1-phenyl-1H-indazolehydrochloride

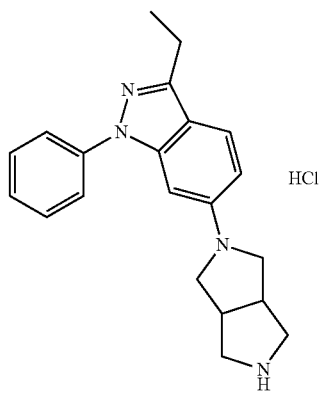 [SMILES: CCc1nn(-c2ccccc2)c2cc(N3CC4CNCC4C3)ccc12 ; Cl]

The title compound was prepared according to the procedure as described in Example 36 reacting hexahydro-pyrrolo[3,4-c]pyrrole-2-carboxylic acid tert-butyl ester, followed by de-protection with HCl.

MS (m/z): 333 [M−HCl+H]+; 1HNMR (400 MHz, DMSO, ppm): δ 1.33 (3H, t), 2.92 (2H, q), 3.08 (4H, m), 3.42 (6H, m), 3.89 (3H, s), 6.71-7.72 (8H, m), 9.35 (2H, s).

Example 51

6-(2,7-Diaza-spiro[4.4]non-2-yl)-3-ethyl-1-phenyl-1H-indazole hydrochloride

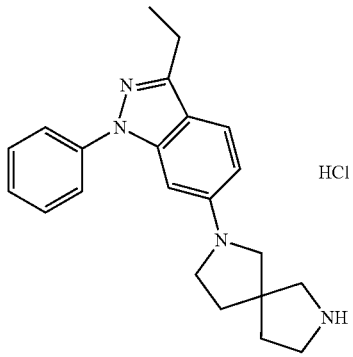 [SMILES: CCc1nn(-c2ccccc2)c2cc(N3CCC4(CCNC4)C3)ccc12 ; Cl]

The title compound was prepared according to the procedure as described in Example 36 reacting 2,7-diaza-spiro[4.4]nonane-2-carboxylic acid tert-butyl ester, followed by de-protection with HCl.

MS (m/z): 347 [M−HCl+H]+; 1HNMR (400 MHz, D2O, ppm): δ 1.22 (3H, t), 1.92 (4H, m), 2.82 (2H, m), 3.35 (8H, m), 6.32-7.5 (8H, m).

Example 52

3-Ethyl-1-phenyl-6-(4-(piperazin-1-yl)phenyl)-1H-indazole hydrochloride

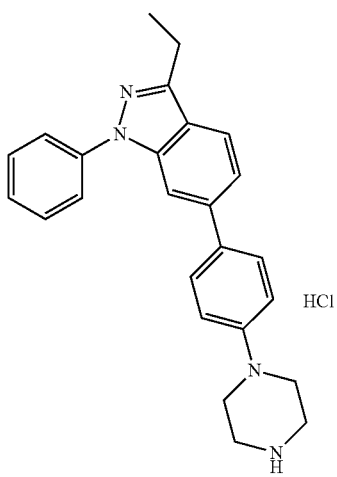 [SMILES: CCc1nn(-c2ccccc2)c2cc(-c3ccc(N4CCNCC4)cc3)ccc12 ; Cl]

The title compound was prepared according to the procedure as described in Example 58 reacting 4-[4-(4,4,5,5-Tetramethyl-[1,3,2]dioxaborolan-2-yl)-phenyl]-piperidine-1-carboxylic acid tert-butyl ester, followed by de-protection with HCl.

MS (m/z): 383 [M−HCl+H]+; 1HNMR (400 MHz, DMSO, ppm): δ 1.39 (3H, t), 3.04 (2H, q), 3.23 (4H, s), 3.43 (4H, s), 5.11 (4H, m), 7.09-7.92 (8H, m), 9.29 (2H, s).

Example 53

3-Ethyl-1-phenyl-6-(3-(pyrrolidin-1-yl)phenyl)-1H-indazole hydrochloride

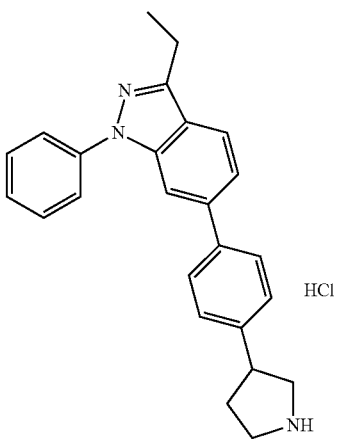 [SMILES: CCc1nn(-c2ccccc2)c2cc(-c3ccc(C4CCNC4)cc3)ccc12 ; Cl]

The title compound was prepared according to the procedure as described in Example 58 reacting 3-[4-(4,4,5,5-tetramethyl-[1,3,2]dioxaborolan-2-yl)-phenoxy]-pyrrolidine-1-carboxylic acid tert-butyl ester, followed by de-protection with HCl.

MS (m/z): 371 [M−HCl+H]+

Example 54

3-Ethyl-6-(4-methylpiperazin-1-yl)-1-phenyl-1H-indazole

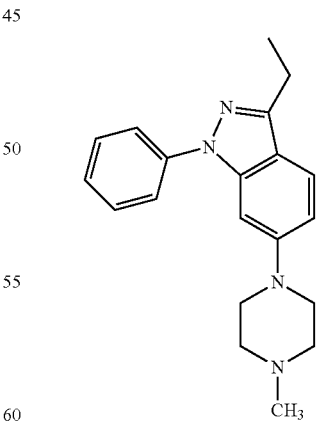

The title compound was prepared according to the procedure as described in Example 36 reacting 1-methyl-piperazine.

MS (m/z): 321 [M+H]+; 1HNMR (300 MHz, CDCl3, ppm): δ 1.43-1.48 (3H, t), 2.91 (3H, s), 3.00-3.08 (4H, m), 3.42-3.50 (2H, t), 3.70-3.73 (4H, d), 6.88 (1H, d), 7.08 (1H,), 7.34-7.39 (1H, m), 7.53-7.58 (2H, m), 7.66-7.69 (3H, m).

Example 55

3-Ethyl-6-(4-ethylpiperazin-1-yl)-1-phenyl-1H-indazole

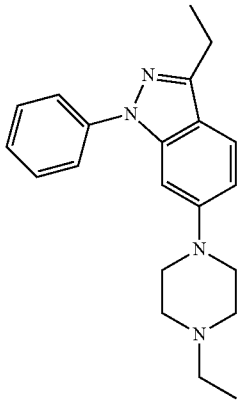 [SMILES: CCc1nn(-c2ccccc2)c2cc(N3CCN(CC)CC3)ccc12]

The title compound was prepared according to the procedure as described in Example 36 reacting 1-ethyl-piperazine.

MS (m/z): 335 [M+H]$^+$; $^1$HNMR (300 MHz, CD$_3$OD, ppm): δ 1.14-1.19 (3H, t), 1.39-1.44 (3H, t), 2.49-2.56 (2H, dd), 2.66-2.69 (4H, t), 2.96-3.04 (2H, dd), 3.27-3.33 (4H, m), 7.00-7.06 (2H, m), 7.36-7.41 (1H, t), 7.54-7.59 (2H, m), 7.65-7.68 (3H, m).

Example 56

3-Ethyl-6-(3-methylpiperazin-1-yl)-1-phenyl-1H-indazole

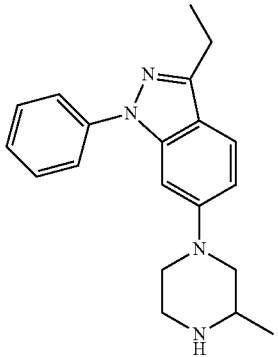 [SMILES: CCc1nn(-c2ccccc2)c2cc(N3CCNC(C)C3)ccc12]

The title compound was prepared according to the procedure as described in Example 36 reacting 2-methyl-piperazine-1-carboxylic acid tert-butyl ester, followed by de-protection with HCl.

ESMS (m/z): 321 [M+H]$^+$; $^1$HNMR: (300 MHz, CD$_3$OD, ppm): 1.40-1.45 (6H, m), 2.83-2.91 (1H, t), 2.98-3.13 (3H, m), 3.38-3.39 (1H, d), 3.51-3.55 (2H, d), 3.83-3.92 (2H, t), 7.07-7.09 (2H, d), 7.38-7.42 (1H, m), 7.56-7.75 (5H, m).

Example 57

3-Methyl-1-phenyl-6-(4-piperazin-1-yl-piperidin-1-yl)-1H-indazole hydrochloride

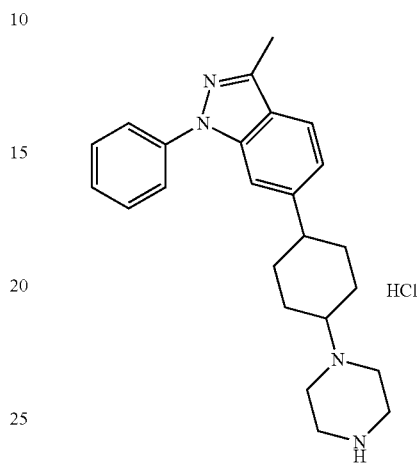

Step A: 1-(4-Bromo-2-fluoro-phenyl)-ethanone

Into a 500-mL 4-necked round-bottom flask purged and maintained with an inert atmosphere of nitrogen, was placed a solution of Mg (6 g, 250.00 mmol, 2.60 equiv) in diethyl ether (50 mL). To the resulting mixture was then added a solution of CH$_3$I (118.4 g, 833.80 mmol, 7.80 equiv) in diethyl ether (75 mL) dropwise with stirring at room temperature. The resulting solution was allowed to react for 1 hr at room temperature. The above methylmagnesium iodide solution (2M) was then added to a solution of 4-bromo-2-fluoro-N-methoxy-N-methylbenzamide (25 g, 95.42 mmol, 1.00 equiv) in tetrahydrofuran (150 mL) dropwise with stirring at −20° C. The resulting solution was stirred for an additional 2 h at room temperature. The resulting mixture was cooled to 0° C. with a water/ice bath. The reaction was then quenched by the addition of NH$_4$Cl/H$_2$O (300 mL). The resulting solution was extracted with ethyl acetate (2×200 ml) and the organic layers combined. The resulting mixture was washed with water (1×200 mL) and brine (1×200 mL). The resulting mixture was dried over NaSO$_4$ and concentrated under vacuum. The residue was applied onto a silica gel column with ethyl acetate:PE (1:20) to yield 1-(4-bromo-2-fluorophenyl)ethanone as colorless oil.

Step B: N-[1-(4-Bromo-2-fluoro-phenyl)-ethylidene]-N'-phenyl-hydrazine

Into a 500-mL round-bottom flask, was placed a solution of 1-(4-bromo-2-fluorophenyl)ethanone (17 g, 78.34 mmol, 1.00 equiv) in ethanol (200 mL), 1-phenylhydrazine (8.5 g, 78.70 mmol, 1.00 equiv), TSA-H$_2$O (740 mg, 3.89 mmol, 0.05 equiv). The resulting solution was heated to reflux for 2 h in an oil bath, then concentrated under vacuum to yield (Z)-1-(1-(4-bromo-2-fluorophenyl)ethylidene)-2-phenylhydrazine and (E)-1-(1-(4-bromo-2-fluorophenyl)ethylidene)-2-phenylhydrazine as a yellow solid. MS (m/z): 307 [M+H]$^+$ Step C: 6-Bromo-3-methyl-1-phenyl-1H-indazole Into a 500-mL 3-necked round-bottom flask, was placed a solution of (E)-1-(1-(4-bromo-2-fluorophenyl)ethylidene)-2-phenylhydrazine and (Z)-1-(1-(4-bromo-2-fluorophenyl)ethylidene)-2-phenylhydrazine (24 g, 78.18 mmol, 1.00 equiv) in N,N-dimethylformamide (200 mL), potassium carbonate (57 g, 413.04 mmol, 5.30 equiv). The resulting solution was stirred for 2 days at 100° C. in an oil bath. The resulting mixture was cooled to room temperature with a water/ice bath, then concentrated under vacuum. The residue was dissolved in water (200 mL). The resulting solution was extracted with ethyl acetate (3×150 mL) and the organic layers combined and dried over anhydrous sodium sulfate, then concentrated under vacuum. The residue was applied onto a silica gel column with ethyl acetate/petroleum ether (1:20), the resulting mixture was washed with petroleum ether (1×10 mL) to yield 6-bromo-3-methyl-1-phenyl-1H-indazole as a yellow solid. $^1$HNMR (400 MHz, CDCl$_3$, ppm): δ 2.64 (3H, s), 7.30-7.87 (8H, m).

Step D: 3-Methyl-1-phenyl-6-(4-piperazin-1-yl-piperidin-1-yl)-1H-indazole hydrochloride Into a 100-mL 3-necked round-bottom flask purged and maintained with an inert atmosphere of nitrogen, was placed a solution of 6-bromo-3-methyl-1-phenyl-1H-indazole (300 mg, 1.05 mmol, 1.00 equiv) in toluene (30 mL), tert-butyl 4-(piperidin-4-yl)piperazine-1-carboxylate (282 mg, 1.05 mmol, 1.00 equiv), Pd(OAc)$_2$ (2.4 mg, 0.01 mmol, 0.01 equiv), Cs$_2$CO$_3$ (506 mg, 1.55 mmol, 2.50 equiv), BINAP (20 mg, 0.03 mmol, 0.03 equiv). The resulting solution was heated to reflux overnight in an oil bath. The resulting mixture was concentrated under vacuum. The residue was applied onto a silica gel column with dichloromethane/methanol (100:1). The resulting residue was dissolved in hydrogen chloride/MeOH (50 mL). The resulting solution was stirred for 2 hours at room temperature, then concentrated under vacuum. The resulting residue was purified by re-crystallization from diethyl ether. The solids were collected by filtration to yield 3-methyl-1-phenyl-6-(4-(piperazin-1-yl)piperidin-1-yl)-1H-indazole hydrochloride as a white solid.

MS (m/z): 376 [M−HCl+H]$^+$; $^1$HNMR (400 MHz, DMSO, ppm): δ 1.84-1.86 (2H, m), 2.18-2.21 (2H, m), 2.78-2.83 (2H, m), 3.46-3.99 (14H, m), 7.10-7.73 (8H, m).

Example 58

3-Methyl-1-phenyl-6-(4-piperazin-1-yl-phenyl)-1H-indazole hydrochloride

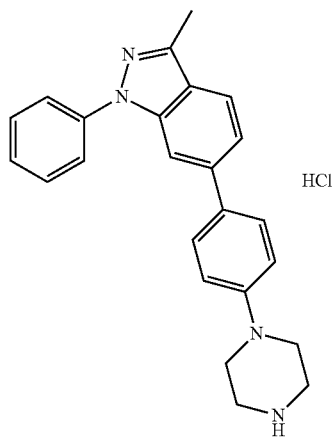 [SMILES: Cc1nn(-c2ccccc2)c2cc(-c3ccc(N4CCNCC4)cc3)ccc12 ; Cl]

Into a 100-mL 3-necked round-bottom flask purged and maintained with an inert atmosphere of nitrogen, was placed a solution of 6-bromo-3-methyl-1-phenyl-1H-indazole (221 mg, 0.76 mmol, 1.00 equiv, 98%) in toluene (50 mL), tert-butyl 4-(4-(4,4,5,5-tetramethyl-1,3,2-dioxaborolan-2-yl)phenyl)piperazine-1-carboxylate (250 mg, 0.63 mmol, 0.83 equiv, 98%), Pd(PPh$_3$)$_4$ (22 mg, 0.02 mmol, 0.03 equiv), potassium carbonate (178 mg, 1.29 mmol, 1.70 equiv). The resulting solution was stirred for 12 h at reflux in an oil bath, then concentrated under vacuum. The residue was applied onto a silica gel column with ethyl acetate/petroleum ether (1:30-1:10). The resulting residue was diluted with hydrogen chloride/ethyl acetate (50 mL). After stirring 1 hour, the resulting mixture was concentrated under vacuum. The resulting residue was purified by re-crystallization from diethyl ether to yield 3-methyl-1-phenyl-6-(3-(piperazin-1-yl)phenyl)-1H-indazole hydrochloride as a yellow solid.

MS (m/z): 368 [M−HCl+H]$^+$; $^1$HNMR (400 MHz, DMSO, ppm): δ 2.59 (3H, s), 3.40-4.02 (8H, m), 7.08-7.88 (12H, m), 8.99 (2H, s).

Example 59

3-Methyl-1-phenyl-6-(piperazin-1-yl)-1H-indazole

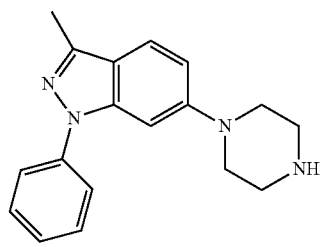 [SMILES: Cc1nn(-c2ccccc2)c2cc(N3CCNCC3)ccc12]

Into a 100-mL 3-necked round-bottom flask purged and maintained with an inert atmosphere of nitrogen, was placed a solution of 6-bromo-3-methyl-1-phenyl-1H-indazole (1 g, 3.50 mmol, 1.00 equiv) in toluene (20 mL), piperazine (600 mg, 6.98 mmol, 2.00 equiv), Cs$_2$CO$_3$ (1.7 g, 5.21 mmol, 1.50 equiv), Pd(AcO)$_2$ (20 mg, 0.09 mmol, 0.03 equiv), BINAP (20 mg, 0.03 mmol, 0.03 equiv). The resulting solution was stirred overnight at 100° C. in an oil bath. The resulting mixture was cooled, the solids were filtered out. The residue was applied onto a silica gel column with dichloromethane/methanol (20:1). The resulting residue (300 mg) was purified by Prep-HPLC with the following conditions (AGILENT Pre-HPLC (UV-Directed)): Column, SunFire Prep C18, 5 um, 19*100 mm; mobile phase, water with 0.05% TFA and MeOH (10% MeOH up to 42% in 4 min, hold 42% in 3.5 min, up to 100% in 0.1 min, hold 100% in 1.4 min); Detector, UV 220NMnm to yield 3-methyl-1-phenyl-6-(piperazin-1-yl)-1H-indazole as a light yellow solid.

MS (m/z): 293 [M+H]+; 1HNMR (300 MHz, CD3OD, ppm): δ 2.58 (3H, s), 3.32-3.50 (8H, m), 7.07-7.09 (2H, d), 7.37-7.42 (1H, t), 7.55-7.60 (2H, m), 7.66-7.72 (3H, m).

Example 60

3-Methyl-1-phenyl-6-(3-(piperazin-1-yl)azetidin-1-yl)-1H-indazole hydrochloride

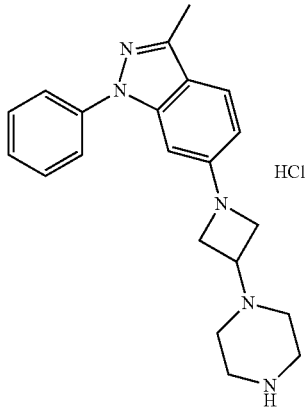 [SMILES: Cc1nn(-c2ccccc2)c2cc(N3CC(N4CCNCC4)C3)ccc12 ; Cl]

The title compound was prepared according to the procedure as described in Example 57 reacting 4-azetidin-3-yl-piperazine-1-carboxylic acid tert-butyl ester, followed by de-protection with HCl. hydrochloride.

MS (m/z): 348 [M−HCl+H]+; 1HNMR (400 MHz, D2O, ppm): δ 2.35 (3H, s), 2.66 (4H, s), 3.14-3.19 (4H, m), 3.40-3.42 (1H, m), 3.59-3.63 (2H, t), 3.92-3.96 (2H, t), 6.45-6.49 (2H, t), 7.32-7.55 (6H, m).

Example 61

3-Methyl-1-phenyl-6-(3-(piperazin-1-yl)pyrrolidin-1-yl)-1H-indazole hydrochloride

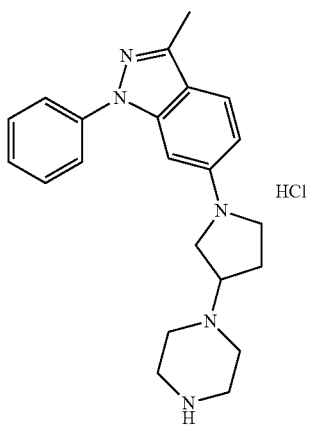 [SMILES: Cc1nn(-c2ccccc2)c2cc(N3CCC(N4CCNCC4)C3)ccc12 ; Cl]

The title compound was prepared according to the procedure as described in Example 57 reacting 4-pyrrolidin-3-yl-piperazine-1-carboxylic acid tert-butyl ester, followed by de-protection with HCl.

MS (m/z): 362 [M−HCl+H]+; 1HNMR (400 MHz, D2O, ppm) δ: 2.03-2.08 (1H, m), 2.38 (4H, s), 3.17-3.75 (13H, m), 6.59-6.61 (1H, d), 7.31-7.52 (6H, m).

Example 62

6-(4-(Azetidin-3-yl)piperazin-1-yl)-3-methyl-1-phenyl-1H-indazole hydrochloride

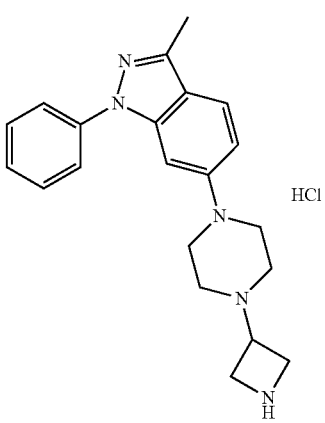 [SMILES: Cc1nn(-c2ccccc2)c2cc(N3CCN(C4CNC4)CC3)ccc12 ; Cl]

The title compound was prepared according to the procedure as described in Example 57 reacting 3-piperazin-1-yl-azetidine-1-carboxylic acid tert-butyl ester, followed by de-protection with HCl.

MS (m/z): 348 [M−HCl+H]+; 1HNMR (300 MHz, D2O, ppm): δ 2.48 (3H, s), 2.66 (4H, s), 3.18 (4H, m), 3.47 (4H, m), 4.24 (1H, m), 4.38 (4H, m), 7.04-7.74 (6H, m).

Example 63

3-Methyl-1-phenyl-6-(4-(pyrrolidin-3-yl)piperazin-1-yl)-1H-indazole hydrochloride

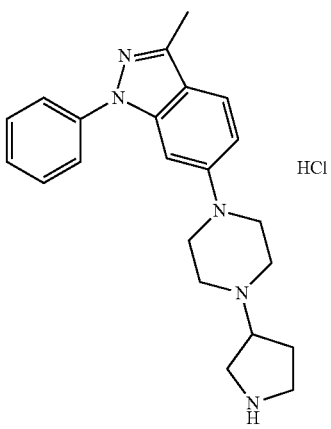 [SMILES: Cc1nn(-c2ccccc2)c2cc(N3CCN(C4CCNC4)CC3)ccc12 ; Cl]

The title compound was prepared according to the procedure as described in Example 57 reacting 3-piperazin-1-yl-pyrrolidine-1-carboxylic acid tert-butyl ester, followed by de-protection with HCl.

MS (m/z): 362 [M–HCl+H]⁺; ¹HNMR (400 MHz, DMSO, ppm): δ 3.23 (5H, m), 3.65 (4H, m), 4.0 (2H, m), 7.08-7.74 (8H, m).

Example 64

3-Methyl-1-phenyl-6-(4-(piperidin-4-yl)piperazin-1-yl)-1H-indazole hydrochloride

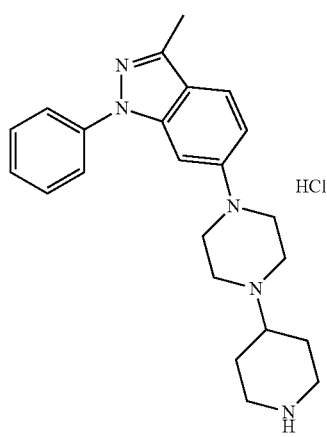 [SMILES: Cc1nn(-c2ccccc2)c2cc(N3CCN(C4CCNCC4)CC3)ccc12 ; Cl]

The title compound was prepared according to the procedure as described in Example 57 reacting 4-piperazin-1-yl-piperidine-1-carboxylic acid tert-butyl ester, followed by deprotection with HCl.

MS (m/z): 376 [M–HCl+H]⁺

¹HNMR (400 MHz, D₂O, ppm): δ 1.85 (2H, dd), 2.38 (2H, m), 2.41 (3H, s), 3.12 (4H, m), 3.69 (4H, m), 6.9-7.6 (8H, m).

Example 65

3-Methyl-1-phenyl-6-(4-(pyridin-4-yl)piperazin-1-yl)-1H-indazole hydrochloride

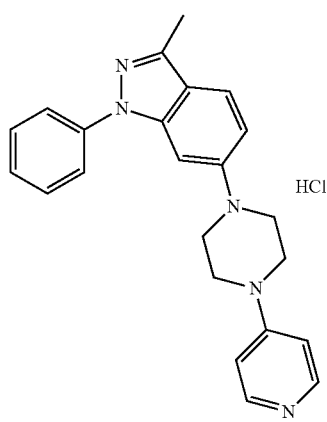 [SMILES: Cc1nn(-c2ccccc2)c2cc(N3CCN(c4ccncc4)CC3)ccc12 ; Cl]

The title compound was prepared according to the procedure as described in Example 57 reacting 1-pyridin-4-yl-piperazine as the building block and then by the treatment of the adduct with hydrochloride.

MS (m/z): 370 [M–HCl+H]⁺; ¹HNMR (400 MHz, DMSO, ppm): δ 3.45 (4H, s), 3.9 (4H, s), 7.06-8.28 (12H, m).

Example 66

N-(3-methyl-1-phenyl-1H-indazol-6-yl)-1H-benzo[d]imidazole-5-carboxamide

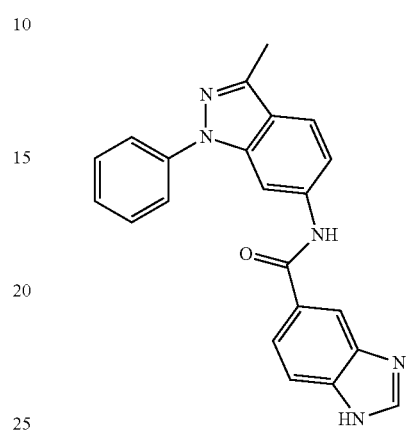

Step A: 3-Methyl-1-phenyl-1H-indazol-6-ylamine

Into a 100-mL 3-necked round-bottom flask purged and maintained with an inert atmosphere of nitrogen, was placed a solution of 6-bromo-3-methyl-1-phenyl-1H-indazole (1 g, 3.48 mmol, 1.00 equiv) in tetrahydrofuran (50 mL), Xantphos (222 mg, 0.38 mmol, 0.11 equiv), Pd(OAc)₂ (117 mg, 0.52 mmol, 0.15 equiv), Cs₂CO₃ (1.25 g, 6.48 mmol, 1.11 equiv), diphenylmethanimine (700 mg, 3.87 mmol, 1.10 equiv). The resulting solution was heated to reflux for 16 h in an oil bath, then concentrated under vacuum. The residue was dissolved in tetrahydrofuran/3N hydrogen chloride (50 mL/15 mL). The resulting solution was stirred for an additional 2 h at room temperature, then concentrated under vacuum. The residue was applied onto a silica gel column with ethyl acetate: MeOH:NH₄OH (30:1:0.3). The residue was dissolved in HCl/EtOAc (2M, 30 mL). The resulting mixture was concentrated under vacuum and washed with Et₂O. The solids were collected by filtration to yield 3-methyl-1-phenyl-1H-indazol-6-amine hydrochloride as a yellow solid.

MS (m/z): 224 [M–HCl+H]⁺; ¹HNMR (400 MHz, DMSO, ppm): δ 2.577 (3H, s), 7.105-7.130 (1H, m), 4.379-4.416 (1H, m), 7.465-7.497 (1H, m), 7.578-7.617 (2H, m), 7.688-7.712 (3H, m), 7.861-7.882 (1H, d).

Step B: N-(3-methyl-1-phenyl-1H-indazol-6-yl)-1H-benzo[d]imidazole-5-carboxamide Into a 100-mL 3-necked round-bottom flask, was placed a solution of 3-methyl-1-phenyl-1H-indazol-6-amine (520 mg, 2.33 mmol, 1.00 equiv) in N,N-dimethylformamide (50 mL), 1H-benzo[d]imidazole-5-carboxylic acid (324 mg, 2.00 mmol, 0.86 equiv), NBu₃ (925 mg, 5.00 mmol, 2.14 equiv). To the resulting mixture was then added 2-chloro-1-methylpyridiniumiodide (612 mg, 2.40 mmol, 1.03 equiv) at 50° C. The resulting solution was stirred for 2 days at 100° C. in an oil bath, then concentrated under vacuum. The residue was applied onto a silica gel column with dichloromethane/methanol (50:1). The resulting mixture was washed with methanol (1×10 mL) and diethyl ether (1×10 mL) to yield N-(3-methyl-1-phenyl-1H-indazol-6-yl)-1H-benzo[d]imidazole-5-carboxamide as a yellow solid.

MS (m/z): 367 [M+H]$^+$; $^1$HNMR (400 MHz, DMSO, ppm): δ 2.50 (3H, s), 7.37-8.52 (10H, m), 9.44 (1H, s), 10.72 (1H, s).

Example 67

1-(3-Methyl-1-phenyl-1H-indazol-6-yl)-3-(piperidin-4-yl)imidazolidin-2-one hydrochloride

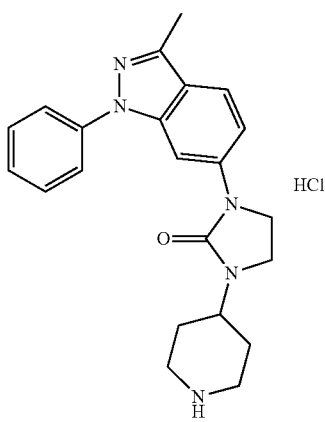 [SMILES: Cc1nn(-c2ccccc2)c2cc(N3CCN(C4CCNCC4)C3=O)ccc12 ; Cl]

The title compound was prepared according to the procedure as described in Example 57 reacting 4-(2-oxo-imidazolidin-1-yl)-piperidine-1-carboxylic acid tert-butyl ester, followed by de-protection with HCl.

MS (m/z): 376 [M−HCl+H]$^+$; $^1$HNMR (400 MHz, DMSO, ppm): δ 1.88 (4H, m), 2.54 (3H, s), 3.03 (2H, d), 3.34-3.54 (5H, m), 3.96 (3H, m), 7.33-8.67 (10H, m).

Example 68

3-Methyl-6-(4-methylpiperazin-1-yl)-1-phenyl-1H-indazole

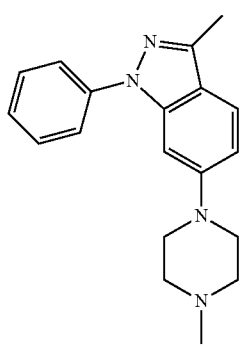 [SMILES: Cc1nn(-c2ccccc2)c2cc(N3CCN(C)CC3)ccc12]

The title compound was prepared according to the procedure as described in Example 57 reacting 1-methyl-piperazine.

MS (m/z): 307 [M+H]$^+$; $^1$HNMR (300 MHz, CDCl$_3$, ppm): δ 2.62 (3H, s), 2.90 (3H, s), 3.06 (2H, s), 3.44 (2H, s), 3.69-3.73 (4H, d), 6.89-6.92 (1H, d), 7.07 (1H, d), 7.34-7.39 (1H, m), 7.52-7.67 (5H, m).

Example 69

6-(4-Ethylpiperazin-1-yl)-3-methyl-1-phenyl-1H-indazole 2,2,2-trifluoroacetic acid salt

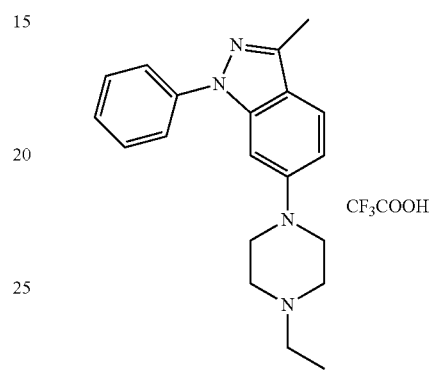

The title compound was prepared according to the procedure as described in Example 57 reacting 1-ethyl-piperazine.

MS (m/z): 321[M−CF$_3$COOH+H]$^+$; $^1$HNMR (300 MHz, CD$_3$OD, ppm): δ 1.39-1.44 (3H, t), 2.59 (3H, s), 3.12-3.16 (2H, m), 3.68-3.72 (2H, m), 3.96-4.00 (2H, m), 7.08-7.11 (2H, m), 7.38-7.43 (1H, m), 7.55-7.61 (2H, m), 7.69-7.73 (3H, m).

Example 70

6-(4-Isopropylpiperazin-1-yl)-3-methyl-1-phenyl-1H-indazole formic acid salt

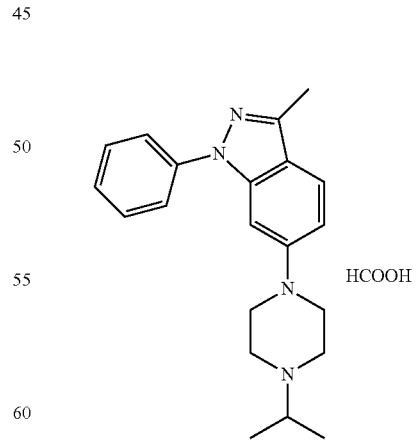

The title compound was prepared according to the procedure as described in Example 57 reacting 1-iso-propyl-piperazine.

MS (m/z): 335 [M−HCOOH+H]$^+$

¹HNMR (300 MHz, CD₃OD, ppm): 1.34-1.36 (6H, m), 2.58 (3H, s), 3.25-3.32 (4H, m), 3.46-3.48 (4H, m), 7.06-7.10 (2H, t), 7.37-7.42 (1H, m), 7.55-7.70 (5H, m).

Example 71

3-Methyl-6-(3-methylpiperazin-1-yl)-1-phenyl-1H-indazole formic acid salt

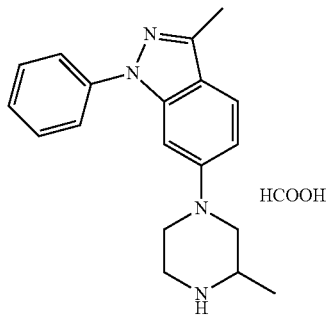 [SMILES: Cc1nn(-c2ccccc2)c2cc(N3CCNC(C)C3)ccc12 ; "HCOOH"]

The title compound was prepared according to the procedure as described in Example 57 reacting 2-methyl-piperazine-1-carboxylic acid tert-butyl ester, followed by de-protection with HCl.

MS (m/z): 307 [M−HCOOH+H]$^+$; ¹HNMR (300 MHz, CD₃OD, ppm): 1.39-1.41 (3H, d), 2.58-2.59 (3H, d), 2.81-2.88 (1H, t), 3.04-3.12 (1H, t), 3.28 (1H, s), 3.48-3.52 (2H, d), 3.81-3.90 (2H, t), 7.07-7.10 (2H, m), 7.37-7.42 (1H, m), 7.56-7.71 (5H, m), 8.50 (1H, s).

Example 72

1-(3-Methyl-1-phenyl-1H-indazol-6-yl)pyrrolidin-3-amine formic acid salt

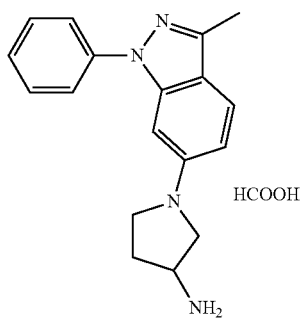 [SMILES: Cc1nn(-c2ccccc2)c2cc(N3CCC(N)C3)ccc12 ; "HCOOH"]

The title compound was prepared according to the procedure as described in Example 57 reacting pyrrolidin-3-yl-carbamic acid tert-butyl ester, followed by de-protection with HCl.

MS (m/z): 293 [M−HCOOH+H]$^+$; ¹HNMR (300 MHz, CD₃OD, ppm): 2.14-2.22 (1H, m), 2.44-2.51 (1H, m), 2.55 (3H, s), 3.44-3.55 (2H, m), 3.63-3.72 (2H, m), 4.03-4.04 (1H, s), 6.66-6.67 (1H, d), 6.75-6.78 (1H, m), 7.34-7.39 (1H, m), 7.53-7.68 (5H, m), 8.52 (1H, s).

Example 73

3-Methoxy-1-phenyl-6-(3-(piperazin-1-yl)azetidin-1-yl)-1H-indazole hydrochloride

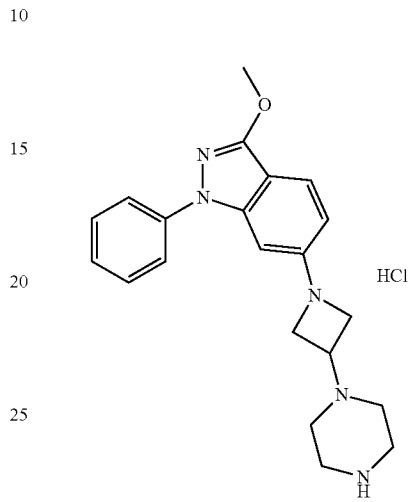

Step A: 6-Bromo-3-methoxy-1-phenyl-1H-indazole

Into a 100-mL 3-necked round-bottom flask purged and maintained with an inert atmosphere of nitrogen, was placed a solution of 6-bromo-1-phenyl-1,2-dihydroindazol-3-one (5 g, 17.30 mmol, 1.00 equiv) in N,N-dimethylformamide (50 mL), potassium carbonate (3.7 g, 34.91 mmol, 2.00 equiv), CH₃I (2.7 g, 19.01 mmol, 1.10 equiv). The resulting solution was stirred for 3 h at 80° C. in an oil bath. The reaction was then quenched by the addition of water (100 mL). The resulting solution was extracted with ethyl acetate (3×150 mL) and the organic layers combined, dried over anhydrous sodium sulfate and concentrated under vacuum. The residue was applied onto a silica gel column with ethyl acetate/petroleum ether (1:40) to yield 6-bromo-3-methoxy-1-phenyl-1H-indazole as a yellow solid.

MS (m/z): 303 [M+H]$^+$; ¹HNMR (400 MHz, CDCl₃, ppm): δ 4.168-4.183 (3H, d), 7.251-7.682 (7H, m), 7.837-7.839 (1H, d).

Step B: 3-Methoxy-1-phenyl-6-(3-(piperazin-1-yl) azetidin-1-yl)-1H-indazole hydrochloride The title compound was prepared according to the procedure as described in Example 57 reacting 6-bromo-3-methoxy-1-phenyl-1H-indazole and 4-azetidin-3-yl-piperazine-1-carboxylic acid tert-butyl ester, followed by de-protection with HCl.

MS (m/z): 364 [M−HCl+H]$^+$; ¹HNMR (400 MHz, DMSO, ppm): δ 2.78 (4H, s), 3.20 (4H, s), 3.80 (3H, m), 4.03 (3H, s), 4.08 (2H, s), 6.40-6.42 (1H, d), 6.52 (2H, s), 7.24-7.68 (6H, m).

Example 74

6-(4-(Azetidin-3-yl)piperazin-1-yl)-3-methoxy-1-phenyl-1H-indazole hydrochloride

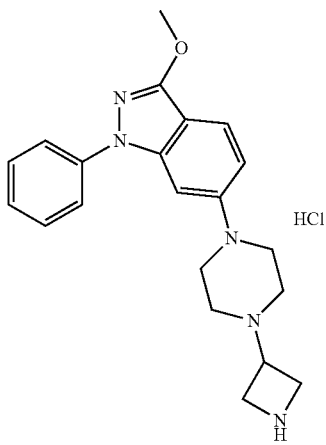 [SMILES: COc1nn(-c2ccccc2)c2cc(N3CCN(C4CNC4)CC3)ccc12 ; Cl]

The title compound was prepared according to the procedure as described in Example 57 reacting 6-bromo-3-methoxy-1-phenyl-1H-indazole and 3-piperazin-1-yl-azetidine-1-carboxylic acid tert-butyl ester, followed by de-protection with HCl.

MS (m/z): 364 [M−HCl+H]$^+$; $^1$HNMR (300 MHz, D$_2$O, ppm): δ 3.18 (4H, s), 3.40 (4H, s), 3.96 (3H, s), 4.25-4.27 (1H, m), 4.37-4.39 (4H, d), 6.83-6.88 (2H, m), 7.32-7.35 (1H, m), 7.41-7.50 (5H, m).

Example 75

3-Methoxy-1-phenyl-6-(4-(pyrrolidin-3-yl)piperazin-1-yl)-1H-indazole hydrochloride

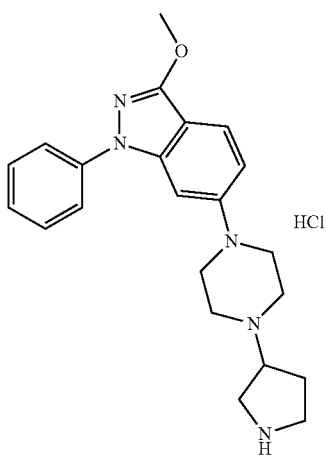 [SMILES: COc1nn(-c2ccccc2)c2cc(N3CCN(C4CCNC4)CC3)ccc12 ; Cl]

The title compound was prepared according to the procedure as described in Example 57 reacting 6-bromo-3-methoxy-1-phenyl-1H-indazole and 3-piperazin-1-yl-pyrrolidine-1-carboxylic acid tert-butyl ester, followed by de-protection with HCl.

MS (m/z): 378 [M−HCl+H]$^+$; $^1$HNMR (400 MHz, D$_2$O, ppm): δ 2.11-2.16 (1H, t), 2.54 (1H, s), 3.33-3.40 (10H, m), 3.51-3.56 (1H, m), 4.37-4.39 (4H, d), 6.83-6.88 (2H, m), 7.32-7.35 (1H, m), 7.41-7.50 (5H, m).

Example 76

3-Methoxy-1-phenyl-6-(4-(piperidin-4-yl)piperazin-1-yl)-1H-indazole hydrochloride

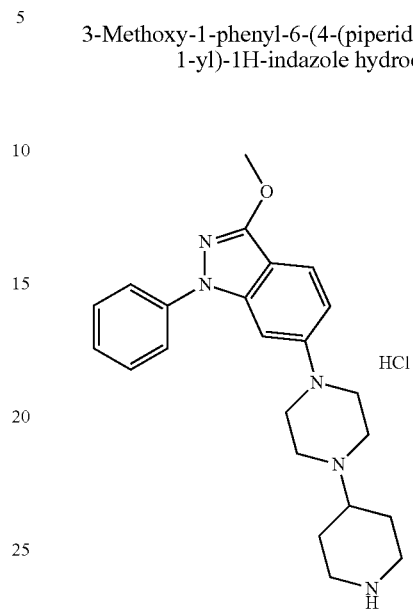

The title compound was prepared according to the procedure as described in Example 57 reacting 6-bromo-3-methoxy-1-phenyl-1H-indazole and 4-piperazin-1-yl-piperidine-1-carboxylic acid tert-butyl ester, followed by de-protection with HCl.

MS (m/z): 392 [M−HCl+H]$^+$; $^1$HNMR (400 MHz, D$_2$O, ppm): δ 1.85-1.87 (2H, m), 2.34-2.37 (2H, m), 2.97-3.03 (2H, m), 3.16-3.98 (11H, m), 3.98 (3H, s), 6.86-6.91 (2H, m), 7.30-7.58 (6H, m).

Example 77

3-Methoxy-1-phenyl-6-(4-(pyridin-4-yl)piperazin-1-yl)-1H-indazole hydrochloride

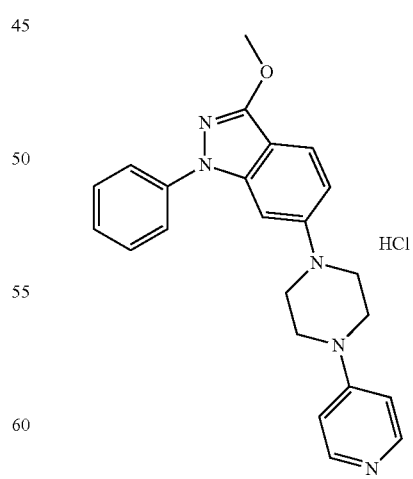

The title compound was prepared according to the procedure as described in Example 57 reacting 6-bromo-3-methoxy-1-phenyl-1H-indazole and 1-pyridin-4-yl-piperazine, followed by de-protection with HCl.

MS (m/z): 386 [M−HCl+H]+; 1HNMR (400 MHz, DMSO, ppm): δ 3.46 (4H, s), 3.88 (4H, s), 4.04 (3H, s), 6.99-7.02 (2H, d), 7.23-7.27 (3H, t), 7.50-7.56 (3H, dd), 7.70-7.72 (2H, d), 8.27 (2H, s).

Example 78

3-Methoxy-1-phenyl-6-(4-(piperazin-1-yl)phenyl)-1H-indazole hydrochloride

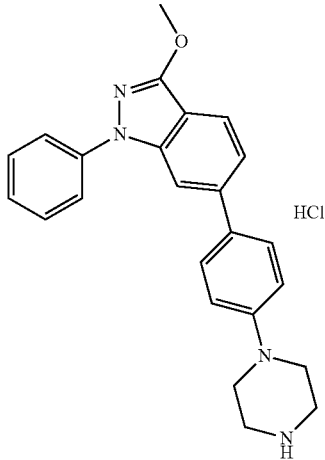 [SMILES: COc1nn(-c2ccccc2)c2cc(-c3ccc(N4CCNCC4)cc3)ccc12 ; Cl]

The title compound was prepared according to the procedure as described in Example 58 reacting 6-bromo-3-methoxy-1-phenyl-1H-indazole and 4-[4-(4,4,5,5-tetramethyl-[1,3,2]dioxaborolan-2-yl)-phenyl]-piperidine-1-carboxylic acid tert-butyl ester, followed by de-protection with HCl.

MS (m/z): 385 [M−HCl+H]+; 1HNMR (400 MHz, DMSO, ppm): δ 3.24 (4H, s), 3.44 (4H, s), 4.11 (3H, s), 7.09-7.11 (2H, d), 7.30-7.33 (1H, t), 7.44-7.83 (9H, m), 9.04-9.07 (2H, br, s).

Example 79

6-(4-(1H-Imidazol-1-yl)phenyl)-3-methoxy-1-phenyl-1H-indazole

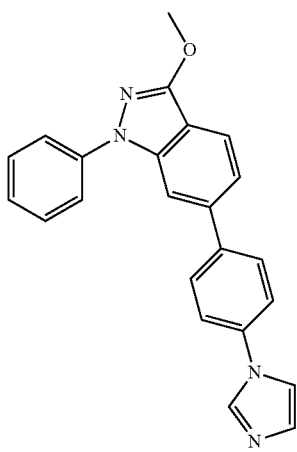 [SMILES: COc1nn(-c2ccccc2)c2cc(-c3ccc(-n4ccnc4)cc3)ccc12]

The title compound was prepared according to the procedure as described in Example 58 reacting 6-bromo-3-methoxy-1-phenyl-1H-indazole and 1-[4-(4,4,5,5-tetramethyl-[1,3,2]dioxaborolan-2-yl)-phenyl]-1H-imidazole as the building block.

MS (m/z): 367 [M+H]+; 1HNMR (400 MHz, DMSO, ppm): δ 4.20 (3H, s), 7.29-7.34 (2H, m), 7.39 (2H, s), 7.53 (4H, s), 7.72-7.82 (6H, t), 8.22 (1H, s).

Example 80

N-(3-methoxy-1-phenyl-1H-indazol-6-yl)-1H-benzo[d]imidazole-5-carboxamide

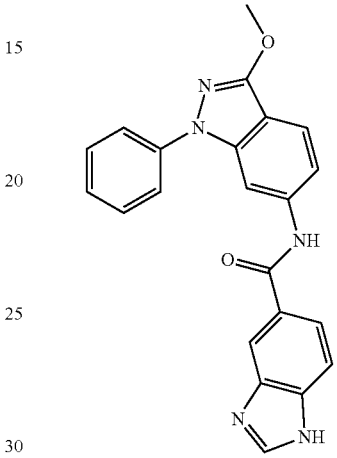

Step A: 3-Methoxy-6-nitro-1-phenyl-1H-indazole

Into a 100-mL 3-necked round-bottom flask purged and maintained with an inert atmosphere of nitrogen, was placed a solution of 6-nitro-1-phenyl-1,2-dihydroindazol-3-one (2 g, 7.69 mmol, 1.00 equiv, 98%) in toluene (50 mL), CH3I (4.3 g, 29.68 mmol, 3.86 equiv, 98%), potassium carbonate (1.63 g, 11.58 mmol, 1.51 equiv, 98%), N,N-dimethylformamide (50 mL). The resulting solution was stirred for 1 h at 80° C. in an oil bath. The resulting solution was diluted with water (100 mL). The resulting solution was extracted with dichloromethane (2×50 mL) and the organic layers were combined, then concentrated under vacuum. The residue was applied onto a silica gel column with ethyl acetate/petroleum ether (1:100). The collected fractions were combined and concentrated under vacuum to yield 3-methoxy-6-nitro-1-phenyl-1H-indazole as a yellow solid.

Step B: 3-Methoxy-1-phenyl-1H-indazol-6-ylamine

A 250-mL 3-necked round-bottom flask was purged, was added a solution of 3-methoxy-6-nitro-1-phenyl-1H-indazole (800 mg, 2.91 mmol, 1.00 equiv, 98%) in tetrahydrofuran (125 mL), palladium carbon (0.1 g), then flushed and maintained with a hydrogen atmosphere. The resulting solution was stirred for 5 min at room temperature. The solids were filtered out. The resulting mixture was concentrated under vacuum to yield 3-methoxy-1-phenyl-1H-indazol-6-amine as a gray solid. MS (m/z): 240 [MH+].

Step C: N-(3-methoxy-1-phenyl-1H-indazol-6-yl)-1H-benzo[d]imidazole-5-carboxamide The title compound was prepared according to the procedure as described in Example 66 reacting 3-methoxy-1-phenyl-1H-indazol-6-ylamine and 1H-Benzoimidazole-5-carboxylic acid.

MS (m/z): 384 [M+H]+; 1HNMR (300 MHz, DMSO, ppm): δ 4.10 (3H, s), 7.32-7.37 (1H, t), 7.57-7.63 (3H, m), 7.71-7.74 (3H, d), 7.92-7.95 (1H, d), 8.11-8.13 (1H, d), 8.45 (1H, s), 8.52 (1H, s), 9.39 (1H, s), 10.73 (1H, s).

Example 81

1-(3-Methoxy-1-phenyl-1H-indazol-6-yl)-3-(piperidin-4-yl)imidazolidin-2-one hydrochloride

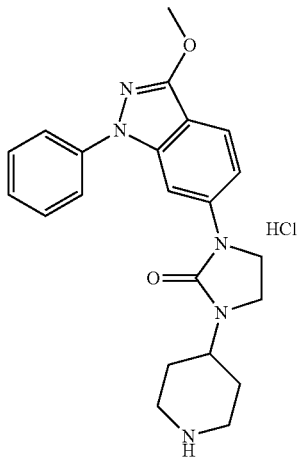 [SMILES: COc1nn(-c2ccccc2)c2cc(N3CCN(C4CCNCC4)C3=O)ccc12 ; Cl]

The title compound was prepared according to the procedure as described in Example 57 reacting 6-bromo-3-methoxy-1-phenyl-1H-indazole and 4-(2-oxo-imidazolidin-1-yl)-piperidine-1-carboxylic acid tert-butyl ester, followed by de-protection with HCl.

MS (m/z): 392 [M−HCl+H]+; 1HNMR (400 MHz, D2O, ppm): δ 2.08-2.10 (4H, t), 3.28-3.35 (2H, m), 3.49-3.51 (2H, d), 3.57-3.59 (2H, d), 3.71-3.75 (2H, d), 4.04-4.18 (1H, m), 4.18 (3H, s), 7.05-7.67 (8H, m).

Example 82

6-(4-Azetidin-3-yl-piperazin-1-yl)-3-ethyl-1-phenyl-1H-pyrazolo[3,4-d]pyrimidine

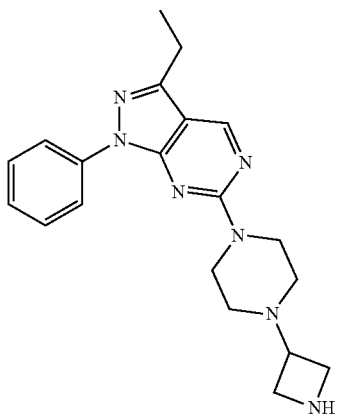 [SMILES: CCc1nn(-c2ccccc2)c2nc(N3CCN(C4CNC4)CC3)ncc12]

Step A: 2-(1-Ethoxy-ethylidene)-malononitrile

Into a 250-mL 3-necked round-bottom flask, was placed malononitrile (20.4 g, 309.09 mmol, 1.00 equiv) at room temperature. To the resulting mixture was then added 1,1,1-triethoxyethane (50 g, 308.64 mmol, 1.00 equiv), in portions at room temperature. To the resulting mixture was then added acetic anhydride (72 g, 705.88 mmol, 2.28 equiv), in portions at room temperature. The resulting solution was heated to reflux for 3 hr. The resulting mixture was concentrated under vacuum, then cooled with a water/ice bath. The solids were collected by filtration to yield 2-(1-ethoxyethylidene)malononitrile as a white solid.

Step B: 5-Amino-3-methyl-1-phenyl-1H-pyrazole-4-carbonitrile

Into a 250-mL 3-necked round-bottom flask, was placed a solution of 1-phenylhydrazine (31.5 g, 291.67 mmol, 1.14 equiv) in ethanol (105 mL) at room temperature. To the resulting mixture was then added 2-(1-ethoxyethylidene)malononitrile (35 g, 257.35 mmol, 1.00 equiv) in several batches at room temperature. After about half of the addition was completed, the solution was carefully heated to boiling. After all the ethoxymethylene malononitrile was added, the resulting solution was heated to reflux for 4 hr. The resulting mixture was then cooled with a water/ice bath, and the solids were collected by filtration to yield 5-amino-3-methyl-1-phenyl-1H-pyrazole-4-carbonitrile as a yellow solid.

Step C: 5-Amino-3-methyl-1-phenyl-1H-pyrazole-4-carboxylic acid amide

Into a 100-mL 3-necked round-bottom flask, was placed sulfuric acid (90 mL). To the resulting mixture was then added 5-amino-3-methyl-1-phenyl-1H-pyrazole-4-carbonitrile (30 g, 151.52 mmol, 1.00 equiv), in portions at 10° C. The resulting solution was stirred overnight at room temperature. The reaction was then quenched by the addition of water/ice (100 mL). The pH value of the solution was adjusted to about 8-9 with potassium carbonate (conc.). The solids were collected by filtration, to yield 5-amino-3-methyl-1-phenyl-1H-pyrazole-4-carboxamide as a white solid.

Step D: 3-Ethyl-1-phenyl-1,7-dihydro-pyrazolo[3,4-d]pyrimidine-4,6-dione

Into a 100-mL 3-necked round-bottom flask, was placed 5-amino-3-ethyl-1-phenyl-1H-pyrazole-4-carboxamide (1 g, 4.35 mmol, 1.00 equiv) at room temperature. To the resulting mixture was then added urea (1.75 g, 29.17 mmol, 6.70 equiv), in portions at room temperature. The resulting solution was stirred for 1 h at 200° C. The resulting mixture was then cooled to room temperature. The residue was dissolved in sodium hydroxide (250 mL). The pH value of the solution was adjusted to about 5 with AcOH (conc.). The solids were collected by filtration to yield 3-ethyl-1-phenyl-1H-pyrazolo[3,4-d]pyrimidine-4,6(5H,7H)-dione as a white solid. MS (m/z): 257 [MH+].

Step E: 4,6-Dichloro-3-ethyl-1-phenyl-1H-pyrazolo[3,4-d]pyrimidine

Into a 100-mL 3-necked round-bottom flask, was placed 3-ethyl-1-phenyl-1H-pyrazolo[3,4-d]pyrimidine-4,6(5H,7H)-dione (500 mg, 1.95 mmol, 1.00 equiv) at room temperature. To the resulting mixture was then added PCl$_5$ (1.8 g, 8.75 mmol, 4.45 equiv), in portions at room temperature. To the resulting mixture was added POCl$_3$ (5 mL), in portions at room temperature. The resulting solution was heated to reflux for 3 hr. The reaction was then quenched by the addition of water/ice (100 mL). The resulting solution was extracted with chloroform (3×100 mL), the organic layers combined and dried over anhydrous sodium sulfate. The solids were filtered out. The resulting mixture was then concentrated under vacuum to yield 4,6-dichloro-3-ethyl-1-phenyl-1H-pyrazolo [3,4-d]pyrimidine as a yellow solid. MS (m/z): 293 [MH$^+$].

Step F: 6-Chloro-3-ethyl-1-phenyl-1H-pyrazolo[3,4-d]pyrimidine

Into a 100-mL 3-necked round-bottom flask, was placed a solution of 4,6-dichloro-3-ethyl-1-phenyl-1H-pyrazolo[3,4-d]pyrimidine (300 mg, 1.03 mmol, 1.00 equiv) in dichloromethane (10 mL) at room temperature. To the resulting mixture was then added Zn (400 mg, 6.15 mmol, 6.00 equiv), in portions at room temperature, followed by NH$_3$/NaCl (10 mL), in portions at room temperature. The resulting solution was stirred overnight at 60° C. The solids were filtered out. The resulting solution was extracted with dichloromethane (2×50 mL) and the organic layers combined. The resulting mixture was washed with sodium chloride (3×50 mL). The resulting mixture was dried over anhydrous sodium sulfate and the solids were filtered out. The resulting mixture was concentrated under vacuum to yield 6-chloro-3-ethyl-1-phenyl-1H-pyrazolo[3,4-d]pyrimidine as a yellow solid. MS (m/z): 258 [MH$^+$].

Step G: 6-[4-(1-Benzhydryl-azetidin-3-yl)-piperazin-1-yl]-3-ethyl-1-phenyl-1H-pyrazolo[3,4-d]pyrimidine Into a 100-mL 3-necked round-bottom flask, was placed a solution of 6-chloro-3-ethyl-1-phenyl-1H-pyrazolo[3,4-d] pyrimidine (420 mg, 1.63 mmol, 1.00 equiv) in C$_7$H$_8$ (15 mL) at room temperature. To the resulting mixture was then added 1-(1-benzhydrylazetidin-3-yl)piperazine (500 mg, 1.63 mmol, 1.00 equiv), in portions at room temperature, followed by triethylamine (490 mg, 4.85 mmol, 3.00 equiv), in portions at room temperature. The resulting solution was heated to reflux overnight. The resulting mixture was concentrated under vacuum. The residue was dissolved in DCM (20 mL). The resulting mixture was washed with sodium chloride (2×15 mL). The resulting mixture was concentrated under vacuum. The resulting mixture was washed with methanol (1×5 mL). The solids were collected by filtration to yield 6-(4-(1-benzhydrylazetidin-3-yl)piperazin-1-yl)-3-ethyl-1-phenyl-1H-pyrazolo[3,4-d]pyrimidine as a yellow solid. MS (m/z): 530 [MH$^+$].

Step H: 6-(4-Azetidin-3-yl-piperazin-1-yl)-3-ethyl-1-phenyl-1H-pyrazolo[3,4-d]pyrimidine A 100-mL round-bottom flask was purged, flushed and maintained with a hydrogen atmosphere, then, was added a solution of 6-(4-(1-benzhydrylazetidin-3-yl)piperazin-1-yl)-3-ethyl-1-phenyl-1H-pyrazolo[3,4-d]pyrimidine (400 mg, 0.76 mmol, 1.00 equiv) in acetic acid (20 mL) at room temperature. To the resulting mixture was then added Pd(OH)$_2$ (50 mg, 0.4 mmol, 0.5 equiv), in portions at room temperature, followed by PdCl$_2$ (50 mg, 0.28 mmol, 0.37 equiv), in portions at room temperature. The resulting solution was stirred overnight at room temperature. The solids were filtered out. The resulting mixture was concentrated under vacuum. The resulting residue (250 mg) was purified by Prep-HPLC with the following conditions (Gilson Pre-HPLC): Column, SHISEIDO, CAPCELL PAK C18, 20 mm ID*250 mm, 5 u; mobile phase, methanol/H$_2$O; Detector, UV 254 nm, to yield 6-(4-(azetidin-3-yl)piperazin-1-yl)-3-ethyl-1-phenyl-1H-pyrazolo[3,4-d]pyrimidine as a white solid.

MS (m/z): 364 [M+H]$^+$; 1HNMR (400 MHz, DMSO, ppm): δ 1.33-1.37 (3H, t), 2.49-2.50 (2H, m), 2.70 (2H, m), 2.91-2.97 (2H, m), 3.58 (1H, m), 3.96 (3H, m), 4.03-4.04 (4H, m), 7.26-7.30 (1H, m), 7.50-7.54 (2H, m), 8.17-8.19 (2H, m), 8.81 (1H, s), 9.06 (1H, s).

Example 83

3-Ethyl-1-phenyl-6-(4-(pyridin-3-yl)piperazin-1-yl)-1H-pyrazolo[3,4-d]pyrimidine trifluoroacetic acid

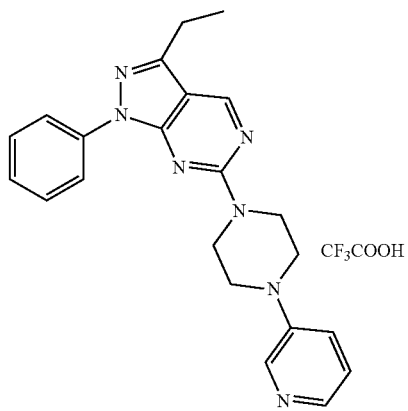 [SMILES: CCc1nn(-c2ccccc2)c2nc(N3CCN(c4cccnc4)CC3)ncc12 ; "CF3COOH"]

The title compound was prepared according to the procedure as described in Example 82 reacting 6-chloro-3-ethyl-1-phenyl-1H-pyrazolo[3,4-d]pyrimidine and 1-pyridin-3-yl-piperazine.

MS (m/z): 386 [M−CF$_3$COOH+H]$^+$; 1HNMR (400 MHz, DMSO, ppm): δ 1.33-1.37 (3H, t), 2.91-2.97 (2H, m), 3.57-3.58 (4H, m), 4.05 (4H, m), 7.27-7.30 (1H, m), 7.51-7.55 (2H, m), 7.80-7.83 (1H, m), 8.06-8.08 (1H, m), 8.19-8.21 (3H, m), 8.48 (1H, s), 9.07 (1H, s).

Example 84

3-Methyl-1-phenyl-6-(3,4,5,6-tetrahydro-2H-[1,3'] bipyridinyl-4-yl)-1H-pyrazolo[3,4-d]pyrimidin-4-ol

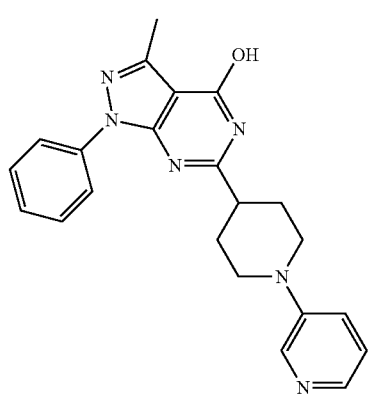 [SMILES: Cc1nn(-c2ccccc2)c2nc(C3CCN(c4cccnc4)CC3)nc(O)c12]

Into a 100-mL 3-necked round-bottom flask, was placed a solution of Na (64 mg, 2.78 mmol, 6.00 equiv) in ethanol (5 mL) at room temperature. To the resulting mixture was then added a solution of 5-amino-3-methyl-1-phenyl-1H-pyrazole-4-carboxamide (100 mg, 0.46 mmol, 1.00 equiv) in $C_4H_{10}O$ (10 mL), in portions at room temperature, followed by a solution of ethyl 1-(pyridin-3-yl)piperidine-4-carboxylate (650 mg, 2.78 mmol, 6.00 equiv) in $C_4H_{10}O$ (20 mL), in portions at room temperature. The resulting solution was heated to reflux for 5 hr. The reaction was then quenched by the addition of water (10 mL). The resulting solution was extracted with DCM (3×30 mL) and the organic layers combined. The resulting mixture was washed with sodium chloride (2×50 mL), then dried over anhydrous sodium sulfate. The solids were filtered out. The resulting mixture was concentrated under vacuum. The residue was applied onto a silica gel column with dichloromethane/methanol (50:1) to yield 3-methyl-1-phenyl-6-(1-(pyridin-3-yl)piperidin-4-yl)-1H-pyrazolo[3,4-d]pyrimidin-4(5H)-one as a white solid.

MS (m/z): 387 [M+H]$^+$; $^1$HNMR (400 MHz, DMSO, ppm): δ 1.88-1.95 (2H, m), 2.01-2.03 (2H, m), 2.49 (3H, s), 2.74-2.88 (3H, m), 3.85-3.88 (2H, m), 7.20-7.22 (1H, m), 7.30-7.37 (2H, m), 7.49-7.53 (2H, m), 7.97-7.98 (1H, m), 80.5-8.07 (2H, m), 8.33 (1H, m), 12.27 (1H, s).

Example 85

6-(1-Azetidin-3-yl-piperidin-3-yl)-3-methyl-1-phenyl-1H-pyrazolo[3,4-d]pyrimidin-4-ol

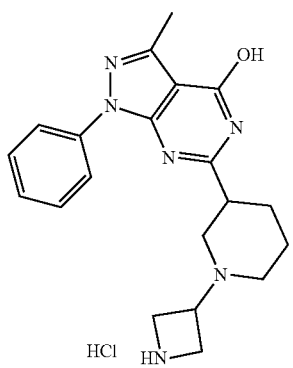 [SMILES: Cc1nn(-c2ccccc2)c2nc(C3CCCN(C4CNC4)C3)nc(O)c12 ; Cl]

Step A: 3-[3-(4-Hydroxy-3-methyl-1-phenyl-1H-pyrazolo[3,4-d]pyrimidin-6-yl)-piperidin-1-yl]-azetidine-1-carboxylic acid tert-butyl ester Into a 100-mL 3-necked round-bottom flask, was placed a solution of Na (128 mg, 5.57 mmol, 6.00 equiv) in ethanol (10 mL) at room temperature. To the resulting mixture was then added a solution of 5-amino-3-methyl-1-phenyl-1H-pyrazole-4-carboxamide (200 mg, 0.93 mmol, 1.00 equiv) in $C_4H_{10}O$ (10 mL), in portions at room temperature, followed by a solution of methyl 1-(1-(tert-butoxycarbonyl)azetidin-3-yl)piperidine-3-carboxylate (1.66 g, 5.57 mmol, 6.00 equiv) in $C_4H_{10}O$ (20 mL), in portions at room temperature. The resulting solution was heated to reflux overnight. The reaction was then quenched by the addition of water (20 mL). The resulting solution was extracted with DCM (3×30 mL) and the organic layers combined. The resulting mixture was washed with sodium chloride (2×30 mL). The mixture was dried over anhydrous sodium sulfate, the solids were filtered out. The resulting mixture was concentrated under vacuum. The residue was applied onto a silica gel column with dichloromethane/methanol (50:1) to yield tert-butyl 3-(3-(3-methyl-4-oxo-1-phenyl-4,5-dihydro-1H-pyrazolo[3,4-d]pyrimidin-6-yl)piperidin-1-yl)azetidine-1-carboxylate as a yellow solid.

Step B: 6-(1-Azetidin-3-yl-piperidin-3-yl)-3-methyl-1-phenyl-1H-pyrazolo[3,4-d]pyrimidin-4-ol Into a 100-mL round-bottom flask, was placed a solution of tert-butyl 3-(3-(3-methyl-4-oxo-1-phenyl-4,5-dihydro-1H-pyrazolo[3,4-d]pyrimidin-6-yl)piperidin-1-yl)azetidine-1-carboxylate (200 mg, 0.43 mmol, 1.00 equiv) in hydrogen chloride (5 mL) at room temperature. The resulting solution was heated to reflux overnight. The resulting mixture was concentrated under vacuum. The resulting residue (150 mg) was purified by Prep-HPLC with the following conditions (Gilson Pre-HPLC): Column, SHISEIDO, CAPCELL PAK C18, 20 mm ID*250 mm, 5 u; mobile phase, methanol/$H_2O$; Detector, UV 254 nm to yield 6-(1-(azetidin-3-yl)piperidin-3-yl)-3-methyl-1-phenyl-1H-pyrazolo[3,4-d]pyrimidin-4(5H)-one hydrochloride as a white solid.

MS (m/z): 365 [M−HCl+H]$^+$; $^1$HNMR (400 MHz, $D_2O$, ppm): δ 1.76-1.85 (2H, m), 1.96 (1H, m), 2.13-2.16 (1H, m), 2.45 (3H, s), 2.89 (1H, m), 3.22 (1H, m), 3.32 (1H, m), 3.49-3.79 (1H, m), 4.35 (5H, m), 7.40-7.44 (1H, m), 7.49-7.53 (2H, m), 7.65-7.67 (2H, m).

Example 86

3-Methyl-1-phenyl-6-piperidin-4-yl-1H-pyrazolo[3,4-d]pyrimidin-4-ol hydrochloride

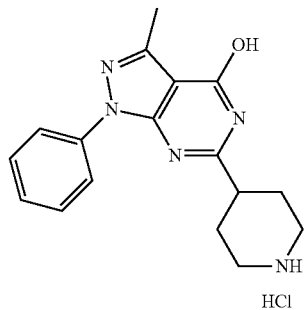 [SMILES: Cc1nn(-c2ccccc2)c2nc(C3CCNCC3)nc(O)c12 ; Cl]

The title compound was prepared according to the procedure as described in Example 84 reacting piperazine-1-carboxylic acid tert-butyl ester, followed by de-protection with HCl.

MS (m/z): 310 [M−HCl+H]$^+$; $^1$HNMR (400 MHz, DMSO, ppm): δ 1.91-2.00 (2H, m), 2.07-2.10 (2H, m), 2.49 (3H, s), 2.94-2.96 (3H, m), 3.36-3.38 (2H, m), 7.33-7.37 (1H, m), 7.50-7.54 (2H, m), 8.04-8.06 (2H, m), 8.57 (1H, s), 8.92 (1H, s), 12.35 (1H, s).

Example 87

[4-(4-Hydroxy-3-methyl-1-phenyl-1H-pyrazolo[3,4-d]pyrimidin-6-yl)-piperidin-1-yl]-piperidin-4-yl-methanone hydrochloride

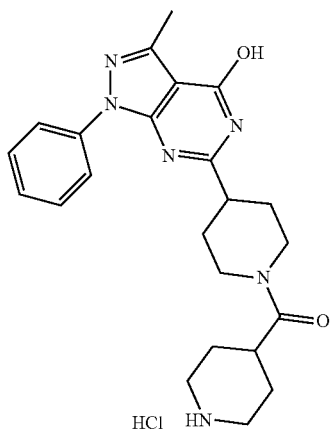 [SMILES: Cc1nn(-c2ccccc2)c2nc(C3CCN(C(=O)C4CCNCC4)CC3)nc(O)c12 ; Cl]

Step A: 4-[4-(4-Hydroxy-3-methyl-1-phenyl-1H-pyrazolo[3,4-d]pyrimidin-6-yl)-piperidine-1-carbonyl]-piperidine-1-carboxylic acid tert-butyl ester Into a 100-mL round-bottom flask, was placed a solution of 3-methyl-1-phenyl-6-(piperidin-4-yl)-1H-pyrazolo[3,4-d]pyrimidin-4(5H)-one hydrochloride (500 mg, 1.45 mmol, 1.00 equiv) in dichloromethane (50 mL) at room temperature. To the resulting mixture was then added 1-(tert-butoxycarbonyl)piperidine-4-carboxylic acid (332 mg, 1.45 mmol, 1.00 equiv), in portions at room temperature, followed by BOP (767 mg, 1.74 mmol, 1.20 equiv), in portions at room temperature. To the resulting mixture was added DIPEA (280 mg, 2.17 mmol, 1.50 equiv), in portions at room temperature. The resulting solution was stirred for 4 h at room temperature. The resulting mixture was washed with water (1×50 mL). The resulting solution was extracted with DCM (3×50 mL), the organic layers combined and concentrated under vacuum. The residue was applied onto a silica gel column with dichloromethane/methanol (50:1) to yield tert-butyl 4-(4-(3-methyl-4-oxo-1-phenyl-4,5-dihydro-1H-pyrazolo[3,4-d]pyrimidin-6-yl)piperidine-1-carbonyl)piperidine-1-carboxylate as a white solid.

Step B: [4-(4-Hydroxy-3-methyl-1-phenyl-1H-pyrazolo[3,4-d]pyrimidin-6-yl)-piperidin-1-yl]-piperidin-4-yl-methanone hydrochloride Into a 100-mL round-bottom flask, was placed a solution of tert-butyl 4-(4-(3-methyl-4-oxo-1-phenyl-4,5-dihydro-1H-pyrazolo[3,4-d]pyrimidin-6-yl)piperidine-1-carbonyl)piperidine-1-carboxylate (300 mg, 0.58 mmol, 1.00 equiv) in hydrogen chloride/$C_2H_8O_2$ (50 mL) at room temperature. The resulting solution was stirred for 4 h at room temperature. The solids were collected by filtration to yield 3-methyl-1-phenyl-6-(1-(piperidine-4-carbonyl)piperidin-4-yl)-1H-pyrazolo[3,4-d]pyrimidin-4(5H)-one hydrochloride as a white solid.

MS (m/z): 421 [M−HCl+H]$^+$; 1HNMR (400 MHz, D$_2$O, ppm): δ 1.59-1.78 (2H, m), 1.81-1.84 (2H, m), 1.86-2.00 (4H, m), 2.45 (3H, s), 2.78-2.92 (2H, m), 3.02-3.13 (3H, m), 3.22-3.28 (1H, m), 3.45-3.48 (2H, m), 4.05-4.09 (1H, m), 4.39-4.42 (1H, m), 7.37-7.39 (1H, m), 7.41-7.50 (2H, m), 7.67-7.69 (2H, m).

Example 88

3-Methyl-1-phenyl-6-(1-pyrrolidin-3-yl-piperidin-4-yl)-1H-pyrazolo[3,4-d]pyrimidin-4-ol hydrochloride

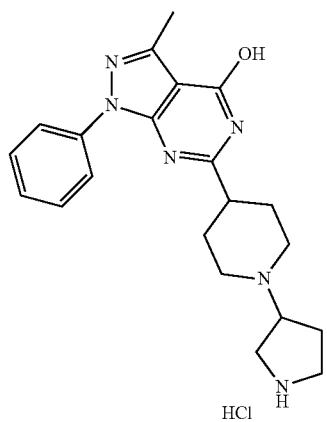 [SMILES: Cc1nn(-c2ccccc2)c2nc(C3CCN(C4CCNC4)CC3)nc(O)c12 ; Cl]

Step A: 3-[4-(4-Hydroxy-3-methyl-1-phenyl-1H-pyrazolo[3,4-d]pyrimidin-6-yl)-piperidin-1-yl]-pyrrolidine-1-carboxylic acid tert-butyl ester Into a 100-mL round-bottom flask, was placed a solution of 3-methyl-1-phenyl-6-(piperidin-4-yl)-1H-pyrazolo[3,4-d]pyrimidin-4(5H)-one hydrochloride (500 mg, 1.45 mmol, 1.00 equiv) in methanol (50 mL) at room temperature. To the resulting mixture was then added tert-butyl 3-oxopyrrolidine-1-carboxylate (804 mg, 4.35 mmol, 3.00 equiv), in portions at room temperature, followed by NaBH$_3$CN (456 mg, 7.24 mmol, 5.00 equiv) at room temperature. The resulting solution was stirred overnight at room temperature. The resulting mixture was concentrated under vacuum. The residue was dissolved in water (50 mL). The resulting solution was extracted with ethyl acetate (3×50 mL), the organic layers combined and concentrated under vacuum to yield tert-butyl 3-(4-(3-methyl-4-oxo-1-phenyl-4,5-dihydro-1H-pyrazolo[3,4-d]pyrimidin-6-yl)piperidin-1-yl)pyrrolidine-1-carboxylate as a white solid.

Step B: 3-Methyl-1-phenyl-6-(1-pyrrolidin-3-yl-piperidin-4-yl)-1H-pyrazolo[3,4-d]pyrimidin-4-ol hydrochloride Into a 100-mL round-bottom flask, was placed a solution of tert-butyl 3-(4-(3-methyl-4-oxo-1-phenyl-4,5-dihydro-1H-pyrazolo[3,4-d]pyrimidin-6-yl)piperidin-1-yl)pyrrolidine-1-carboxylate (400 mg, 0.84 mmol, 1.00 equiv) in hydrogen chloride/$C_2H_8O_2$ (50 mL) at room temperature. The resulting solution was stirred for 4 h at room temperature. The solids were collected by filtration to yield 3-methyl-1-phenyl-6-(1-(pyrrolidin-3-yl)piperidin-4-yl)-1H-pyrazolo[3,4-d]pyrimidin-4(5H)-one hydrochloride as a white solid.

MS (m/z): 379 [M−HCl+H]$^+$; $^1$HNMR (400 MHz, D$_2$O, ppm): δ 2.11-2.29 (5H, m), 2.50 (3H, s), 2.61 (1H, m), 3.06 (1H, m), 3.20-3.30 (2H, m), 3.36-3.39 (1H, m), 3.41-3.48

(1H, m), 3.51-3.64 (2H, m), 3.86-3.91 (1H, m), 4.05-4.13 (1H, m), 7.44-7.46 (1H, m), 7.53-7.57 (2H, m), 7.74-7.76 (2H, m).

Example 89

6-[1,4']Bipiperidinyl-4-yl-3-methyl-1-phenyl-1H-pyrazolo[3,4-d]pyrimidin-4-ol hydrochloride

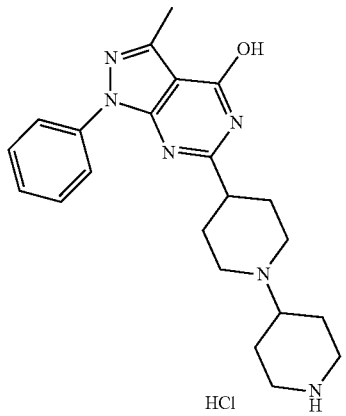 [SMILES: Cc1nn(-c2ccccc2)c2nc(C3CCN(C4CCNCC4)CC3)nc(O)c12 ; Cl]

Step A: 4-(4-Hydroxy-3-methyl-1-phenyl-1H-pyrazolo[3,4-d]pyrimidin-6-yl)-[1,4']bipiperidinyl-1'-carboxylic acid tert-butyl ester Into a 100-mL round-bottom flask, was placed a solution of 3-methyl-1-phenyl-6-(piperidin-4-yl)-1H-pyrazolo[3,4-d]pyrimidin-4(5H)-one hydrochloride (500 mg, 1.45 mmol, 1.00 equiv) in methanol (50 mL) at room temperature. To the resulting mixture was then added tert-butyl 4-oxopiperidine-1-carboxylate (865 mg, 4.35 mmol, 3.00 equiv), in portions at room temperature, followed by NaBH$_3$CN (460 mg, 7.30 mmol, 5.00 equiv), in portions at room temperature. The resulting solution was stirred overnight at room temperature. The resulting mixture was concentrated under vacuum. The residue was dissolved in water (50 mL). The resulting solution was extracted with ethyl acetate (3×50 mL), the organic layers combined and concentrated under vacuum to yield tert-butyl 4-(4-(3-methyl-4-oxo-1-phenyl-4,5-dihydro-1H-pyrazolo[3,4-d]pyrimidin-6-yl)piperidin-1-yl)piperidine-1-carboxylate as a white solid.

Step B: 6-[1,4']Bipiperidinyl-4-yl-3-methyl-1-phenyl-1H-pyrazolo[3,4-d]pyrimidin-4-ol hydrochloride Into a 100-mL round-bottom flask, was placed a solution of tert-butyl 4-(4-(3-methyl-4-oxo-1-phenyl-4,5-dihydro-1H-pyrazolo[3,4-d]pyrimidin-6-yl)piperidin-1-yl)piperidine-1-carboxylate (400 mg, 0.81 mmol, 1.00 equiv) in hydrogen chloride/C$_4$H$_8$O$_2$ (50 mL) at room temperature. The resulting solution was stirred for 4 h at room temperature. The solids were collected by filtration to yield 3-methyl-1-phenyl-6-(1-(piperidin-4-yl)piperidin-4-yl)-1H-pyrazolo[3,4-d]pyrimidin-4(5H)-one hydrochloride as a white solid.

MS (m/z): 386 [M−HCl+H]$^+$; 1HNMR (400 MHz, D$_2$O, ppm): δ 1.79-1.93 (2H, m), 2.12-2.25 (2H, m), 2.28-2.33 (4H, m), 2.50 (3H, s), 3.03-3.07 (3H, m), 3.30-3.36 (2H, m), 3.57-3.62 (5H, m), 7.46-7.47 (1H, m), 7.53-7.57 (2H, m), 7.73-7.74 (2H, m).

Example 90

6-(1-Azetidin-3-yl-piperidin-4-ylmethyl)-3-methyl-1-phenyl-1H-pyrazolo[3,4-d]pyrimidin-4-ol

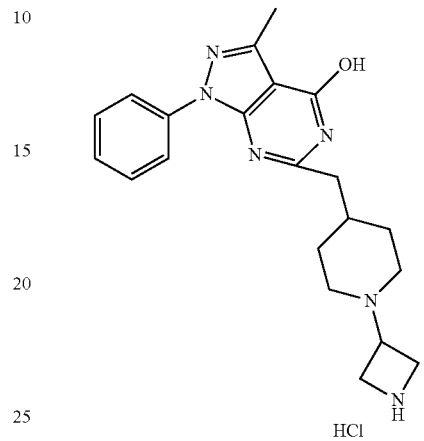

The title compound was prepared according to the procedure as described in Example 84 reacting 1-(1-tert-butoxycarbonyl-azetidin-3-yl)-piperidine-4-carboxylic acid ethyl ester, followed by de-protection with HCl.

MS (m/z): 379 [M−HCl+H]$^+$; $^1$HNMR: (400 MHz, D$_2$O, ppm): δ 1.47-1.56 (2H, m), 1.56-1.99 (2H, m), 2.11 (1H, m), 2.48 (3H, s), 2.62 (2H, m), 2.81-2.87 (2H, m), 3.38-3.40 (2H, m), 4.31-4.43 (5H, m), 7.42-7.44 (1H, m), 7.47-7.51 (2H, m), 7.57-7.58 (2H, m).

Example 91

3-Ethyl-1-phenyl-6-piperidin-4-yl-1H-pyrazolo[3,4-d]pyrimidin-4-ol hydrochloride

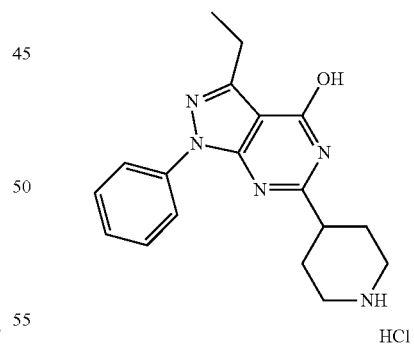

The title compound was prepared according to the procedure as described in Example 84 reacting 5-amino-3-ethyl-1-phenyl-1H-pyrazole-4-carboxylic acid amide and piperazine-1-carboxylic acid tert-butyl ester, followed by de-protection with HCl.

MS (m/z): 324 [M−HCl+H]$^+$; $^1$HNMR (400 MHz, D$_2$O, ppm): δ 1.19-1.23 (3H, t), 1.91-1.98 (2H, m), 2.00-2.15 (2H, m), 2.80-2.86 (2H, m), 2.93-2.98 (1H, m), 3.04-3.11 (2H, m), 3.45-3.48 (2H, m), 7.39-7.41 (1H, m), 7.47-7.51 (2H, m), 7.67-7.69 (2H, m).

Example 92

3-Ethyl-1-phenyl-6-(3,4,5,6-tetrahydro-2H-[1,4']bipyridinyl-4-yl)-1H-pyrazolo[3,4-d]pyrimidin-4-ol

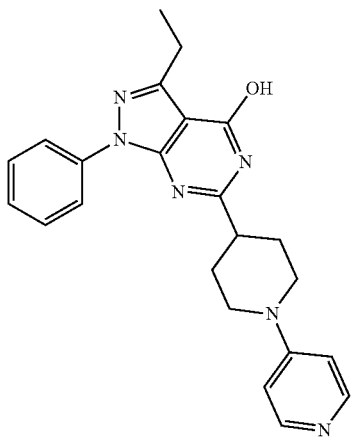 [SMILES: CCc1nn(-c2ccccc2)c2nc(C3CCN(c4ccncc4)CC3)nc(O)c12]

Into a 100-mL round-bottom flask, was placed a solution of 3-ethyl-1-phenyl-6-(piperidin-4-yl)-1H-pyrazolo[3,4-d]pyrimidin-4(5H)-one hydrochloride (200 mg, 0.56 mmol, 1.00 equiv) in N,N-dimethylformamide (40 mL) at room temperature. To the resulting mixture was then added 4-bromopyridine hydrochloride (131 mg, 0.68 mmol, 1.10 equiv), in portions at room temperature, followed by triethylamine (188 mg, 1.86 mmol, 3.00 equiv), in portions at room temperature. The resulting solution was stirred overnight at 130° C. The resulting mixture was concentrated under vacuum. The resulting residue (150 mg) was purified by Prep-HPLC with the following conditions (Gilson Pre-HPLC): Column, SHISEIDO, CAPCELL PAK C18, 20 mm ID*250 mm, 5 u; mobile phase, methanol/H₂O; Detector, UV 254 nm, to yield 3-ethyl-1-phenyl-6-(3,4,5,6-tetrahydro-2H-[1,4']bipyridinyl-4-yl)-1H-pyrazolo[3,4-d]pyrimidin-4-ol as a white solid.

MS (m/z): 401 [M−CF₃COOH+H]⁺; ¹HNMR (400 MHz, DMSO, ppm): δ 1.28-1.32 (3H, t), 1.78-1.87 (2H, m), 2.09-2.12 (2H, m), 2.86-2.92 (2H, m), 3.08-3.12 (2H, m), 3.38 (1H, m), 0.32-4.36 (2H, m), 7.23-7.25 (2H, m), 7.31-7.33 (1H, m), 7.48-7.52 (2H, m), 8.01-8.03 (2H, m), 8.22-8.24 (2H, m), 12.27 (1H, s), 13.23 (1H, s).

Example 93

3-Ethyl-1-phenyl-6-(3,4,5,6-tetrahydro-2H-[1,3']bipyridinyl-4-yl)-1H-pyrazolo[3,4-d]pyrimidin-4-ol

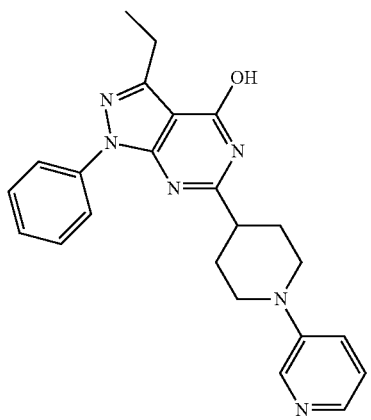 [SMILES: CCc1nn(-c2ccccc2)c2nc(C3CCN(c4cccnc4)CC3)nc(O)c12]

The title compound was prepared according to the procedure as described in Example 84 reacting 3,4,5,6-tetrahydro-2H-[1,3']bipyridinyl-4-carboxylic acid ethyl ester.

MS (m/z): 401 [M+H]⁺; ¹HNMR (400 MHz, DMSO, ppm): δ 1.29-1.33 (3H, t), 1.89-1.96 (2H, m), 2.02-2.05 (2H, m), 2.78-2.84 (2H, m), 2.85-2.93 (3H, m), 3.86-3.89 (2H, m), 7.20-7.23 (1H, m), 7.32-7.35 (2H, m), 7.50-7.54 (2H, m), 7.99 (1H, s), 8.00-8.09 (2H, m), 8.34-8.35 (1H, m), 12.28 (1H, s).

Example 94

3-Ethyl-1-phenyl-6-(1-pyrrolidin-3-yl-piperidin-4-yl)-1H-pyrazolo[3,4-d]pyrimidin-4-ol hydrochloride

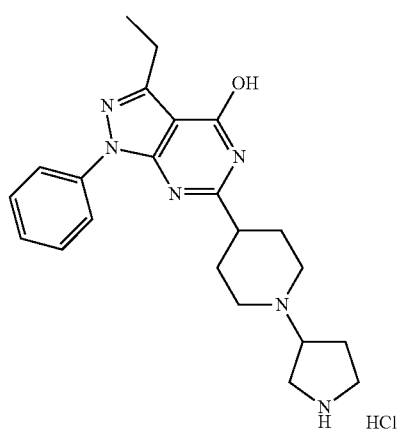 [SMILES: CCc1nn(-c2ccccc2)c2nc(C3CCN(C4CCNC4)CC3)nc(O)c12 ; Cl]

The title compound was prepared according to the procedure as described in Example 88 reacting via reductive amination 3-ethyl-1-phenyl-6-piperidin-4-yl-1H-pyrazolo[3,4-d]pyrimidin-4-ol hydrochloride and 3-oxo-pyrrolidine-1-carboxylic acid tert-butyl ester followed by de-protection of the adduct with HCl.

MS (m/z): 393 [M−HCl+H]⁺; ¹HNMR (400 MHz, D₂O, ppm): δ 1.20-1.30 (3H, t), 2.21-2.30 (5H, m), 2.61 (1H, m), 2.86-2.92 (2H, m), 3.08 (1H, m), 3.22-3.27 (2H, m), 0.30-3.48 (1H, m), 3.50-3.59 (1H, m), 3.60-3.69 (2H, m), 3.86-3.91 (1H, m), 4.07-4.11 (1H, m), 7.44-7.48 (1H, m), 7.54-7.58 (2H, m), 7.73-7.76 (2H, m).

Example 95

6-[1,4']Bipiperidinyl-4-yl-3-ethyl-1-phenyl-1H-pyrazolo[3,4-d]pyrimidin-4-ol hydrochloride

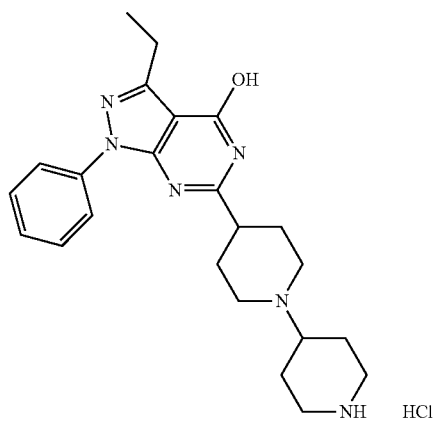 [SMILES: CCc1nn(-c2ccccc2)c2nc(C3CCN(C4CCNCC4)CC3)nc(O)c12 ; Cl]

The title compound was prepared according to the procedure as described in Example 88 reacting via reductive amination 3-ethyl-1-phenyl-6-piperidin-4-yl-1H-pyrazolo [3,4-d]pyrimidin-4-ol hydrochloride and 4-oxo-piperidine-1-carboxylic acid tert-butyl ester followed by de-protection of the adduct with HCl.

MS (m/z): 407 [M−HCl+H]$^+$; $^1$HNMR (400 MHz, D$_2$O, ppm): δ 1.25-1.29 (3H, t), 1.96-2.13 (2H, m), 2.26 (2H, m), 2.29-2.36 (4H, m), 2.89-2.95 (2H, m), 3.03-3.09 (3H, m), 3.20 (2H, m), 3.57-3.71 (5H, m), 7.47-7.49 (1H, m), 7.54-7.58 (2H, m), 7.73-7.75 (2H, m).

Example 96

[4-(3-Ethyl-4-hydroxy-1-phenyl-1H-pyrazolo[3,4-d] pyrimidin-6-yl)-piperidin-1-yl]-piperidin-4-yl-methanone hydrochloride

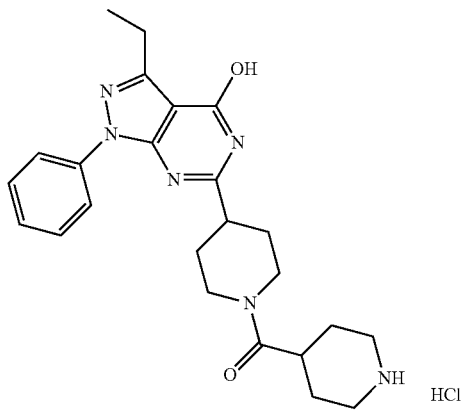 [SMILES: CCc1nn(-c2ccccc2)c2nc(C3CCN(C(=O)C4CCNCC4)CC3)nc(O)c12 ; Cl]

The title compound was prepared according to the procedure as described in Example 87 reacting 3-ethyl-1-phenyl-6-piperidin-4-yl-1H-pyrazolo[3,4-d]pyrimidin-4-ol hydrochloride and piperidine-1,4-dicarboxylic acid mono-tert-butyl ester followed by de-protection of the adduct with HCl.

MS (m/z): 435 [M−HCl+H]$^+$; $^1$HNMR (400 MHz, D$_2$O, ppm): δ 1.18-1.22 (3H, t), 1.56-1.66 (2H, m), 1.75-1.97 (6H, m), 2.76-2.82 (4H, m), 3.00-3.10 (3H, m), 3.19-3.26 (1H, m), 3.43-3.46 (2H, m), 4.02-4.06 (1H, m), 4.36-4.40 (1H, m), 7.32-7.39 (3H, m), 7.57-7.59 (2H, m).

Example 97

3-Methyl-1-phenyl-6-(4-piperazin-1-yl-phenyl)-1H-pyrazolo[3,4-b]pyridin-4-ol

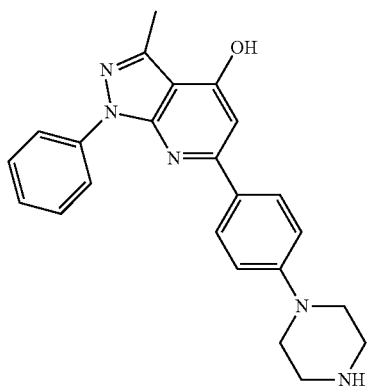 [SMILES: Cc1nn(-c2ccccc2)c2nc(-c3ccc(N4CCNCC4)cc3)cc(O)c12]

Step A: 3-Oxo-butyronitrile

Into a 2000 mL round-bottom flask, was placed a solution of acetonitrile (22.4 g, 546.34 mmol, 1.20 equiv) in tetrahydrofuran (800 mL), KO(CH$_3$)$_3$ (61.08 g, 545.36 mmol, 1.20 equiv), ethyl acetate (40 g, 454.55 mmol, 1.00 equiv). The resulting solution was stirred overnight at room temperature. The pH value of the solution was adjusted to about 2 with HCl (1 mol/L). The resulting solution was extracted with DCM (4×400 mL), the organic layers combined and dried over anhydrous sodium sulfate and concentrated under vacuum to yield 3-oxobutanenitrile as yellow oil.

Step B: 5-Methyl-2-phenyl-2H-pyrazol-3-ylamine

Into a 1000-mL 3-necked round bottom flask, was placed a solution of 3-oxobutanenitrile (23 g, 277.11 mmol, 1.00 equiv) in ethanol (400 mL), 1-phenylhydrazine (30 g, 277.78 mmol, 1.00 equiv). The resulting solution was heated to reflux overnight in an oil bath. The resulting mixture was then concentrated under vacuum. The residue was applied onto a silica gel column with ethyl acetate/petroleum ether (1:10-1:5) to yield 3-methyl-1-phenyl-1H-pyrazol-5-amine as a yellow solid.

Step C: 3-(4-Bromo-phenyl)-3-oxo-propionic acid ethyl ester

Into a 1000 mL 4-necked round-bottom flask purged and maintained with an inert atmosphere of nitrogen, was placed a solution of sodium hydride (10.1 g, 420.83 mmol, 2.10 equiv) in diethyl ether (400 mL). To the resulting mixture was then added diethyl carbonate (35.6 g, 301.69 mmol, 1.50 equiv) in 10 min at 0° C., followed by addition of a solution of 1-(4-bromophenyl)ethanone (40 g, 202.02 mmol, 1.00 equiv) in diethyl ether/EtOH (100 mL/1 mL) dropwise with stirring at 0° C. in 20 min. The resulting solution was heated to reflux for 3 hr. The reaction was then quenched by the addition of water/ice. The pH value of the solution was adjusted to about 5-6 with HCl (1 mol/L). The resulting solution was extracted with diethyl ether (3×200 mL), the organic layers combined and dried over anhydrous magnesium sulfate, then concentrated under vacuum. The residue was applied onto a silica gel column with ethyl acetate/petroleum ether (1:100) to yield ethyl 3-(4-bromophenyl)-3-oxopropanoate as yellow oil.

Step D: 6-(4-Bromo-phenyl)-3-methyl-1-phenyl-1,7-dihydro-pyrazolo[3,4-b]pyridin-4-one Into a 250 mL round-bottom flask, was placed a solution of 3-methyl-1-phenyl-1H-pyrazol-5-amine (20 g, 115.61 mmol, 1.00 equiv) in polyphosphoric acid (100 mL), ethyl 3-(4-bromophenyl)-3-oxopropanoate (31.21 g, 115.59 mmol, 1.00 equiv). The resulting solution was stirred overnight at 130° C. in an oil bath, then cooled to room temperature. The resulting solution was diluted with ice water:ethyl acetate (500 mL/500 mL). The resulting solution was extracted with ethyl acetate (5×500 mL), the organic layers combined and dried over anhydrous magnesium sulfate. The solids were filtered out. The resulting mixture was concentrated under vacuum. The resulting residue was applied onto a silica gel column with ethyl acetate/petroleum ether (1:20) to yield 6-(4-bromophenyl)-3-methyl-1-phenyl-1H-pyrazolo[3,4-b]pyridin-4(7H)-one as a white solid. $^1$HNMR (300 MHz, CDCl$_3$, ppm): δ 1.46-1.48 (3H, m), 6.87 (1H, s), 7.28-8.26 (9H, m).

Step E: 4-[4-(3-Methyl-4-oxo-1-phenyl-4,7-dihydro-1H-pyrazolo[3,4-b]pyridin-6-yl)-phenyl]-piperazine-1-carboxylic acid tert-butyl ester Into a 100 mL round-bottom flask purged and maintained with an inert atmosphere of nitrogen, was placed a solution of 6-(4-bromophenyl)-3-methyl-1-phenyl-1H-pyrazolo[3,4-b]pyridin-4(7H)-one (2500 mg, 6.58 mmol, 1.00 equiv) in toluene/DMF (30 ml/1 ml mL), tert-butyl piperazine-1-carboxylate (6130 mg, 32.96 mmol, 5.00 equiv), BINAP (410 mg, 0.65 mmol, 0.10 equiv), Pd$_2$(dba)$_3$ (602.9 mg, 0.66 mmol, 0.10 equiv), Cs$_2$CO$_3$ (3819 mg, 19.79 mmol, 3.00 equiv), dppf (270 mg). The resulting solution was stirred overnight at 120° C. in an oil bath. The resulting mixture was concentrated under vacuum. The residue was applied onto a silica gel column with dichloromethane/methanol (1:10) to yield tert-butyl 4-(4-(3-methyl-4-oxo-1-phenyl-4,7-dihydro-1H-pyrazolo[3,4-b]pyridin-6-yl)phenyl)piperazine-1-carboxylate as a white solid.

Step F: 3-Methyl-1-phenyl-6-(4-piperazin-1-yl-phenyl)-1H-pyrazolo[3,4-b]pyridin-4-ol Into a 50 mL round-bottom flask, was placed a solution of tert-butyl 4-(4-(3-methyl-4-oxo-1-phenyl-4,7-dihydro-1H-pyrazolo[3,4-b]pyridin-6-yl)phenyl)piperazine-1-carboxylate (300 mg, 0.62 mmol, 1.00 equiv) in dichloromethane (6 mL), trifluoroacetic acid (3 mL). The resulting solution was stirred for 2 h at room temperature. The resulting mixture was then concentrated under vacuum. The pH value of the solution was adjusted to about 9-10 with sodium bicarbonate. The resulting solution was extracted with of ethyl acetate (2×10 mL), the organic layers combined and dried over anhydrous magnesium sulfate. The residue was applied onto a silica gel column with MeOH:DCM (1:40) to yield 3-methyl-1-phenyl-6-(4-(piperazin-1-yl)phenyl)-1H-pyrazolo[3,4-b]pyridin-4(7H)-one as a yellow solid.

MS (m/z): 386 [M+H]$^+$; $^1$HNMR (300 MHz, CD$_3$OD, ppm): δ 2.71 (3H, s), 2.88-3.15 (8H, m), 6.92-8.29 (10H, m).

Example 98

6-[4-(3,5-Dimethyl-piperazin-1-yl)-phenyl]-3-ethyl-4-methoxy-1-phenyl-1H-pyrazolo[3,4-b]pyridine

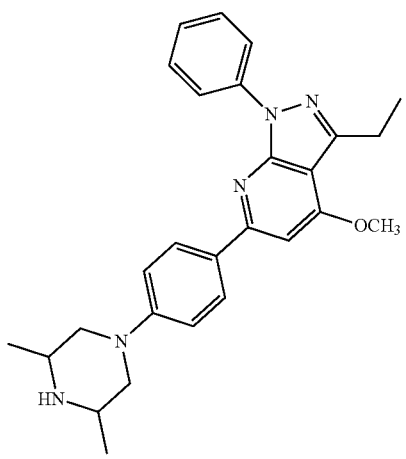 [SMILES: CCc1nn(-c2ccccc2)c2nc(-c3ccc(N4CC(C)NC(C)C4)cc3)cc(OC)c12]

Step A: 6-(4-Bromo-phenyl)-3-ethyl-4-methoxy-1-phenyl-1H-pyrazolo[3,4-b]pyridine Into a 50-mL round-bottom flask purged and maintained with an inert atmosphere of nitrogen, was placed a solution of 6-(4-bromophenyl)-3-ethyl-1-phenyl-1H-pyrazolo[3,4-b]pyridin-4(7H)-one (200 mg, 0.51 mmol, 1.00 equiv) in tetrahydrofuran (2 mL), PPh$_3$ (290 mg, 1.11 mmol, 2.17 equiv), methanol (18 mg, 0.56 mmol, 1.11 equiv). To the resulting mixture was then added DEAD (180 mg, 1.03 mmol, 2.03 equiv) dropwise with stirring at 0-5° C. The resulting solution was stirred overnight at room temperature. The reaction was then quenched by the addition of water (5 mL). The resulting solution was extracted with ethyl acetate (3×10 mL) and the organic layers combined. The resulting mixture was washed with water (1×10 mL). The resulting mixture was dried over anhydrous magnesium sulfate. The residue was applied onto a silica gel column with ethyl acetate/petroleum ether (Petroleum Ether-1:100) to yield 6-(4-bromo-phenyl)-3-ethyl-4-methoxy-1-phenyl-1H-pyrazolo[3,4-b]pyridine as a white solid. MS (m/z): 409 [MH$^+$].

Step B: 6-[4-(3,5-Dimethyl-piperazin-1-yl)-phenyl]-3-ethyl-4-methoxy-1-phenyl-1H-pyrazolo[3,4-b]pyridine Into a 50-mL round-bottom flask purged and maintained with an inert atmosphere of nitrogen, was placed a solution of 6-(4-bromophenyl)-3-ethyl-7-methyl-1-phenyl-1H-pyrazolo[3,4-b]pyridin-4(7H)-one (100 mg, 0.24 mmol, 1.00 equiv) in toluene/DMF (2 ml/Id), 2,6-dimethylpiperazine (140 mg, 1.23 mmol, 5.01 equiv), BINAP (15.3 mg, 0.02 mmol, 0.10 equiv), Pd$_2$(dba)$_3$ (22.4 mg, 0.02 mmol, 0.10 equiv), Cs$_2$CO$_3$ (140 mg, 0.73 mmol, 2.96 equiv), dppf (9.18 mg). The resulting solution was stirred overnight at 120° C. in an oil bath. The resulting mixture was concentrated under vacuum. The residue was applied onto a silica gel column with dichloromethane/methanol (200:1-100:1) to yield 6-[4-(3,5-dimethyl-piperazin-1-yl)-phenyl]-3-ethyl-4-methoxy-1-phenyl-1H-pyrazolo[3,4-b]pyridine as a yellow solid.

MS (m/z): 442 [M+H]$^+$; $^1$HNMR (300 MHz, CDCl$_3$, ppm): δ 1.29-1.69 (10H, m), 2.93-4.12 (10H, m), 6.96-8.43 (10H, m).

Example 99

4-Methoxy-3-methyl-1-phenyl-6-(4-piperazin-1-yl-phenyl)-1H-pyrazolo[3,4-b]pyridine

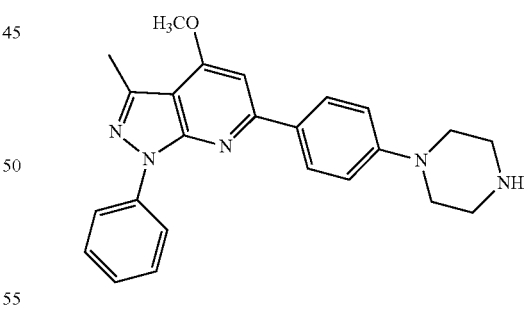

Step A: 4-[4-(4-Methoxy-3-methyl-1-phenyl-1H-pyrazolo[3,4-b]pyridin-6-yl)-phenyl]-piperazine-1-carboxylic acid tert-butyl ester Into a 50 mL round-bottom flask purged and maintained with an inert atmosphere of nitrogen, was placed a solution of tert-butyl 4-(4-(3-methyl-4-oxo-1-phenyl-4,7-dihydro-1H-pyrazolo[3,4-b]pyridin-6-yl)phenyl)piperazine-1-carboxylate (330 mg, 0.87 mmol, 1.00 equiv) in tetrahydrofuran (15 mL), PPh$_3$ (488 mg, 1.86 mmol, 2.20 equiv), MeOH (36 mg, 1.12 mmol, 1.10 equiv). To the resulting mixture was then added DEAD (237 mg, 1.36 mmol, 2.00 equiv) dropwise with stirring at 0-5° C. The resulting solution was stirred for 30 min at room temperature. The reaction was then quenched by the addition of water (5 mL). The resulting solution was extracted with ethyl acetate (3×10 mL) and the organic layers combined. The resulting mixture was washed with water (1×3 mL). The resulting mixture was dried over anhydrous magnesium sulfate. The residue was applied onto a silica gel column with ethyl acetate/petroleum ether (PE-1:100) to yield 4-[4-(4-methoxy-3-methyl-1-phenyl-1H-pyrazolo[3,4-b]pyridin-6-yl)-phenyl]-piperazine-1-carboxylic acid tert-butyl ester as a white solid. MS (m/z): 500 [MH$^+$].

Step B: 4-Methoxy-3-methyl-1-phenyl-6-(4-piperazin-1-yl-phenyl)-1H-pyrazolo[3,4-b]pyridine Into a 50 mL round-bottom flask, was placed a solution of tert-butyl 4-(4-(3,7-dimethyl-4-oxo-1-phenyl-4,7-dihydro-1H-pyrazolo[3,4-b]pyridin-6-yl)phenyl)piperazine-1-carboxylate (270 mg, 0.54 mmol, 1.00 equiv) in dichloromethane (6 mL), trifluoroacetic acid (3 mL). The resulting solution was stirred overnight at room temperature. The resulting mixture was concentrated under vacuum. The pH value of the solution was adjusted to about 9-10 with sodium bicarbonate. The resulting solution was extracted with of ethyl acetate (3×10 mL), the organic layers combined and dried over anhydrous magnesium sulfate. The residue was applied onto a silica gel column with methanol:CH$_2$Cl$_2$ (1:30) to yield 4-methoxy-3-methyl-1-phenyl-6-(4-piperazin-1-yl-phenyl)-1H-pyrazolo[3,4-b]pyridine as a white solid.

MS (m/z): 400 [M+H]$^+$; 1HNMR (300 MHz, CD$_3$OD, ppm): δ 1.30-1.46 (5H, m), 3.07-3.14 (8H, m), 7.07-8.30 (10H, m).

Example 100

3-Ethyl-1-phenyl-6-[4-(piperidin-4-ylamino)-phenyl]-1H-pyrazolo[3,4-b]pyridin-4-ol

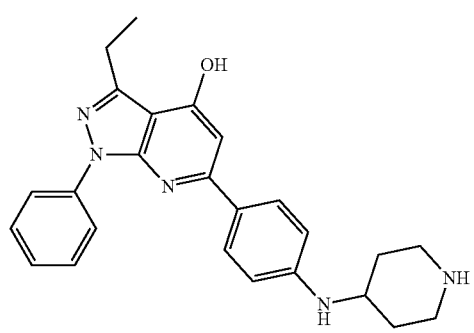 [SMILES: CCc1nn(-c2ccccc2)c2nc(-c3ccc(NC4CCNCC4)cc3)cc(O)c12]

The title compound was prepared according to the procedure as described in Example 97 reacting via Suzuki coupling of 6-(4-bromo-phenyl)-3-ethyl-1-phenyl-1,7-dihydro-pyrazolo[3,4-b]pyridin-4-one and 4-amino-piperidine-1-carboxylic acid tert-butyl ester, followed by de-protection with HCl.

MS (m/z): 414 [M+H]$^+$; $^1$HNMR (300 MHz, CD$_3$OD, ppm): δ: 1.42-3.76 (14H, m), 6.79-8.30 (10H, m), Example 101

3-Methyl-1-phenyl-6-[4-(piperidin-4-ylamino)-phenyl]-1H-pyrazolo[3,4-b]pyridin-4-ol

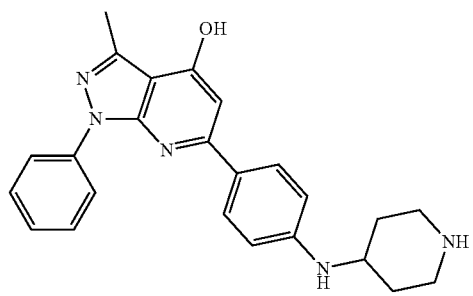 [SMILES: Cc1nn(-c2ccccc2)c2nc(-c3ccc(NC4CCNCC4)cc3)cc(O)c12]

The title compound was prepared according to the procedure as described in Example 97 reacting via Suzuki coupling of 6-(4-bromo-phenyl)-3-methyl-1-phenyl-1,7-dihydro-pyrazolo[3,4-b]pyridin-4-one and 4-amino-piperidine-1-carboxylic acid tert-butyl ester, followed by de-protection with HCl.

MS (m/z): 400 [M+H]$^+$; $^1$HNMR (300 MHz, CD$_3$OD, ppm): δ 0.917-3.70 (12H, m), 6.78-8.26 (10H, m).

Example 102

4-Ethoxy-3-ethyl-1-phenyl-6-(4-piperazin-1-yl-phenyl)-1H-pyrazolo[3,4-b]pyridine

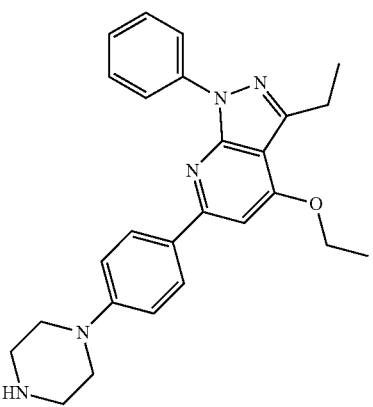 [SMILES: CCOc1cc(-c2ccc(N3CCNCC3)cc2)nc2c1c(CC)nn2-c1ccccc1]

The title compound was prepared according to the procedure as described in Example 98 reacting 6-(4-bromo-phenyl)-3-ethyl-4-ethoxy-1-phenyl-1H-pyrazolo[3,4-b]pyridine (according to Example 98) and piperazine-1-carboxylic acid tert-butyl ester, followed by de-protection with HCl.

MS (m/z): 428 [M+H]$^+$; $^1$HNMR (300 MHz, CD$_3$OD, ppm): δ 1.41-1.45 (3H, m), 1.57-1.60 (3H, m), 3.04-3.09 (6H, m), 3.29 (4H, m), 4.42-4.43 (2H, m), 7.08-8.34 (10H, m).

Example 103

4-Ethoxy-3-ethyl-6-[4-(4-methyl-piperazin-1-yl)-phenyl]-1-phenyl-1H-pyrazolo[3,4-b]pyridine

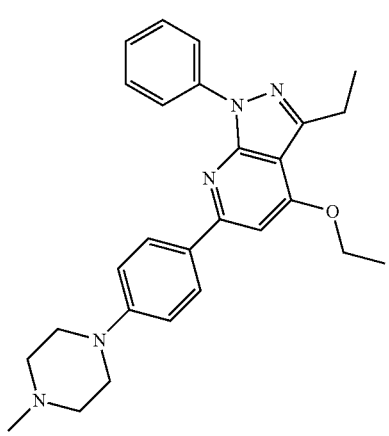 [SMILES: CCOc1cc(-c2ccc(N3CCN(C)CC3)cc2)nc2c1c(CC)nn2-c1ccccc1]

The title compound was prepared according to the procedure as described in Example 98 reacting 6-(4-bromo-phenyl)-3-ethyl-4-ethoxy-1-phenyl-1H-pyrazolo[3,4-b]pyridine (according to Example 98) and 1-methyl-piperazine.

MS (m/z): 442 [M+H]⁺; ¹HNMR (300 MHz, CD₃OD, ppm): δ 1.41-1.45 (3H, m), 1.56-1.60 (3H, m), 2.39 (3H, s), 2.66-2.68 (4H, t), 3.07-3.09 (2H, m), 3.32-3.36 (4H, m), 4.41-4.43 (2H, m), 7.07-8.34 (10H, m).

Example 104

6-[4-(3,5-Dimethyl-piperazin-1-yl)-phenyl]-4-ethoxy-3-ethyl-1-phenyl-1H-pyrazolo[3,4-b]pyridine

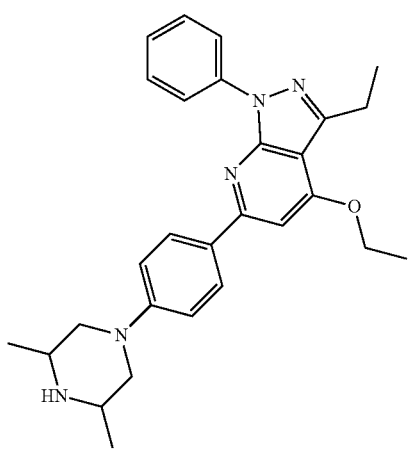 [SMILES: CCOc1cc(-c2ccc(N3CC(C)NC(C)C3)cc2)nc2c1c(CC)nn2-c1ccccc1]

The title compound was prepared according to the procedure as described in Example 98 reacting 6-(4-bromo-phenyl)-3-ethyl-4-ethoxy-1-phenyl-1H-pyrazolo[3,4-b]pyridine (according to Example 98) and 2,6-dimethyl-piperazine-1-carboxylic acid tert-butyl ester, followed by de-protection with HCl.

MS (m/z): 456 [M+H]⁺; ¹HNMR (300 MHz, CD₃OD, ppm): δ 1.19-1.20 (6H, m), 1.40-1.44 (3H, t), 1.56-1.59 (3H, t), 2.35-2.41 (2H, t), 3.03-3.09 (4H, m), 3.73-3.76 (2H, d), 4.40-4.42 (2H, m), 7.07-8.33 (10H, m).

Example 105

3-Methylsulfanyl-6-(1,2,3,6-tetrahydropyridin-4-yl)-1-(3-methylphenyl)-1H-indazole

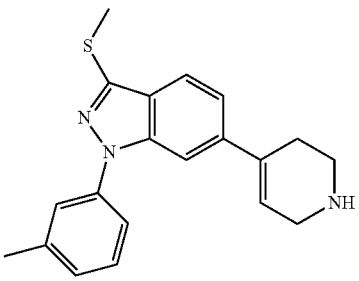 [SMILES: CSc1nn(-c2cccc(C)c2)c2cc(C3=CCNCC3)ccc12]

STEP A: 4-(1H-Indazol-6-yl)-3,6-dihydro-2H-pyridine-1-carboxylic acid tert-butyl ester To a mixture of 6-bromoindazole (2.0 g, 10.2 mmol), 4-(4,4,5,5-tetramethyl-[1,3,2]dioxaborolan-2-yl)-3,6-dihydro-2H-pyridine-1-carboxylic acid tert-butyl ester (3.5 g, 11.2 mmol) and Pd(PPh₃)₄ (1.2 g, 1.0 mmol) under N₂ were added 1,4-dioxane (80 mL), followed by addition of K₂CO₃ (2 M in H₂O, 20 mL, 40 mmol). The resulting mixture was heated at 110° C. for 16 h, then cooled to room temperature. The resulting mixture was then treated with saturated Na₂CO₃ aqueous solution. The resulting mixture was extracted with EtOAc (3×). The combined extracts were washed with brine and then dried over Na₂SO₄. The resulting mixture was filtered, concentrated under reduced pressure, and the residue purified by flash chromatography on silica-gel (gradient eluent heptane to 60% EtOAc in heptane) to yield 4-(1H-indazol-6-yl)-3,6-dihydro-2H-pyridine-1-carboxylic acid tert-butyl ester as brownish foam solid.

STEP B: 4-(3-Iodo-1H-indazol-6-yl)-3,6-dihydro-2H-pyridine-1-carboxylic acid tert-butyl ester A solution of 4-(1H-indazol-6-yl)-3,6-dihydro-2H-pyridine-1-carboxylic acid tert-butyl ester (9.70 g, 3.24 mmol) in DMF (32 mL) at room temperature was treated with iodine (1.23 g, 4.86 mmol) and KOH (grounded, 454 mg, 8.1 mmol). The resulting mixture was stirred at room temperature for 40 min, then treated with saturated Na₂S₂O₃ aqueous solution. The resulting mixture was then extracted with EtOAc (3×). The combined extracts were washed with brine and dried over Na₂SO₄. The resulting mixture was filtered and concentration under reduced pressure. The resulting residue was purified by flash chromatography on silica-gel (gradient eluant 10% to 40% EtOAc in heptane) to yield the title compound as white solid.

STEP C: 4-(3-Methylsulfanyl-1H-indazol-6-yl)-3,6-dihydro-2H-pyridine-1-carboxylic acid tert-butyl ester To a mixture of 4-(3-iodo-1H-indazol-6-yl)-3,6-dihydro-2H-pyridine-1-carboxylic acid tert-butyl ester (213 mg, 0.50 mmol), sodium methanethiolate (39 mg, 0.55 mmol) and sodium tert-butoxide (67 mg, 0.7 mmol) in a pre-dried flask sealed under $N_2$ was added 1 mL of a catalyst solution, which was prepared by mixing Pd(OAc)$_2$ (12.4 mg, 0.055 mml) and JOSIPHOS CyPF-t-Bu (30.6 mg, 0.055 mmol) in DME (1.1 mL) under $N_2$. The resulting mixture was heated in 100° C. oil bath for 5 h, then cooled and loaded onto a silica-gel column and chromatography (gradient eluant 20% to 50% EtOAc in heptane) to yield 4-(3-Methylsulfanyl-1H-indazol-6-yl)-3,6-dihydro-2H-pyridine-1-carboxylic acid tert-butyl ester as white crystalline solid.

STEP D: 4-(3-Methylsulfanyl-1-m-tolyl-1H-indazol-6-yl)-3,6-dihydro-2H-Pyridine-1-carboxylic acid tert-butyl ester To a mixture of 4-(3-methylsulfanyl-1H-indazol-6-yl)-3,6-dihydro-2H-pyridine-1-carboxylic acid tert-butyl ester (63 mg, 0.18 mmol) and 3-methyl phenyl boronic acid (50 mg, 0.36 mmol) in CH$_2$Cl$_2$ (1.5 mL) were added TEA (0.051 mL, 0.36 mmol) and Cu(OAc)$_2$ (33 mg, 0.18 mmol). The resulting mixture was stirred at room temperature for 16 h. The resulting mixture was loaded onto a silica-gel column and chromatography (gradient eluent heptane to 50% EtOAc in heptane) to yield 4-(3-Methylsulfanyl-1-m-tolyl-1H-indazol-6-yl)-3,6-dihydro-2H-pyridine-1-carboxylic acid tert-butyl ester as colorless film stuck on flask wall.

STEP E: 3-Methylsulfanyl-6-(1,2,3,6-tetrahydro-pyridin-4-yl)-1-m-tolyl-1H-indazole A solution of 4-(3-methylsulfanyl-1-m-tolyl-1H-indazol-6-yl)-3,6-dihydro-2H-pyridine-1-carboxylic acid tert-butyl ester (22.5 mg, 0.052 mmol) in 4 N HCl in 1,4-dioxane (3 mL) was stirred at room temperature for 1 h, then concentrated. The resulting residue was triturated and sonicated in a mixture of MeOH (0.5 mL)/diethyl ether (5 mL). The resulting mixture was filtered to yield the title compound as a yellowish solid.

$^1$H NMR (400 MHz, CD$_3$OD) δ 7.72 (d, J=8 Hz, 1H), 7.69 (s, 1H), 7.38-7.55 (m, 4H), 7.24 (d, J=8 Hz, 1H), 6.25-6.29 (m, 1H), 3.86-3.90 (m, 2H), 3.49 (t, J=8 Hz, 2H), 2.85-2.90 (m, 2H), 2.70 (s, 3H), 2.46 (s, 3H); m/z (M+H$^+$) 336.

Example 106

1-(3-Fluoro-phenyl)-3-methylsulfanyl-6-(1,2,3,6-tetrahydro-pyridin-4-yl)-1H-indazole

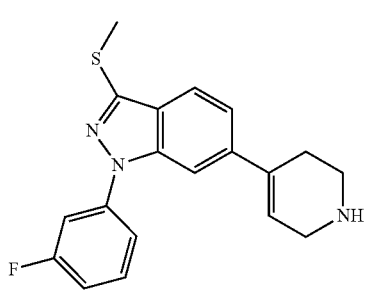

The title compound was prepared as a white solid by coupling 4-(3-methylsulfanyl-1H-indazol-6-yl)-3,6-dihydro-2H-pyridine-1-carboxylic acid tert-butyl ester and 3-fluoro-phenyl boronic acid to yield an intermediate, which was de-protected to remove the N-Boc group.

$^1$H NMR (400 MHz, CD$_3$OD) δ 7.78 (s, 1H), 7.71 (d, J=8 Hz, 1H), 7.50-7.63 (m, 3H), 7.42 (d, J=8 Hz, 1H), 7.09-7.16 (m, 1H), 6.27-6.31 (m, 1H), 3.86-3.91 (m, 2H), 3.46-3.51 (m, 2H), 2.86-2.92 (m, 2H), 2.72 (s, 3H); m/z (M+H$^+$) 340.

Example 107

3-Methylsulfanyl-6-(1,2,3,6-tetrahydro-pyridin-4-yl)-1-p-tolyl-1H-indazole

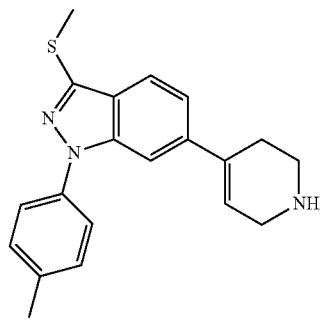 [SMILES: CSc1nn(-c2ccc(C)cc2)c2cc(C3=CCNCC3)ccc12]

The title compound was prepared as a white solid by coupling 4-(3-methylsulfanyl-1H-indazol-6-yl)-3,6-dihydro-2H-pyridine-1-carboxylic acid tert-butyl ester and 4-methylphenyl boronic acid to yield an intermediate, which was de-protected to remove the N-Boc.

$^1$H NMR (400 MHz, CD$_3$OD) δ 7.71 (d, J=8 Hz, 1H), 7.66 (s, 1H), 7.58 (d, J=8 Hz, 2H), 7.37-7.43 (m, 3H), 6.25-6.30 (m, 1H), 3.85-3.90 (m, 2H), 3.48 (t, J=8 Hz, 2H), 2.83-2.90 (m, 2H), 2.68 (s, 3H), 2.44 (s, 3H); m/z (M+H$^+$) 336.

Additional representative compounds of the present invention were similarly prepared according to the procedures as described in the Schemes and Examples herein, selecting and substituting suitably substituted reagents, as would be readily recognized by one skilled in the art. Table 9 below, lists said prepared compounds of formula (I) along with the measured mass spec values.

TABLE 9

Representative Compounds of Formula (I)

| ID No. | Name | Measured MS (MH$^+$) |
|---|---|---|
| 106 | 1-(4-Methoxy-phenyl)-3-methylsulfanyl-6-(4-piperidin-4-yl-piperazin-1-yl)-1H-indazole | 438 |
| 107 | 3-Methylsulfanyl-1-phenyl-6-(piperidin-4-ylmethoxy)-1H-indazole | 354 |
| 108 | Ethyl-(3-methylsulfanyl-1-phenyl-1H-indazol-6-yl)-piperidin-4-ylmethyl-amine | 381 |
| 109 | (3-Methylsulfanyl-1-phenyl-1H-indazol-6-yl)-piperidin-4-yl-amine | 339 |
| 110 | 3-Methylsulfanyl-1-(4-nitro-phenyl)-1H-indazole-6-carboxylic acid piperidin-4-ylamide | 412 |
| 111 | 1-(4-Amino-phenyl)-3-methylsulfanyl-1H-indazole-6-carboxylic acid piperidin-4-ylamide | 382 |
| 112 | (3-Methylsulfanyl-1-phenyl-1H-indazol-6-yl)-piperidin-4-ylmethyl-amine | 353 |
| 115 | 4-(3-Methylsulfanyl-6-piperazin-1-ylmethyl-indazol-1-yl)-phenylamine | 354 |
| 116 | 4-[3-Methylsulfanyl-6-(1,2,3,6-tetrahydro-pyridin-4-yl)-indazol-1-yl]-phenylamine | 337 |
| 118 | 3-Methylsulfanyl-6-piperazin-1-yl-1-m-tolyl-1H-indazole | 339 |
| 119 | 3-Methylsulfanyl-6-(4-piperidin-4-yl-piperazin-1-yl)-1-m-tolyl-1H-indazole | 422 |

TABLE 9-continued

Representative Compounds of Formula (I)

| ID No. | Name | Measured MS (MH+) |
|---|---|---|
| 121 | 3-Methylsulfanyl-1-phenyl-6-(piperidin-4-yloxy)-1H-indazole | 340 |
| 122 | 1-(4-Methoxy-phenyl)-3-methylsulfanyl-6-piperazin-1-yl-1H-indazole | 355 |
| 124 | 3-Methylsulfanyl-1-(4-nitro-phenyl)-6-(1,2,3,6-tetrahydro-pyridin-4-yl)-1H-indazole | 367 |
| 126 | 1-(3,5-Difluoro-phenyl)-3-methylsulfanyl-6-(4-piperidin-4-yl-piperazin-1-yl)-1H-indazole | 444 |
| 127 | 1-(4-Bromo-phenyl)-3-methylsulfanyl-6-(piperidin-4-yloxy)-1H-indazole | 419 |
| 128 | 1-(4-Bromo-phenyl)-3-methylsulfanyl-6-(piperidin-4-ylmethoxy)-1H-indazole | 433 |
| 130 | 3-Methylsulfanyl-1-(4-nitro-phenyl)-6-piperazin-1-ylmethyl-1H-indazole | 384 |
| 131 | N-(3-Methylsulfanyl-1-phenyl-1H-indazol-6-yl)-2-piperazin-1-yl-acetamide | 382 |
| 132 | N-(3-Methylsulfanyl-1-phenyl-1H-indazol-6-yl)-3-piperazin-1-yl-propionamide | 396 |
| 133 | [3-Methylsulfanyl-1-(4-nitro-phenyl)-1H-indazol-6-yl]-piperazin-1-yl-methanone | 398 |
| 135 | 1-(4-Fluoro-phenyl)-3-methylsulfanyl-6-(4-piperidin-4-yl-piperazin-1-yl)-1H-indazole | 426 |
| 136 | (3-Methylsulfanyl-1-phenyl-1H-indazol-6-yl)-piperidin-4-yl-methanol | 354 |
| 137 | (3-Methylsulfanyl-1-phenyl-1H-indazol-6-yl)-pyridin-4-yl-methanol | 348 |
| 139 | 1-(4-Fluoro-phenyl)-3-methylsulfanyl-6-(1,2,3,6-tetrahydro-pyridin-4-yl)-1H-indazole | 340 |
| 140 | 1-(4-Methoxy-phenyl)-3-methylsulfanyl-6-(1,2,3,6-tetrahydro-pyridin-4-yl)-1H-indazole | 352 |
| 141 | 3-Methylsulfanyl-1-phenyl-6-(2-piperidin-4-yl-vinyl)-1H-indazole | 350 |
| 142 | (3-Methylsulfanyl-1-phenyl-1H-indazol-6-yl)-piperidin-4-yl-methanone | 352 |
| 143 | 3-Methylsulfanyl-1-phenyl-6-(1,2,3,6-tetrahydro-pyridin-4-yl)-1H-indazole | 322 |
| 144 | 2-Amino-1-{4-[3-methylsulfanyl-1-(4-nitro-phenyl)-1H-indazol-6-yl]-3,6-dihydro-2H-pyridin-1-yl}-ethanone | 424 |
| 149 | 3-Amino-1-[4-(3-methylsulfanyl-1-phenyl-1H-indazol-6-yl)-3,6-dihydro-2H-pyridin-1-yl]-propan-1-one | 393 |
| 152 | 3-Methylsulfanyl-1-phenyl-6-(2-[1,2,4]triazol-1-yl-vinyl)-1H-indazole | 334 |
| 153 | 3-Methylsulfanyl-1-phenyl-6-(2-piperidin-4-yl-vinyl)-1H-indazole | 350 |
| 154 | 3-Methylsulfanyl-1-phenyl-6-(2-pyridin-4-yl-vinyl)-1H-indazole | 344 |
| 155 | 3-Methylsulfanyl-1-phenyl-6-(2-pyridin-2-yl-vinyl)-1H-indazole | 344 |
| 157 | 4-Amino-piperidine-4-carboxylic acid (3-methylsulfanyl-1-phenyl-1H-indazol-6-yl)-amide | 382 |
| 158 | 4-Methyl-piperidine-4-carboxylic acid (3-methylsulfanyl-1-phenyl-1H-indazol-6-yl)-amide | 381 |
| 160 | 1-(3-Methylsulfanyl-1-phenyl-1H-indazol-6-yl)-2-piperidin-4-yl-ethanone | 366 |
| 161 | 1-(3-Methylsulfanyl-1-phenyl-1H-indazol-6-yl)-2-piperidin-3-yl-ethanone | 366 |
| 163 | 1-(3-Methylsulfanyl-1-phenyl-1H-indazol-6-yl)-2-pyrrolidin-2-yl-ethanone | 352 |
| 164 | 3-Methylsulfanyl-1-phenyl-6-pyridin-4-yl-1H-indazole | 318 |
| 165 | (3-Methylsulfanyl-1-phenyl-1H-indazol-6-yl)-(2-piperazin-1-yl-ethyl)-amine | 368 |
| 166 | (3-Methylsulfanyl-1-phenyl-1H-indazol-6-yl)-(2-piperidin-4-yl-ethyl)-amine | 367 |
| 167 | 4-Fluoro-piperidine-4-carboxylic acid (3-methylsulfanyl-1-phenyl-1H-indazol-6-yl)-amide | 385 |
| 168 | 1-(3-Methylsulfanyl-1-phenyl-1H-indazol-6-yl)-2-piperazin-1-yl-ethane-1,2-dione | 381 |
| 171 | (3-Methyl-3H-benzoimidazol-5-yl)-(3-methylsulfanyl-1-phenyl-1H-indazol-6-yl)-methanone | 399 |
| 172 | 4-Phenyl-piperidine-4-carboxylic acid (3-methylsulfanyl-1-phenyl-1H-indazol-6-yl)-amide | 443 |
| 173 | [1-(4-Methoxy-phenyl)-3-methylsulfanyl-1H-indazol-6-yl]-(3-methyl-3H-benzoimidazol-5-yl)-methanone | 429 |
| 174 | Benzo[1,2,5]oxadiazol-5-yl-(3-methylsulfanyl-1-phenyl-1H-indazol-6-yl)-methanone | 387 |
| 175 | 3-Methylsulfanyl-1-phenyl-6-(2-pyrrolidin-2-yl-vinyl)-1H-indazole | 336 |
| 176 | 3-Methylsulfanyl-1-phenyl-6-(2-piperidin-3-yl-vinyl)-1H-indazole | 350 |
| 178 | 6-[2-(6-Methyl-pyridin-3-yl)-vinyl]-3-methylsulfanyl-1-phenyl-1H-indazole | 358 |
| 180 | 3-Methylsulfanyl-6-(1,2,3,6-tetrahydro-pyridin-4-yl)-1-o-tolyl-1H-indazole | 336 |
| 185 | 3-Methylsulfanyl-1-phenyl-6-(2-piperidin-4-yl-ethyl)-1H-indazole | 352 |

Biological Example 1

In Vitro KHK Enzyme Assay

An enzymatic assay was developed to measure KHK-mediated conversion of D-fructose to Fructose-1-P (F-1-P) using High Throughput Mass Spectroscopy (HTMS) as a means of product detection. This assay served as a primary screen to evaluate the ability to inhibit KHK enzyme activity and it has been adapted to high throughput mass spectrometry (HTMS, BioTrove RapidFire™) format for higher throughput.

The compounds to be tested were dosed in 12-points concentration from 511 µM to 0.5 µM. Inhibition of the fragment, $IC_{50}$, was determined in a dose-response curve under the established steady-state conditions of 200 µM fructose, 100 µM ATP and 2 nM KHK for 60 min at 25° C. The assay was carried out in 384-well plate format.

Representative compounds of the present invention were tested according to the procedure described above, with results as listed in Table 10, below.

TABLE 10

KHK Enzyme Assay Activity

| ID No. | HTMS KHK $IC_{50}$ (µM) |
|---|---|
| 1 | 0.56 |
| 2 | 0.22 |
| 3 | 0.86 |
| 4 | 0.45 |
| 5 | 0.59 |
| 6 | 0.59 |
| 7 | 0.70 |
| 8 | 1.01 |
| 9 | 2.68 |
| 10 | 0.71 |
| 11 | 0.54 |
| 12 | 0.31 |
| 13 | 0.26 |
| 14 | 0.23 |
| 15 | 0.56 |
| 16 | 2.89 |
| 17 | 2.03 |
| 18 | 2.03 |
| 19 | 0.56 |
| 20 | 0.67 |
| 21 | 2.82 |
| 22 | 4.45 |
| 23 | 0.68 |
| 24 | 1.56 |
| 25 | 0.46 |
| 26 | 1.47 |
| 27 | 5.17 |

TABLE 10-continued

KHK Enzyme Assay Activity

| ID No. | HTMS KHK IC$_{50}$ (µM) |
|---|---|
| 28 | 3.04 |
| 29 | 0.30 |
| 30 | 16.4 |
| 31 | 4.95 |
| 32 | 6.06 |
| 33 | 5.34 |
| 34 | 0.83 |
| 35 | 0.43 |
| 36 | 0.89 |
| 37 | 5.87 |
| 38 | 0.94 |
| 39 | not tested |
| 40 | 0.68 |
| 41 | >30 |
| 42 | 0.57 |
| 43 | 2.35 |
| 44 | 2.40 |
| 45 | 2.06 |
| 46 | 0.56 |
| 47 | 3.51 |
| 48 | 2.37 |
| 49 | 1.80 |
| 50 | 5.36 |
| 51 | 1.47 |
| 52 | 9.8 |
| 53 | 4.81 |
| 54 | 4.52 |
| 55 | 11.5 |
| 56 | 0.86 |
| 57 | 3.20 |
| 58 | 7.50 |
| 59 | 1.28 |
| 60 | 2.30 |
| 61 | 1.01 |
| 62 | 1.60 |
| 63 | 3.75 |
| 64 | 9.06 |
| 65 | 7.73 |
| 66 | 0.16 |
| 67 | 1.23 |
| 68 | 1.57 |
| 69 | 14.2 |
| 70 | 14.7 |
| 71 | 0.40 |
| 72 | 0.68 |
| 73 | 0.39 |
| 74 | 5.96 |
| 75 | 0.31 |
| 76 | 1.38 |
| 77 | 8.10 |
| 78 | 4.42 |
| 79 | >30 |
| 80 | 4.50 |
| 81 | 30 |
| 82 | 23 |
| 83 | >30 |
| 84 | >30 |
| 85 | 7.45 |
| 86 | 6.1 |
| 87 | >30 |
| 88 | 1.51 |
| 89 | 14 |
| 90 | >30 |
| 91 | 2.40 |
| 92 | 1.67 |
| 93 | 7.90 |
| 94 | 5.27 |
| 95 | 11.5 |
| 96 | 30 |
| 97 | 2.71 |
| 98 | 0.30 |
| 99 | 0.60 |
| 100 | 1.72 |
| 101 | 0.89 |
| 102 | 1.43 |
| 103 | 0.66 |
| 104 | 14.7 |
| 106 | 0.36 |
| 107 | 0.44 |
| 108 | 0.89 |
| 109 | 0.77 |
| 110 | 9.83 |
| 111 | 2.61 |
| 112 | 0.42 |
| 115 | >51 |
| 116 | 0.16 |
| 118 | 4.12 |
| 119 | 0.38 |
| 121 | 0.71 |
| 122 | 0.83 |
| 124 | 0.49 |
| 126 | 4.22 |
| 127 | 2.05 |
| 128 | 0.92 |
| 130 | 44.94 |
| 131 | 0.68 |
| 132 | 0.38 |
| 133 | >51 |
| 135 | 1.65 |
| 136 | >2 |
| 137 | >2 |
| 139 | 0.23 |
| 140 | 0.09 |
| 141 | 0.23 |
| 142 | 0.67 |
| 143 | not tested |
| 144 | >10 |
| 147 | 0.03 |
| 149 | 0.48 |
| 152 | >10 |
| 153 | 0.40 |
| 154 | >10 |
| 155 | >10 |
| 157 | 0.30 |
| 158 | 0.70 |
| 160 | 1.00 |
| 161 | 6.62 |
| 163 | 8.28 |
| 164 | >10 |
| 165 | 0.89 |
| 166 | 0.60 |
| 167 | 0.66 |
| 168 | 4.12 |
| 171 | >10 |
| 172 | 2.15 |
| 173 | >10 |
| 174 | >10 |
| 175 | 0.61 |
| 176 | 0.79 |
| 178 | >10 |
| 179 | 0.04 |
| 180 | >10 |
| 184 | 0.04 |
| 185 | 0.92 |

Formulation Example

Solid, Oral Dosage Form

Prophetic Example

As a specific embodiment of an oral composition, 100 mg of the Compound #147, prepared as in Example 105 above, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed:
1. A compound of formula (I)

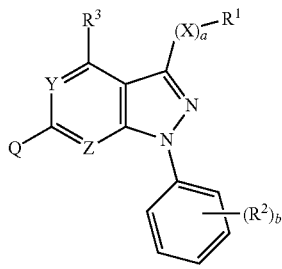

wherein
a is an integer from 0 to 1;
X is selected from the group consisting of —O— and —S—;
$R^1$ is selected from the group consisting of $C_{1-4}$alkyl and halogenated $C_{1-4}$alkyl;
b is an integer from 0 to 2;
$R^2$ is selected from the group consisting of halogen, hydroxy, cyano, nitro, $NR^A R^B$, $C_{1-4}$alkyl, —O—$C_{1-4}$alkyl, —S—$C_{1-4}$alkyl and halogenated $C_{1-4}$alkyl; wherein $R^A$ and $R^B$ are each independently selected from the group consisting of hydrogen and $C_{1-4}$alkyl;
$R^3$ is selected from the group containing of hydrogen, halogen, hydroxy, —O—$C_{1-4}$alkyl and $NR^C R^D$; wherein $R^C$ and $R^D$ are each independently selected from the group consisting of hydrogen and $C_{1-4}$alkyl;
Y is CH and Z is CH;
Q is selected from the group consisting of -($L^1$)$_c$-(Ring A), -($L^1$)$_c$-(Ring B)-(Ring C) and -(Ring B)-$L^1$-(Ring C);
c is an integer from 0 to 1;
$L^1$ is selected from the group consisting of —CH$_2$—, —CH(OH)—, —CH$_2$CH$_2$—, —CH$_2$CH$_2$CH$_2$—, —CH=CH—, —CH=CH—CH$_2$—, —O—, —O—CH$_2$—, —C(O)—, —C(O)—C(O)—, —C(O)—CH$_2$—, —C(O)—N($R^4$)—, —N($R^4$)—, —N($R^4$)—CH$_2$—, —N($R^4$)—CH$_2$CH$_2$—, —N($R^4$)—(CO)—, —N($R^4$)—C(O)—CH$_2$—, —N($R^4$)—C(O)—CH$_2$CH$_2$— and —N($R^4$)—C(O)—N($R^5$)—; wherein $R^4$ and $R^5$ are each independently selected from the group consisting of hydrogen and $C_{1-2}$alkyl;
(Ring A) is selected from the group consisting of phenyl and 4 to 10 membered, nitrogen containing ring structure; wherein (Ring A) is optionally substituted with a substituent selected from the group consisting of halogen, $C_{1-4}$alkyl, cyano, $NR^E R^F$, —C(=NH)—$NR^E R^F$, —C(O)—CH$_2$—$NR^E R^F$, —C(O)—CH$_2$CH$_2$—$NR^E R^F$ and phenyl; wherein $R^E$ and $R^F$ are each independently selected from the group consisting of hydrogen and $C_{1-4}$alkyl;
(Ring B) is selected from the group consisting of phenyl and 4 to 10 membered, nitrogen containing ring structure;
(Ring C) is selected from the group consisting of 4 to 10 membered, nitrogen containing ring structure; wherein (Ring C) is optionally substituted with one to two substituents independently selected from the group consisting $C_{1-4}$alkyl;
or a pharmaceutically acceptable salt thereof.

2. A compound as in claim 1, wherein
a is an integer from 0 to 1;
X is selected from the group consisting of —S— and —O—;
$R^1$ is selected from the group consisting of $C_{1-2}$alkyl;
b is an integer from 0 to 2;
$R^2$ is selected from the group consisting of halogen, hydroxy, nitro, $NR^A R^B$, $C_{1-4}$alkyl, —O—$C_{1-4}$alkyl, —S—$C_{1-2}$alkyl and fluorinated $C_{1-2}$alkyl; wherein $R^A$ and $R^B$ are each independently selected from the group consisting of hydrogen and $C_{1-2}$alkyl;
$R^3$ is selected from the group containing of hydrogen, halogen, hydroxy, —O—$C_{1-4}$alkyl and $NR^C R^D$; wherein $R^C$ and $R^D$ are each independently selected from the group consisting of hydrogen and $C_{1-2}$alkyl;
Y is CH and Z is CH;
Q is selected from the group consisting of -($L^1$)$_c$-(Ring A), -($L^1$)$_c$-(Ring B)-(Ring C) and -(Ring B)-$L^1$-(Ring C);
c is an integer from 0 to 1;
$L^1$ is selected from the group consisting of —CH$_2$—, —CH(OH)—, —CH$_2$CH$_2$—, —CH$_2$CH$_2$CH$_2$—, —CH=CH—, —CH=CH—CH$_2$—, —O—, —O—CH$_2$—, —C(O)—, —C(O)—C(O)—, —C(O)—CH$_2$—, —C(O)—N($R^4$)—, —N($R^4$)—, —N($R^4$)—CH$_2$—, —N($R^4$)—CH$_2$CH$_2$—, —N($R^4$)—(CO)—, —N($R^4$)—C(O)—CH$_2$—, —N($R^4$)—C(O)—CH$_2$CH$_2$— and —N($R^4$)—C(O)—N($R^5$)—; wherein $R^4$ and $R^5$ are each independently selected from the group consisting of hydrogen and $C_{1-2}$alkyl;
(Ring A) is selected from the group consisting of phenyl and 4 to 10 membered, nitrogen containing ring structure; wherein (Ring A) is optionally substituted with a substituent selected from the group consisting of halogen, $C_{1-4}$alkyl, cyano, $NR^E R^F$, —C(=NH)—$NR^E R^F$, —C(O)—CH$_2$—$NR^E R^F$, —C(O)—CH$_2$CH$_2$—$NR^E R^F$ and phenyl; wherein $R^E$ and $R^F$ are each independently selected from the group consisting of hydrogen and $C_{1-2}$alkyl;
(Ring B) is selected from the group consisting of phenyl and a 4 to 6 membered, nitrogen containing ring structure;
(Ring C) is selected from the group consisting of a 4 to 6 membered, nitrogen containing ring structure; where (Ring C) is optionally substituted with one to two substituents independently selected from the group consisting of $C_{1-4}$alkyl;
or a pharmaceutically acceptable salt thereof.

3. A compound as in claim 2, wherein
a is an integer from 0 to 1;
X is selected from the group consisting of —S— and —O—;
$R^1$ is selected from the group consisting of $C_{1-2}$alkyl;
b is an integer from 0 to 2;
$R^2$ is selected from the group consisting of halogen, $C_{1-2}$alkyl, —O—$C_{1-2}$alkyl, nitro and $NR^A R^B$; wherein $R^A$ and $R^B$ are each independently selected from the group consisting of hydrogen and $C_{1-2}$alkyl;
$R^3$ is selected from the group containing of hydrogen, hydroxy and —O—$C_{1-2}$alkyl;
Y is CH and Z is CH;
Q is selected from the group consisting of -($L^1$)$_c$-(Ring A), -($L^1$)$_c$-(Ring B)-(Ring C) and -(Ring B)-$L^1$-(Ring C);
c is an integer from 0 to 1;
$L^1$ is selected from the group consisting of —CH$_2$—, —CH(OH)—, —CH$_2$CH$_2$—, —CH=CH—, —O—, —O—CH$_2$—, —C(O)—, —C(O)—C(O)—, —C(O)—CH$_2$—, —C(O)—N($R^4$)—, —N($R^4$)—, —N($R^4$)—

CH$_2$—, —N(R$^4$)—CH$_2$CH$_2$—, —N(R$^4$)—(CO)—, —N(R$^4$)—C(O)—CH$_2$—, —N(R$^4$)—C(O)—CH$_2$—CH$_2$— and —N(R$^4$)—C(O)—N(R$^5$)—; wherein R$^4$ and R$^5$ are each independently selected from the group consisting of hydrogen and C$_{1-2}$alkyl;

(Ring A) is selected from the group consisting of phenyl and 4 to 9 membered, nitrogen containing ring structure; wherein (Ring A) is optionally substituted with a substituent selected from the group consisting of halogen, C$_{1-4}$alkyl, cyano, amino, —C(O)—CH$_2$—NH$_2$, —C(O)—CH$_2$CH$_2$—NH$_2$, —C(=NH)—NH$_2$, and phenyl;

(Ring B) is selected from the group consisting of phenyl and a 4 to 6 membered, nitrogen containing ring structure;

(Ring C) is selected from the group consisting of a 4 to 6 membered, nitrogen containing ring structure; where (Ring C) is optionally substituted with one to two substituents independently selected from the group consisting of C$_{1-2}$alkyl;

or a pharmaceutically acceptable salt thereof.

4. A compound as in claim 3, wherein
a is an integer from 0 to 1;
X is selected from the group consisting of —S— and —O—;
R$^1$ is selected from the group consisting of methyl and ethyl;
b is an integer from 0 to 2;
R$^2$ is selected from the group consisting of bromo, fluoro, methyl, methoxy, nitro and amino;
R$^3$ is selected from the group consisting of hydrogen, hydroxy, —O-methyl and —O-ethyl;
Y is CH and Z is CH;
Q is selected from the group consisting of -(L$^1$)$_c$-(Ring A), -(L$^1$)$_c$-(Ring B)-(Ring C) and -(Ring B)-L$^1$-(Ring C);
c is an integer from 0 to 1;
L$^1$ is selected from the group consisting of —CH$_2$—, —CH(OH)—, —CH$_2$—CH$_2$—, —CH=CH—, —O—, —O—CH$_2$—, —C(O)—, —C(O)—NH—, —C(O)—CH$_2$—, —C(O)—C(O)—, —NH—, —NH—C(O)—, —NH—CH$_2$—, —N(ethyl)-CH$_2$—, —NH—CH$_2$—CH$_2$—, —NH—C(O)—CH$_2$—, —NH—C(O)—CH$_2$—CH$_2$— and —NH—C(O)—NH—;

(Ring A) is selected from the group consisting of 3-cyano-phenyl, 3-benzimidamide, azetidin-3-yl, piperazin-1-yl, 4-methyl-piperazin-1-yl, 3-methyl-piperazin-1-yl, 4-ethyl-piperazin-1-yl, 4-isopropyl-piperazin-1-yl, piperazin-4-yl, piperidin-1-yl, piperidin-2-yl, piperidin-3-yl, piperidin-4-yl, 4-amino-piperidin-4-yl, 4-methyl-piperidin-4-yl, 4-fluoro-piperidin-4-yl, 4-phenyl-piperidin-4-yl, pyrrolidin-2-yl, pyrrolidin-3-yl, pyrid-2-yl, pyrid-3-yl, pyrid-4-yl, 6-methyl-pyrid-3-yl, 1,2,3,6-tetrahydropyrid-4yl, 1-(amino-methyl-carbonyl)-1,2,3,6-tetrahydropyrid-4-yl, 1-(amino-ethyl-carbonyl)-1,2,3,6-tetrahydropyrid-4-yl, 1,4-diazepan-1-yl, benzimidazol-5-yl, 1-methyl-benzimidazol-6-yl, 1-methyl-benzimidazol-5-yl, benzo[c][1,2,5]oxadiazol-5-yl, 2,5-diazabicyclo[2.2.1]hept-1-yl, 2,7-diazaspiro[4,4]nonan-2-yl and octahydropyrrolo[3,4-c]pyrrol-2-yl;

(Ring B) is selected form the group consisting of phenyl, azetidin-1-yl, azetidin-3-yl, piperidin-3-yl, piperidin-4-yl, piperazin-1-yl, pyrrolidin-1-yl and 1-imidazolidin-2-one;

(Ring C) is selected from the group consisting of azetidin-3-yl, piperidin-2-yl, piperidin-3-yl, piperidin-4-yl, piperazin-1-yl, piperazin-4-yl, 4-methyl-piperazin-1-yl, 3,5-dimethyl-piperazin-1-yl, pyrrolidin-2-yl, pyrrolidin-3-yl, pyrid-2-yl, pyrid-3-yl, pyrid-4-yl and imidazol-1-yl;

or a pharmaceutically acceptable salt thereof.

5. A compound as in claim 4, wherein
a is an integer from 0 to 1;
X is selected from the group consisting of —S— and —O—;
R$^1$ is selected from the group consisting of methyl and ethyl;
b is an integer from 0 to 1;
R$^2$ is selected from the group consisting of bromo, fluoro, methyl, methoxy, nitro and amino;
R$^3$ is selected from the group consisting of hydrogen, hydroxy, —O-methyl and —O-ethyl;
Y is CH and Z is CH;
Q is selected from the group consisting of -(L$^1$)$_c$-(Ring A), -(L$^1$)$_c$-(Ring B)-(Ring C) and -(Ring B)-L$^1$-(Ring C);
c is an integer from 0 to 1;
L$^1$ is selected from the group consisting of —CH$_2$—CH$_2$—, —CH=CH—, —O—, —O—CH$_2$—, —C(O)—, —NH—, —NH—C(O)—, —N(ethyl)-CH$_2$—, —NH—CH$_2$—CH$_2$—, —NH—C(O)—CH$_2$—, —NH—C(O)—CH$_2$—CH$_2$— and —NH—C(O)—NH—;

(Ring A) is selected from the group consisting of 3-benzimidamide, azetidin-3-yl, piperazin-1-yl, 3-methyl-piperazin-1-yl, piperidin-2-yl, piperidin-3-yl, piperidin-4-yl, 4-amino-piperidin-4-yl, 4-methyl-piperidin-4-yl, 4-fluoro-piperidin-4-yl, pyrrolidin-2-yl, pyrrolidin-3-yl, pyrid-3-yl, 1,2,3,6-tetrahydropyrid-4yl, 1-(amino-ethyl-carbonyl)-1,2,3,6-tetrahydropyrid-4-yl, 1,4-diazepan-1-yl, benzimidazol-5-yl, and 2,5-diazabicyclo[2.2.1]hept-1-yl;

(Ring B) is selected from the group consisting of phenyl, azetidin-1-yl, piperidin-1-yl, piperazin-1-yl, pyrrolidin-1-yl and 1-imidazolidin-2-one;

(Ring C) is selected from the group consisting of piperidin-1-yl, piperidin-4-yl, piperazin-1-yl, 4-methyl-piperazin-1-yl, 3,5-dimethyl-piperazin-1-yl, pyrrolidin-3-yl and pyrid-4-yl;

or a pharmaceutically acceptable salt thereof.

6. A compound as in claim 4, wherein
a is an integer from 0 to 1;
X is selected from the group consisting of —S— and —O—;
R$^1$ is selected from the group consisting of methyl and ethyl;
b is an integer from 0 to 1;
R$^2$ is selected from the group consisting of fluoro, methyl, methoxy, nitro and amino;
R$^3$ is selected from the group consisting of hydrogen and —O-methyl;
Y is CH and Z is CH;
Q is selected from the group consisting of -(L$^1$)$_c$-(Ring A) and -(L$^1$)$_c$-(Ring B)-(Ring C);
c is an integer from 0 to 1;
L$^1$ is selected from the group consisting of —CH=CH—, —O—CH$_2$—, —NH—C(O)—, —NH—CH$_2$—, —NH—C(O)—CH$_2$—CH$_2$— and —NH—C(O)—NH—;

(Ring A) is selected from the group consisting of azetidin-3-yl, piperazin-1-yl, 3-methyl-piperazin-1-yl, piperidin-3-yl, piperidin-4-yl, 4-amino-piperidin-4-yl, pyrrolidin-2-yl, pyrrolidin-3-yl, pyrid-3-yl, 1,2,3,6-tetrahydropyrid-4yl, 1-(amino-ethyl-carbonyl)-1,2,3,6-tetrahydropyrid-4-yl and benzimidazol-5-yl;

(Ring B) is selected form the group consisting of phenyl, azetidin-1-yl, piperazin-1-yl, and 1-imidazolidin-2-one;
(Ring C) is selected from the group consisting of piperidin-1-yl, piperidin-4-yl, piperazin-1-yl, 3,5-dimethyl-piperazin-1-yl, pyrrolidin-3-yl and pyrid-4-yl;
or a pharmaceutically acceptable salt thereof.

7. A compound as in claim 6, wherein
a is an integer from 0 to 1;
X is selected from the group consisting of —S— and —O—;
$R^1$ is methyl;
b is an integer from 0 to 1;
$R^2$ is selected from the group consisting of fluoro, methyl, methoxy, nitro and amino;
$R^3$ is hydrogen;
Y is CH and Z is CH;
Q is selected from the group consisting of -($L^1$)$_c$-(Ring A) and -($L^1$)$_c$-(Ring B)-(Ring C);
c is an integer from 0 to 1;
$L^1$ is selected from the group consisting of —CH=CH—, —O—CH$_2$—, —NH—C(O)—, —NH—CH$_2$—, —NH—C(O)—CH$_2$—CH$_2$— and —NH—C(O)—NH—;
(Ring A) is selected from the group consisting of azetidin-3-yl, piperazin-1-yl, 3-methyl-piperazin-1-yl, piperidin-3-yl, piperidin-4-yl, 4-amino-piperidin-4-yl, pyrrolidin-2-yl, pyrrolidin-3-yl, pyrid-3-yl, 1,2,3,6-tetrahydropyrid-4yl, 1-(amino-ethyl-carbonyl)-1,2,3,6-tetrahydropyrid-4-yl and benzimidazol-5-yl;
(Ring B) is selected form the group consisting of azetidin-1-yl, piperazin-1-yl, and 1-imidazolidin-2-one;
(Ring C) is selected from the group consisting of piperidin-1-yl, piperidin-4-yl, piperazin-1-yl, pyrrolidin-3-yl and pyrid-4-yl;
or a pharmaceutically acceptable salt thereof.

8. A compound as in claim 4, wherein
a is an integer from 0 to 1;
X is selected from the group consisting of —S— and —O—;
$R^1$ is methyl;
b is an integer from 0 to 1;
$R^2$ is selected from the group consisting of fluoro, methyl, methoxy and amino;
$R^3$ is hydrogen;
Q is -($L^1$)$_c$-(Ring A);
c is an integer from 0 to 1;
$L^1$ is selected from the group consisting of —CH=CH— and —NH—C(O);
(Ring A) is selected from the group consisting of azetidin-3-yl, piperidin-4-yl, pyrid-3-yl, 1,2,3,6-tetrahydropyrid-4-yl and benzimidazol-5-yl;
or a pharmaceutically acceptable salt thereof.

9. A compound as in claim 4, selected from the group consisting of
N-(3-(Methylthio)-1-phenyl-1H-indazol-6-yl)piperidine-4-carboxamide;
3-(Methylthio)-1-phenyl-6-(4-(piperidin-4-yl)piperazin-1-yl)-1H-indazole;
3-Methylsulfanyl-6-(1,2,3,6-tetrahydropyrid-4-yl)-1-(3-methylphenyl)-1H-indazole;
and pharmaceutically acceptable salts thereof.

10. A pharmaceutical composition comprising a pharmaceutically acceptable carrier and a compound of claim 1.

11. A pharmaceutical composition made by mixing a compound of claim 1 and a pharmaceutically acceptable carrier.

12. A process for making a pharmaceutical composition comprising mixing a compound of claim 1 and a pharmaceutically acceptable carrier.

\* \* \* \* \*

UNITED STATES PATENT AND TRADEMARK OFFICE
CERTIFICATE OF CORRECTION

| | | |
|---|---|---|
| PATENT NO. | : 8,822,447 B2 | Page 1 of 1 |
| APPLICATION NO. | : 13/091344 | |
| DATED | : September 2, 2014 | |
| INVENTOR(S) | : Xuqing Zhang et al. | |

It is certified that error appears in the above-identified patent and that said Letters Patent is hereby corrected as shown below:

In the claims,

COL. 115, (Claim 4), line 52, after "pyrrolidin-3-yl," insert -- 3-amino-pyrrolidin-1-yl, --

COL. 115, (Claim 4), line 62, after "azetidin-3-yl," insert -- piperidin-1-yl, --

COL. 115, (Claim 4), line 66, after "azetidin-3-yl," insert -- piperidin-1-yl, --

COL. 116 (Claim 5), line 22, after "-NH-C(O)-," insert -- -NH-CH$_2$-, --

COL. 116, (Claim 5), line 28, after "3-methyl-piperazin-1-yl," insert -- piperidin-1-yl, --

COL. 116, (Claim 5), line 31, after "pyrrolidin-3-yl," insert -- 3-amino-pyrrolidin-1-yl, --

Signed and Sealed this
First Day of March, 2016

Michelle K. Lee
*Director of the United States Patent and Trademark Office*